(12) United States Patent
Thompson et al.

(10) Patent No.: US 7,572,926 B2
(45) Date of Patent: Aug. 11, 2009

(54) PLANT DESATURASES—COMPOSITIONS AND USES

(75) Inventors: Gregory A. Thompson, Davis, CA (US); Vic C. Knauf, Winters, CA (US)

(73) Assignee: Calgene, Inc., Davis, CA (US)

( * ) Notice: Subject to any disclaimer, the term of this patent is extended or adjusted under 35 U.S.C. 154(b) by 290 days.

(21) Appl. No.: 11/415,867

(22) Filed: May 2, 2006

(65) Prior Publication Data

US 2007/0016981 A1 Jan. 18, 2007

Related U.S. Application Data

(60) Division of application No. 07/762,762, filed on Sep. 16, 1991, now Pat. No. 7,037,692, which is a continuation-in-part of application No. PCT/US91/01746, filed on Mar. 14, 1991, and a continuation-in-part of application No. 07/494,106, filed on Mar. 16, 1990, now abandoned, and a continuation-in-part of application No. 07/615,784, filed on Nov. 14, 1990, now abandoned, which is a continuation-in-part of application No. 07/567,373, filed on Aug. 13, 1990, now abandoned, and a continuation-in-part of application No. 07/494,106, filed on Mar. 16, 1990, now abandoned.

(51) Int. Cl.
*C11B 1/00* (2006.01)
*C12N 15/82* (2006.01)

(52) U.S. Cl. .......................... 554/8; 800/281
(58) Field of Classification Search .................. None
See application file for complete search history.

(56) References Cited

U.S. PATENT DOCUMENTS

| | | | | |
|---|---|---|---|---|
| 4,394,443 | A | 7/1983 | Weissman et al. | 435/6 |
| 4,446,235 | A | 5/1984 | Seeburg | 435/91.51 |
| 5,057,419 | A | 10/1991 | Martin et al. | 435/134 |
| 5,107,065 | A | 4/1992 | Shewmaker et al. | 800/298 |
| 6,117,677 | A | 9/2000 | Thompson et al. | 435/410 |

FOREIGN PATENT DOCUMENTS

| | | |
|---|---|---|
| EP | 0 189 707 | 6/1986 |
| EP | 0 255 377 | 2/1988 |
| EP | 0 255 378 | 2/1988 |
| EP | 0 323 753 | 7/1989 |
| NL | 8800794 | 11/1988 |
| NL | 9002130 | 9/1990 |
| WO | WO 90/12084 | 10/1990 |
| WO | WO 91/11906 | 8/1991 |
| WO | WO 91/18985 | 12/1991 |

OTHER PUBLICATIONS

Bafor et al., "Properties of the glycerol acylating enzymes in microsomal preparations from the developing seeds of safflower (*Carthamus tinctorius*) and turnip rape (*Brassica campestris*) and their ability to assemble cocoa-butter type fats," *JAOCS*, 67(4):217-225, 1990.

Battey et al., "Genetic engineering for plant oils: potential and limitations," *Trends in Biotech.*, 7:122-126, 1989.

Bodman et al., "Processing of edible soybean oil," In: Soybeans and Soybean Products, Interscience Publishers, Inc., New York, NY, pp. 649-725, 1951.

Browse et al., "A mutant of arabidopsis deficient in C18:3 and C16:3 leaf lipids," *Chem. Abstracts*, 105:449, Abstract No. 169077, 1986.

Browse et al., "A mutant of arabidopsis deficient in C18:3 and C16:3 leaf lipids," *Plant Physiol.*, 81(3):859-864, 1986.

Carver et al., "Developmental changes in acyl-compositions of soybean seed selected for high oleic acid concentration," *Crop Science*, 24:1016-1019, 1984.

Chesebrough, "Changes in the enzymes for fatty acid synthesis and desaturation during acclimation of developing soybean seeds to altered growth temperature," *Plant Physiol.*, 90:760-764, 1989.

Downey et al., "Genetic control of fatty acid composition in oilseed crops," Proceedings of the Flax Institute USA, 41(3):1-3.

European Patent Office Search Report for App. No. 91907317.1, May 14, 1992.

European Patent Office Search Report for PCT/US91/01746, Aug. 7, 1991.

Goodman et al., "Biotechnology and its impact on future developments in soybean production and use," World Soybean Research Conference III: Prodceedings, Shibles (ed.), Westview Press, pp. 261-271, 1985.

Graef et al., "Inheritance of three stearic acid mutants of soybean," *Crop Science*, 25:1076-1079, 1985.

Inkpen et al., "Desaturation of palmitate and stearate by cell-free fractions from soybean cotyledons," *Lipids*, 4(6):539-543, 1968.

Jaworsky et al., "Fat metabolism in higher plants: properties of a soluble stearyl-acyl carrier protein desaturase from maturing *Carthamus tinctorius,*" *Archives of Biochem. And Biophys.*, 162:158-165, 1974.

Johnson et al., "Isotope effects in the desaturation of stearic to oleic acid," *Lipids*, 6(2):78-84, 1971.

Kater et al., "cDNA cloning and expression of *Brassica napus* enoyl-acyl carrier protein reductase in *Escherichia coli*," *Plant Mol. Biol.*, 17:895-909, 1991.

(Continued)

*Primary Examiner*—Elizabeth F McElwain
(74) *Attorney, Agent, or Firm*—Chunping Li, Esq.; Sonnenschein Nath & Rosenthal LLP

(57) ABSTRACT

By this invention, compositions and methods of use of plant desaturase enzymes, especially Δ-9 desaturases, are provided. Of special interest are methods and compositions of amino acids and nucleic acid sequences related to biologically active plant desaturases as well as sequences, especially nucleic acid sequences, which are to be used as probes, vectors for transformation or cloning intermediates. Biologically active sequences may be found in a sense or anti-sense orientation as to transcriptional regulatory regions found in various constructs.

4 Claims, 42 Drawing Sheets

OTHER PUBLICATIONS

Kater, et al, "Purification and cloning of *Brassica napus* stearoyl-ACP desaturase," *J. Cell. Biochem. Suppl.*, 15A:133, (1991).

Knauf et al., "Reprogramming levels of fatty acid synthesis enzymes in developing embryos of rapeseed," *J. Cell Biochem. Suppl.*, 14E:266, 1990.

Knauf, "The application of genetic engineering to oilseed crops," *Trends in Biotech.*, 5:40-47, 1978.

Mattson et al., "Comparison of effects of dietary saturated, monosaturated, and polyunsaturated fatty acids on plasma lipids and lipoproteins in man," *J. of Lipid Research*, 26:194-201, 1985.

McKeon et al., "Purification and characterization of the stearoyl-acyl carrier protein desaturase and the acyl-acyl carrier Protein thioesterase from maturing seeds of safflower," *J. Bio. Chem.*, 257(20):12141-12147, 1982.

McKeon et al., "Stearoyl-acyl carrier protein desaturase from safflower seeds," *Methods in Enzymology*, 71:275-281, 1981.

Moore et al., "The inheritance of high oleic acid in peanut," *Journal of Heredity*, 80(3):252-523, 1989.

Nagi et al., "Enzymatic desaturation of stearyl acyl carrier protein," *J. Biol. Chem.*, 241:1925-1927, 1966.

Rock et al., "Preparative enzymatic synthesis of acyl-acyl carrier protein," *Methods in Enzymology*, 72:397-403, 1981.

Talamo et al., "A new assay for fatty acid desaturation," *Analyst. Biochem.*, 29:300-304, 1969.

Thompson et al., "Primary structures of the precursor and mature forms of stearoylacyl carrier protein desaturase from safflower embryos and requirement of ferredoxin for enzyme activity," *Proc. Natl. Acad. Sci. USA*, 99:2579-2582, 1991.

Van der Krol et al., "Modulation of eukaryotic gene expression by complementary RNA or DNA sequences," *Bio Techniques*, 6(10):958-997, 1988.

Wilcox et al., "Genetic alteration of soybean oil composition by a chemical mutagen," *JAOCS*, 61:97-100, 1984.

Wolf et al., "Effect of temperature on soybean seed dconstituents: oil, protein, moisture, fatty acids, amino acids and sugars," *JAOCS*, 59:230-232, 1982.

F1: ASTLGSSTPKVDNAKKPFQPPREVHVQVTH$_X^S$MPPQKIEIFKSIEG$_R^W$AEQNILV$_F^H$LKPVEKCWQ

F2: DFLPDPA$_T^S$EGFDEQVKELRARAKEIPDDYFVVLVGDMITEEALPTYQTMLNTLDGV

F3: DETGASLTPWAVWT

F4: DLLHTYLYLSGRV

F5: DMRQIQKTIQYLI

F6: TENSPYLGFIYTSFQER

F7: DV$_F^K$LAQI$_Q^C$GTIASDEKRHETAYTKIVEKLFEIDPDGTVLAFADMMRKKI$_T^S$MPAHLMY

F8: DNLF

F9: dvF1AV$_I^A$QRL$_I^G$VYTAK

F10: DYADILEFLVGRWK

F11: VADLTGLSGEGRKA$_G^Q$DYVCGLPPRIRRLEERAQGRAKEGPVVPFSWIFDRQVKL

FIGURE 1

```
                                                        HindIII
                                                          |
  1  GCTCACTTGTGTGGTGGGAGGAGAAAAACAGAACTCACAAAAAGCTTTGCGACTGCCAAGAACAACAACA        69
                                                          42

70  ACAACAAGATCAAGAAGAAGAAGAAGAAGATCAAAAATGGCTCTTCGAATCACTCCAGTGACCTTGCAA        138
                                    METAlaLeuArgIleThrProValThrLeuGln

EcoRV                           BglII              NcoI
               |                               |                  |
139  TCGGAGAGATATCGTTCGTTTCGTTTCCTAAGAAGGCTAATCTCAGATCTCCCAAATTCGCCATGGCC        207
     SerGluArgTyrArgSerPheSerPheProLysLysAlaAsnLeuArgSerProLysPheAlaMETAla
                149                            185                201

HindII
                                                  |
208  TCCACCCTCGGATCATCCACACCGAAGGTTGACAATGCCAAGAAGCCTTTCAACCTTCCACGAGAGTT        276
     SerThrLeuGlySerSerThrProLysValAspAsnAlaLysLysProPheGlnProPheArgGluVal
                                          238

277  CATGTTCAGGTGACGCACTCCATGCCACCACAGAAGATTTCAAATCCATCGAGGTTGGGCT           345
     HisValGlnValThrHisSerMETProProGlnLysIleSerIleGluGlyTrpAla

346  GAGCAGAACATATTGTTCACCTAAAGCCAGTGGAGAAATGTTGGCAAGCACAGGATTTCTTGCCGGAC        414
     GluGlnAsnIleLeuValHisLeuLysProValGluLysCysTrpGlnAlaGlnAspPheLeuProAsp
```

FIGURE 2
Page 1 of 4

415 CCTGCATCTGAAGGATTTGATGAACAAGTGCAGGGCAAGAGCAAAGGAGATTCCTGATGAT 483
    ProAlaSerGluGlyPheAspGluGlnValLysGluLeuArgAlaArgAlaLysGluIleProAspAsp

484 TACTTTGTTGTTTGGTTGGAGATATGATTACAGAGGAAGCCCTACCTACCAAACAATGCTTAAT 552
    TyrPheValValLeuValGlyAspMETIleThrGluGluAlaLeuProThrThrTyrGlnThrMETLeuAsn

553 ACCCTAGATGGTGTACGTGATGAGACTGGGGCTAGCCTTACGCCCTTGGGCTGTCTGGACTAGGGCTTGG 621
    ThrLeuAspGlyValArgAspGluThrGlyAlaSerLeuThrProTrpAlaValTrpThrArgAlaTrp

AccI
                                    PvuII                            |
622 ACAGCTGAAGAGAACAGGCATGGCGATCTTCTCCACACCTATCTCTACCTTTCTGGGCGGGTAGACATG 690
    ThrAlaGluGluAsnArgHisGlyAspIleLeuHisThrTyrLeuTyrLeuSerGlyArgValAspMET
                                                                    684

BamHI
                                              |
691 AGGCAGATACAGAAGACAATTCAGTATCTCATTGGGTCAGGAATGGATCCTCGTACCGAAAACAGCCCC 759
    ArgGlnIleGlnLysThrIleGlnTyrLeuIleGlySerGlyMETAspProArgThrGluAsnSerPro
                                              736

760 TACCTTGGGTTCATCTACACATCGTTTCAAGAGCGTGCCACATTTGTTCTCACGGAAACACCCGCCAGG 828
    TyrLeuGlyPheIleTyrThrSerPheGlnGluArgAlaThrPheValSerHisGlyAsnThrAlaArg

FIGURE 2
Page 2 of 4

SphI
|
829 CATGCAAAGGATCATGGGGACGTGAAACTGGCGCAAATTTGTGGTACAATCGCGTCTGACGAAAAGCGT 897
    HisAlaLysAspHisGlyAspValLysLeuAlaGlnIleCysGlyThrIleAlaSerAspGluLysArg
                                                                    833

ClaI
                                                |
898 CACGAGACCGCTTATACAAAGATAGTCGAAAAGCTATTCGAGATCGATCCTGATGGCACCGTTCTTGCT 966
    HisGluThrAlaTyrThrLysIleGluLysLeuPheGluIleAspProAspGlyThrValLeuAla
                                                                942

BglII
                        |
967 TTTGCCGACATGATGAGGAAAAAGATCTCGATGCCCGCACACTTGATGTACGATGGGCGTGATGACAAC 1035
    PheAlaAspMETMETArgLysLysIleSerMETProAlaHisLeuMETTyrAspGlyArgAspAspAsn
                                990

AccI
                                                |
1036 CTCTTCGAACATTTCTCGGCGGTTGCCAAAGACTCGGCGTCTACACCGCCAAAGACTACGCCGACATA 1104
     LeuPheGluHisPheSerAlaValAlaAlaGlnArgLeuGlyValTyrThrAlaLysAspTyrAlaAspIle
                                                                    1077

1105 CTGGAATTTCTGGTCGGGCGGTGAAAGTGGCGGATTTGACCGGCCTATCTGGTGAAGGGCGTAAAGCG 1173
     LeuGluPheLeuValGlyArgTrpLysValAlaAspLeuThrGlyLeuSerGlyGluGlyArgLysAla

FIGURE 2
Page 3 of 4

```
                                                                    SacI
                                                                     |
1174  CAAGATTATGTTTGCGGGTTGCCACCAAGAATCAGAAGGCTGGAGGAGAGAGCTCAAGGGCGAGCAAAG  1242
      GlnAspTyrValCysGlyLeuProProArgIleArgArgLeuGluArgAlaGlnGlyArgAlaLys
                                                               1228

PvuII
                         |
1243  GAAGGACCTGTGTTCCATTCAGCTGGATTTTCGATAGACAGGTGAAGCTGAAGAAAAAAAACGA  1311
      GluGlyProValValProPheSerTrpIlePheAspArgGlnValLysLeu
                                                      1266

1312  GCAGTGAGTTCGGTTTCTGTTGGCTTATTGGGTAGAGGTTAAAACCTATTTTAGATGTCTGTTTCGTGT  1380

1381  AATGTGGTTTTTTTTCTTCTAATCTTGAATCTGGTATTGTGTCGTTGAGTTCGCGTGTGTAAACTTG  1449

1450  TGTGGCTGTGGACATATTATAGAACTCGTTATGCCAATTTTGATGACGGTGGTTATCGTCTCCCCTGGT  1518

1519  GTTTTTTTATTGTTT  1533
```

FIGURE 2
Page 4 of 4

1   AAAGAAAAAGGTAAGAAAAAAAACAATGGCTCTCAAGCTCTCAATCCTTTCCTTTCTCAAACCCAAAAGT   69
                              METAlaLeuLysLeuAsnProPheLeuSerGlnThrGlnLysL
                                                    BglII
                                                      |

70  TACCTTCTTTCGCTCTTCCACCAATGGCCAGTACCAGATCTCCTAAGTTCTACATGGCCTTCTACCCTCA  138
    euProSerPheAlaLeuProProMETAlaSerThrArgSerProLysPheTyrMETAlaSerThrLeuL

139 AGTCTGGTTCTAAGGAAGTTGAGAATCTCAAGAAGCCTTTCATGCCTCCTCGGGAGGTACATGTTCAGG  207
    ysSerGlySerLysGluValGluAsnLeuLysLysProPheMETProProArgGluValHisValGlnV

208 TTACCCATTCTATTGCCA  225
    alThrHisSerIleAla

FIGURE 3A

```
AAAAGAAAAA GGTAAGAAAA AAAACA ATG GCT CTC AAG CTC AAT CCT TTC CTT TCT         56
                             MET Ala Leu Lys Leu Asn Pro Phe Leu Ser

CAA ACC CAA AAG TTA CCT TCT TTC GCT CTT CCA CCA ATG GCC AGT ACC AGA TCT     110
Gln Thr Gln Lys Leu Pro Ser Phe Ala Leu Pro Pro MET Ala Ser Thr Arg Ser

CCT AAG TTC TAC ATG GCC TCT ACC CTC AAG TCT GGT TCT AAG GAA GTT GAG AAT     164
Pro Lys Phe Tyr MET Ala Ser Thr Leu Lys Ser Gly Ser Lys Glu Val Glu Asn

CTC AAG AAG CCT TTC ATG CCT CCT CGG GAG GTA CAT GTT CAG GTT ACC CAT TCT     218
Leu Lys Lys Pro Phe MET Pro Pro Arg Glu Val His Val Gln Val Thr His Ser

ATG CCA CCC CAA AAG ATC TTT GAG ATC CTA TCC AAA TGG GCT GAG GAG             272
MET Pro Pro Gln Lys Ile Phe Glu Ile Leu Ser Lys Asn Trp Ala Glu Glu

AAC ATT CTG GTT CAT CTG AAG CCA GTT GAG AAA TGT TGG CAA CCG CAG GAT TTT     326
Asn Ile Leu Val His Leu Lys Pro Val Glu Lys Cys Trp Gln Pro Gln Asp Phe

TTG CCA GAT CCC GCC TCT GAT GGA TTT GAT GAG CAA GTC AGG GAA CTC AGG GAG     380
Leu Pro Asp Pro Ala Ser Asp Gly Phe Asp Glu Gln Val Arg Glu Leu Arg Glu

AGA GCA AAG GAG ATT CCT GAT GAT TAT TTT GTT TTG GTT GGA GAC ATG ATA         434
Arg Ala Lys Glu Ile Pro Asp Asp Tyr Phe Val Leu Val Gly Asp MET Ile

ACG GAA GCC CTT CCC ACT TAT CAA ACA ATG CTG AAT ACC TTG GAT GGA GTT         488
Thr Glu Ala Leu Pro Thr Tyr Gln Thr MET Leu Asn Thr Leu Asp Gly Val
```

FIGURE 3B
Page 1 of 3

```
CGG GAT GAA ACA GGT GCA AGT CCT ACT TCT TGG GCA ATT TGG ACA AGG GCA TGG    542
Arg Asp Glu Thr Gly Ala Ser Pro Thr Ser Trp Ala Ile Trp Thr Arg Ala Trp

ACT GCG GAA GAG AAT AGA GAC CAT GGT GAC CTC CTC AAT AAG TAT CTC TAC CTA TCT    596
Thr Ala Glu Glu Asn Arg Asp His Gly Asp Leu Leu Asn Lys Tyr Leu Tyr Leu Ser

GGA CGA GTG GAC ATG AGG GCA ATT GAG AAG ACA ATT CAA TAT TTG ATT GGT TCA    650
Gly Arg Val Asp MET Arg Ala Ile Glu Lys Thr Ile Gln Tyr Leu Ile Gly Ser

GGA ATG GAT CCA CGG ACA GAA AAC AGT CCA TAC CTT GGG TTC ATC TAT ACA TCA    704
Gly MET Asp Pro Arg Thr Glu Asn Ser Pro Tyr Leu Gly Phe Ile Tyr Thr Ser

TTC CAG GAA AGG GCA ACC TTC ATT TCT CAT GGG AAC ACT GCC CGA CAA GCC AAA    758
Phe Gln Glu Arg Ala Thr Phe Ile Ser His Gly Asn Thr Ala Arg Gln Ala Lys

GAG CAT GGA GAC ATA AAG TTG GCT CAA ATA TGT GGT ACA ATT GCT GAT GAG    812
Glu His Gly Asp Ile Lys Leu Ala Gln Ile Cys Gly Thr Ile Ala Asp Glu

AAG CGC CAT GAG ACA GCC TAC ACA AAG ATA GTG GAA AAA CTC TTT GAG ATT GAT    866
Lys Arg His Glu Thr Ala Tyr Thr Lys Ile Val Glu Lys Leu Phe Glu Ile Asp

CCT GAT GGA ACT GTT TTG GCT TTT GCT GAT ATG AGA ATG AAA ATT TCT ATG    920
Pro Asp Gly Thr Val Leu Ala Phe Ala Asp MET Arg MET Arg Lys Ile Ser MET

CCT GCA CAC TTG ATG TAT GAT GGC CGA GAT GAT AAT CTT GAC CAC TTT TCA    974
Pro Ala His Leu MET Tyr Asp Gly Arg Asp Asp Asn Leu Phe Asp His Phe Ser
```

FIGURE 3B
Page 2 of 3

```
GCT GTT GCG CAG CGT CTT GGA GTC TAC ACA GCA AAG GAT TAT GCA GAT ATA TTG    1028
Ala Val Ala Gln Arg Leu Gly Val Tyr Thr Ala Lys Asp Tyr Ala Asp Ile Leu

GAG TTC TTG GTG GGC AGA TGG AAG GTG GAT AAA CTA ACG GGC CTT TCA GCT GAG    1082
Glu Phe Leu Val Gly Arg Trp Lys Val Asp Lys Leu Thr Gly Leu Ser Ala Glu

GGA CAA AAG GCT CAG GAC TAT GTT TGT CGG TTA CCT CCA AGA ATT AGA AGG CTG    1136
Gly Gln Lys Ala Gln Asp Tyr Val Cys Arg Leu Pro Pro Arg Ile Arg Arg Leu

GAA GAG AGA GCT CAA GGA AGG GCA AAG GAA GCA CCC ACC ATG CCT TTC AGC TGG    1190
Glu Glu Arg Ala Gln Gly Arg Ala Lys Glu Ala Pro Thr MET Pro Phe Ser Trp

ATT TTC GAT AGG CAA GTG AAG CTG TAGGTGGCTA AAGTGCAGGA CGAAACCGAA ATGGTTAGTT    1254
Ile Phe Asp Arg Gln Val Lys Leu

TCACTCTTTT TCATGCCCAT CCCTGCAGAA TCAGAAGTAG AGGTAGAATT TTGTAGTTGC TTTTTTATTA    1324

CAAGTCCAGT TTAGTTTAAG GTCTGTGGAA GGGAGTTAGT TGAGGAGTGA ATTTAGTAAG TTGTAGATAC    1394

AGTTGTTTCT TGTGTTGTCA TGAGTATGCT GATAGAGAGC AGCTGTAGTT TTGTTGTTGT GTTCTTTTAT    1464

ATGGTCTCTT GTATGAGTTT CTTTTCTTTC CTTTTCTTCT TTCCTTTTCCT CTCTCTCTCT CTCTCTCTCT    1534

CTCTTTTTCT CTTATCCCAA GTGTCTCAAG TATAATAAGC AAACGATCCA TGTGGCAATT TTGATGATGG    1604

TGATCAGTCT CACAACTTGA TCTTTTGTCT TCTATTGGAA ACACAGCCTG CTTGTTTGAA AAAA    1668
```

FIGURE 3B
Page 3 of 3

1  TGAGAGATAGTGTGAGAGCATTAGCCTTAGAGAGAGAGAGAGAGCTTGTGTCTGAAAGAATCCACAA  69

HindIII
              ⎯⎯⎯⎯
70 ATGGCATTGAAGCTTAACCCCTTTGGCATCTCAGCCTTACAACTTCCCT 117
   METAlaLeuLysLeuAsnProLeuAlaSerGlnProTyrAsnPhePro

FIGURE 4A

```
                                                     PstI
                                                      |
  1  ACTTCATGGGCTATTTGGACAAGAGCTTGGACTGCAGAAGAGAACCGACACGGTGATCTTCTCAATAAG   69
     ThrSerTrpAlaIleTrpThrArgAlaTrpThrAlaGluGluAsnArgHisGlyAspLeuLeuAsnLys

70  TATCTTTACTTGTCTGGACGTGTTGACATGAGGCAGATTGAAAAGACCATTCAGTACTTGATTGGTTCT  138
     TyrLeuTyrLeuSerGlyArgValAspMETArgGlnIleGluLysThrIleGlnTyrLeuIleGlySer

BamHI
                   |
139  GGAATGGATCCTAGAACAGAGAACAATCCTTACCTCGG  176
     GlyMETAspProArgThrGluAsnAsnProTyrLeuAla
```

FIGURE 4B pCGN3235

TGAGAGATAG TGTGAGAGCA TTAGCCTTAG AGAGAGAGAG AGAGAGCTTG TGTCTGAAAG AATCCACAA

| ATG | GCA | TTG | AAG | CTT | AAC | CCT | TTG | GCA | TCT | CAG | CCT | TAC | AAC | TTC | CCT | TCC | TCG |
|---|---|---|---|---|---|---|---|---|---|---|---|---|---|---|---|---|---|
| MET | Ala | Leu | Lys | Leu | Asn | Pro | Leu | Ala | Ser | Gln | Pro | Tyr | Asn | Phe | Pro | Ser | Ser |

| GCT | CGT | CCG | CCA | ATC | TCT | TTC | ACT | TCT | AGA | TCT | CCC | AAG | TTC | CTC | TGC | CTC | GCT | TCT |
|---|---|---|---|---|---|---|---|---|---|---|---|---|---|---|---|---|---|---|
| Ala | Arg | Pro | Pro | Ile | Ser | Phe | Thr | Ser | Arg | Ser | Pro | Lys | Phe | Leu | Cys | Leu | Ala | Ser |

| TCT | TCT | CCC | GCT | CTC | AGC | TCC | AAG | GAG | GTT | GAG | AGT | TTG | AAG | CCA | TTC | ACA |
|---|---|---|---|---|---|---|---|---|---|---|---|---|---|---|---|---|
| Ser | Ser | Pro | Ala | Leu | Ser | Ser | Lys | Glu | Val | Glu | Ser | Leu | Lys | Pro | Phe | Thr |

| CCA | CCT | AAG | GAA | GTG | CAC | GTT | CAA | GTC | CTG | CAT | TCC | ATG | CCA | CCC | CAG | AAG | ATC |
|---|---|---|---|---|---|---|---|---|---|---|---|---|---|---|---|---|---|
| Pro | Pro | Lys | Glu | Val | His | Val | Gln | Val | Leu | His | Ser | MET | Pro | Pro | Gln | Lys | Ile |

| GAG | ATC | TTC | AAA | TCC | ATG | GAA | GAC | TGG | GCC | GAG | CAG | AAC | CTT | CTA | ACT | CAG | CTC |
|---|---|---|---|---|---|---|---|---|---|---|---|---|---|---|---|---|---|
| Glu | Ile | Phe | Lys | Ser | MET | Glu | Asp | Trp | Ala | Glu | Gln | Asn | Leu | Leu | Thr | Gln | Leu |

| AAA | GAC | GTG | GAG | GAG | TCG | AAG | CAG | GTT | AGA | GAG | CTA | AGA | GAG | TTC | CCC | GAC | CCT | GCA | TCC |
|---|---|---|---|---|---|---|---|---|---|---|---|---|---|---|---|---|---|---|---|
| Lys | Asp | Val | Glu | Glu | Ser | Trp | Gln | Val | Arg | Glu | Leu | Arg | Glu | Phe | Pro | Asp | Pro | Ala | Ser |

| GAT | GGG | TTC | GAA | GAT | CAG | GTT | AGA | GAG | CTA | AGA | GAG | GCA | AGA | GAG | CTC | CCT |
|---|---|---|---|---|---|---|---|---|---|---|---|---|---|---|---|---|
| Asp | Gly | Phe | Glu | Asp | Gln | Val | Arg | Glu | Leu | Arg | Glu | Ala | Arg | Glu | Leu | Pro |

| GAT | GAT | TAC | TTC | GTT | GTT | CTG | GTG | GGA | GAC | ATG | ATC | ACG | GAA | GAG | GCG | CTT | CCG |
|---|---|---|---|---|---|---|---|---|---|---|---|---|---|---|---|---|---|
| Asp | Asp | Tyr | Phe | Val | Val | Leu | Val | Gly | Asp | MET | Ile | Thr | Glu | Glu | Ala | Leu | Pro |

FIGURE 4C
Page 1 of 3

```
ACC TAT CAA ACC ATG TTG AAC ACT TTG GAT GGA GTG AGG GAT GAA ACT GGC GCT
Thr Tyr Gln Thr MET Leu Asn Thr Leu Asp Gly Val Arg Asp Glu Thr Gly Ala

AGC CCC ACT TCA TGG GCT ATT TGG ACA AGA GCT GCA GAA GAG AAC CGA
Ser Pro Thr Ser Trp Ala Ile Trp Thr Arg Ala Ala Glu Glu Asn Arg

CAC GGT GAT CTT CTC AAT AAG TAT CTT TAC TTG TCT GGA CGT GTT GAC ATG AGG
His Gly Asp Leu Leu Asn Lys Tyr Leu Tyr Leu Ser Gly Arg Val Asp MET Arg

CAG ATT GAA AAG ACC ATT CAG TAC TTG ATT GGT TCT GGA ATG TCT GGA CCT AGA ACA
Gln Ile Glu Lys Thr Ile Gln Tyr Leu Ile Gly Ser Gly MET Asp Pro Arg Thr

GAG AAC AAT CCT TAC CTC GGC TTC ATC TAC ACT TCA TTC TCA GAA AGA GCC ACC
Glu Asn Asn Pro Tyr Leu Gly Phe Ile Tyr Thr Ser Phe Ser Glu Arg Ala Thr

TTC ATC TCT CAC GGA AAC ACA GCC CAA CGC CAA GCC AAA GAG CAC GGA CAC CTC AAG
Phe Ile Ser His Gly Asn Thr Ala Arg Gln Ala Lys Glu His Gly Asp Leu Lys

CTA GCC CAA ATC TGC GGC ACA ATA GCT GCA GAC GAG CGT CAT GAG ACA GCT
Leu Ala Gln Ile Cys Gly Thr Ile Ala Asp Glu Lys Arg His Glu Thr Ala

TAC ACC AAG ATA GTT GAG AAG ATT GAG AAG CTC TTT GAT CCT GGT ACT GTG ATG
Tyr Thr Lys Ile Val Glu Lys Ile Glu Lys Leu Phe Asp Pro Gly Thr Val MET

GCG TTT GCA GAC ATG AGG AAA ATC TCG ATG CCT GCT CAC TTG ATG TAC
Ala Phe Ala Asp MET Arg Lys Ile Ser MET Pro Ala His Leu MET Tyr
```

FIGURE 4C
Page 2 of 3

```
GAT GGG CGG GAT GAA AGC CTC TTT GAC AAC TTC TCT TCT GTT GCT CAG AGG CTC
Asp Gly Arg Asp Glu Ser Leu Phe Asp Asn Phe Ser Ser Val Ala Gln Arg Leu

GGT GTT TAC ACT GCC AAA GAC TAT GCG GAC ATT CTT GAG TTT TTG GTT GGG AGG
Gly Val Tyr Thr Ala Lys Asp Tyr Ala Asp Ile Leu Glu Phe Leu Val Gly Arg

TGG AAG ATT GAG AGC TTG ACC GGG CTT TCA GGT GAA GGA AAC AAA GCG CAA GAG
Trp Lys Ile Glu Ser Leu Thr Gly Leu Ser Gly Glu Gly Asn Lys Ala Gln Glu

TAC TTG TGT GGG TTG ACT CCA AGA ATC AGG AGG TTG GAT GAG AGA GCT CAA GCA
Tyr Leu Cys Gly Leu Thr Pro Arg Ile Arg Arg Leu Asp Glu Arg Ala Gln Ala

AGA GCC AAG AAA GGA CCC AAG GTT CCT TTC AGC TGG ATA CAT GAC AGA GAA GTG
Arg Ala Lys Lys Gly Pro Lys Val Pro Phe Ser Trp Ile His Asp Arg Glu Val

CAG CTC TAA AAAGGAA CAAAGCTATG AAACCTTTTC ACTCTCCGTC GTCCCTCATT TGATCTATCT
Gln Leu *

GCTCTTGAAA TTGGTGTAGA TTACTATGGT TTGTGATATT GTTCGTGGGT CTAGTTACAA AGTTGAGAAG

CAGTGATTTA GTAGCTTTGT TGTTTCCAGT CTTTAAATGT TTTTGTGTTT GGTCCTTTTA GTAAACTTGT

TGTAGTTAAA TCAGTTGAAC TGTTTGGTCT GT
```

FIGURE 4C
Page 3 of 3

```
GAT GCC AAA ANG CCT CAC ATG CCT AGA GAA GCT CAT GTG CAA AAG   48
Asp Ala Lys Xaa Pro His MET Pro Arg Glu Ala His Val Gln Lys
 1               5                  10                  15

ACC CAT TCA ATK CCG CCT CAA AAG ATT GAG ATT TTC AAA TCC TTG GAG   96
Thr His Ser Xaa Pro Pro Gln Lys Ile Glu Ile Phe Lys Ser Leu Glu
                20                  25                  30

GGT TGG GCT GAG GAG AAT GTC TTG GTG CAT CTT AAA CCT GTG GAG AA   143
Gly Trp Ala Glu Glu Asn Val Leu Val His Leu Lys Pro Val Glu
         35                  40                  45
```

FIGURE 5

Amino Acid
Sequence From
Fragment F2    K   E   I   P   D   D   Y   FVVLVGDMITEEALPTY   Q   T   M   L   N   T AAA GAA AUU CCN GAU GAU UAU                      CAA ACN AUG CUN AAU AC/N
               G   G   C   C   C   C                                G               C
                       A Forward Primers:

5'GCTAAGCTT AAP GAP ATQ CCA GAQ GAQ TA3'   Desat 13-1
                       A CCG                Desat 13-2
                         CCC                Desat 13-3
                         CCT                Desat 13-4

Reverse Primers:
                                           (complements)

Desat 13-5a    3' GTQ TGN TAC GAN TTP TGCTTAAGCGA
                                           Desat 13-6a                     AAQ Oligonucleotides P = A or G
Q = T or C
N = A, C, T or C

FIGURE 6

```
TCTAGAATTC TCTAATTACG TCTGTTTGTT CTATTTTTTA TATGATATCA AATATTCGTC ATAAATATAT    70
GGTTTAAGAT GCCAAAAAAT TATTACTTG  GTGAATATAA TACGTTAAAT ATTAGAAATA CATCATTTAG   140
TTAAATAAAT AACCAAAAAC CAAAAATTCA TATCCGCGCT GGCGCGCGGT CAGGGTCTCG TTAGTTTTAA   210
AATCAATGCA GTTACAATT  AATTCCAGC  TGAAAATAAG TATAATTTGT ATTGAAATTA TAAAGTGACA   280
TTTTTTGTGT AACAAATATT TTGTGTAACA AGAATTAAAA AAAAAAACAG AAAATACTCA GCTTTTTTAA   350
TAATAAAAAA AATTAATTGA GTTAGAAAAT TGTTGTACCA ATAACAAAAG ATTTATATGG AATTATAAAA   420
TCAACACACC AATAACACAA GACTTTTTAA AAATTTAAGA ATAATATAAG CAATAACAAT AGAATCTTCA   490
AATTCTTCAA ATCCTTAAAA ATCAATCTCC CACTATTAAT CCCCCTTAGT TTTAGTTGGT AATGGCAACG   560
TTTGTTGACT ACCGTATTGT AACTTTTGTC AAATTGTCAT AAATACGTGT CAAACTCTGG TAAAAAATTA   630
GTCTGCTACA TCTGTCTTTT ATTTATAAAA CACAGCTGTT AATCAGAATT TGGTTTATTA AATCAACAAC   700
CTGCACGAAA CTTGTGTGAG CATATTTTGT CTGTTTCTGG TTCATGACCT TCTTCCGCAT GATGGCCAAG   770
TGTAATGGCC ACTTGCAAGA GCGTTTCTTC AACGAGATAA GTCGAACAAA TATTTGTCCG TTACGACCAC   840
ATATAAAAATC TCCCCATCTC TATATATAAT ACCAGCATTC ACCATCATGA ATACCTCAAA TCCCAATCTC   910
ACAAATACTT CAATAAAAAG ACCAAAAAAA ATTAAAGCAA AGAAAAGCCT TCTTGTGCAC AAAAAAAAAA   980
```

FIGURE 8
Page 1 of 4

```
GAAGCCTTCT AGGTTTTCAC GAC ATG AAG TTC ACT ACT CTA ATG GTC ATC ACA TTG      1036
                         MET Lys Phe Thr Thr Leu MET Val Ile Thr Leu

GTG ATA ATC GCC ATC TCG TCT CCT GTT CCA ATT AGA GCA ACC ACG GTT GAA AGT    1090
Val Ile Ile Ala Ile Ser Ser Pro Val Pro Ile Arg Ala Thr Thr Val Glu Ser

TTC GGA GAA GTG GCA CAA TCG TGT GTT GTG ACA GAA CTC GCC CCA TGC TTA CCA    1144
Phe Gly Glu Val Ala Gln Ser Cys Val Val Thr Glu Leu Ala Pro Cys Leu Pro

GCA ATG ACC ACG GGA GCA GGA GAC CCG ACT ACA GAA TGC TGC GAC AAA CTG GTA GAG  1198
Ala MET Thr Thr Gly Ala Gly Asp Pro Thr Thr Glu Cys Cys Asp Lys Leu Val Glu

CAG AAA CCA TGT CTT TGT GGT TAT ATT CGA AAC CCA GCC TAT AGT ATG TAT GTT    1252
Gln Lys Pro Cys Leu Cys Gly Tyr Ile Arg Asn Pro Ala Tyr Ser MET Tyr Val

ACT TCT CCA AAC GGT CGC TTA GAT TTT TGT AAG GTT CCT TTT CCT AGT            1306
Thr Ser Pro Asn Gly Arg Leu Asp Phe Cys Lys Val Pro Phe Pro Ser

TGT TAAATCTCTC AAGACATTGC TAAGAAAAAT ATTATTAAAA ATAAAAGAAT CAAACTAGAT      1369
Cys

CTGATGTAAC AATGAATCAT CATGTTATGG TTGAAGCTTA TATGCTGAAG TGTTTGATTT TATATATGTG  1439

TGTGTGTGTG TCCTGCTCAA TTTTGAAAC ACACACGTTT CTCCCTGATTT GGATTTAAAT TATATTTTGA  1509

GTTAAAAAAA AGAAAAAGAT GGAATGCTAT TTATACAAGT TGATGAAAAA GTGGAAGTAC AATTAGATA   1579
```

FIGURE 8
Page 2 of 4

```
TCTCCTACAC TTAAAGAATG AAACAATAAT AGACTTACGA AACAAATGAA AAATACATAA ATTGTCGACA  1649

ATCAACGTCC GATGACGAGT TTATTATTAA AAATTTGTGT GAAGGACTAG CAGTTCAACC AAATGATATT  1719

GAACATATAC ATCAACAAAT ATGATAATCA TAAAAGAGAG AATGGGGGGG GGGTGTCGTT TACCAGAAAC  1789

CTCTTTTTCT CAGCTCGCTA AAACCCTACC ACTAGAGACC TAGCTCTGAC CGTCGGCTCA TCGGTGCCGG  1859

AGGTGTAACC TTTCTTTCCC ATGACCCGAA ACCTCTCTTT CCCAACTCAC GAAAACCCTA CAATCAAAAA  1929

CCTAGCTCCG ACCGTCGGCT CATCGGTGCC GAAGGTGTAA CCTTTCTCTC CCATCATAGT TTCTCGTAAA  1999

TGAAAGCTAA TTGGGCAATC GATTTTTTAA TGTTTAAACC ATGCCAAGCC ATTTCTTATA GGACAATTGT  2069

CAATAATAGC ATCTTTTGAG TTTTGTCTCA AAAGTGACAC TAGAAGAAAA AAGTCACAAA AATGACATTC  2139

ATTAAAAAGT AAAATATCCC TAATACCTTT GGTTTAAATT AAATAAGTAA ACAAAAATAA ATAAAAACAA  2209

ATAAAATAAA AATAAAAAAT GAAAAAAAGA AATTTTTTTA TAGTTTCAGA TTATATGTTT TCAGATTCGA  2279

AATTTTTTAA ATTCCCTTTT TTAAATTTTC TTTTTTGAAA TTTTTTTTTT TGAAATTTTT TGAAACTGTT  2349

TTTAAAATTT TTATTTTAA TTTTTTAGTA TTTATTTTTT ATTTTATAAA ATTTTAAACG CTAATTCCAA  2419

AACTCCCCCC CCCCCCCCCC CCCCAATTCT CTCCTAGTCT TTTTCTCTTT CTTATATTTG GGCTTCTATC  2489

TTCTCTTTTT TTTTCAGGCC CAAAGTATCA TGTGTAACAA CCGGTGTTCA AAAACGCGCC CGCCTGGCCG  2559
```

FIGURE 8
Page 3 of 4

```
TTTACTCGCC CGATTAAATG ATGATCGGAA GGCTGCCATG GCGAGGCGGA GGTAATCAGT GGTTCTAGGC  2629
GCTGAAACTA GAAAACCTTC AAAAATCGAA ATTTTAAGAG CTAAATCGGT GTTTATCTCA TGAATCTATT  2699
ATATTTAGTT GAAACTCACA AGAATCGGTT GTAAAAACTA TGAAATCGTG CAAAAAAAAT GAAGAACAAA  2769
ATATTCTCAG ATCTGGAAAA CACAGAGAAG AGGTTGAAGA TGAGGGTAAA ATCGTATTTT GTCATTCATT  2839
AAACTAAAAT CAAAAAAAAA TGATGCAAAA TTCAATGATA ATAACTCGAA CTCGCAACCA TATGCATCTT  2909
TAGACTGCGA CACGGACCAC TAGACTAAGC AATTTTAATG TTTATTCATC ACAGACCTAA TATATGTCTA  2979
AAACTAGGCG CCGAGTACGC CCCGCTTAAT CCCGAGTTTT TGTTAGCTCG CTAGACCCAG GGTCACCGCC  3049
CGACTAACGA GTAGCGTAAT TCTGAACTGG GGTAACAACA TAGAGAACAT CGCCGACCCT TCCCTGCCGA  3119
TGATGCCGCC TCCGATGAAC TTCCTGTAAC GCCTTCAGTT TCCATTGATT TTCCCCTTTA ATCTGATCAG  3189
TTCCATGTTT TATCCAACTC ATCCCACTCC GTAGCATTTA ATCGATCTCA TCATTTACAT ACATAACCAG  3259
TAGGAGGTCT CATATAAATT TGAACGTTTC CAGCGATGAA CAGTGCCAAT CTCTGCGAAA TCCATTCTC   3329
TAAGCTCAGG GCTGGGCGGCT GCAGCCCGGG GATCCACTAG TTCTAGGCGG CCGCACCGCG GTGGAGCTCC  3399
AATTCGCCCT ATAGTGAGTC GTATTACGCG CGCTCACTGG C                                3440
```

FIGURE 8
Page 4 of 4

```
     XhoI
     |
   1 CTCGAGAGCTGAAGGATTTTTTGTTAGAGATTCAACGACACAGATGGACCCTTCCTCCACTAGGCAACTGC    69

70 AAGAACCTAACAATGCAAATATCACTCCTCCTCAGCCTTCAAGGAGCGTTAATAGGACTGGAACAAGCG   138
                           BglII
                           |
 139 GTCAAGTGAGTAAATTTCCTTCCAAGAGATCTCTATGGTTCGGTTCATGAAGTTTGTGGTTTAATT      207
                           169
 208 GTGTAGCAACAGGATAGTGCAAGTGAGAATAGAGTTCGACCTCATCTACCTACCCCGAACCTCTGAAT   276

277 GTATCCCCATTGAAGAAGAGGGCAAATCCTGCACCCAGAAGGATAAAGAAATTTGGACGCCTGAA      345

346 GAAGTGGCAGTTCTGAGGGAAGGAGTAAAAGAGTATGTCTACTACTACTCTATAATCAAGTTTCAA     414

415 GAAGCTGAGCTTGGCTCTCACTTTATATGTTTGATGTTGTTGTGCAGTATGGTAAATCATGGAAAGAG   483

484 ATAAAGAATGCAAACCCTGAAGTATTGCGAATTGTAAGTGGTACTAAAAGGTTTGTAACTTTTGTGTTA   552

553 CTCATCTGAATTATCTTATATGCGAAGTGGTAGCCGGTAACAAGTTTTATATTGCTATGAAGTTTTTTG  621

622 TTGAAGGATAAATGGAGGAACTTGCTTCGGTAGCCGGTAACAAGTTTTAGAAAGGTCTTTTCACATTTGTGTTTG  690

691 CCTGCGTGACGTATCAGCAGCTGTGGAGAAGATGGTATTAGAAAGGTCTTTTCACATTTGTGTTGTG   759
```

FIGURE 9
Page 1 of 6

760  ACAAATATTAATTCGGCCGGTATGGTTGGTTAAGACTTGTTGAGAGACGTGTGGGGTTTTTGATGTA  828
829  TAATTAGTCTGTGTTTAGAACGAAACAAGACTTGTTGCGTATGCTTTTTTTAACTTGAGGGGTTTGTT  897
                                                 BglII
                                                  |
898  GTTGTTAGTTAGGAACTTGACTTTGTCTCTTTCTCTCAAGATCTGATTGGTAAGGTCTGGGTGGTAGTA  966
                                            937
967  CTGTTTGGTTAATTTGTTTTGACTATTGAGTCACTGTGGCCCATTGACTTTAAATTAGGCTGGTATAT  1035
1036 TTTTTGGTTTAAAACCGGTCTGAGATAGTGCAATTTCGATTCAGTCAATTTTAAATTCTTCAAGGTAAT  1104
1105 GGGCTGAATACTTGTATAGTTTTAAGACTTAACAGGCCCATGTTATCATAAAACGTTATCATAAAACGTCAT  1173
                      HindIII
                         |
1174 TGTTTAGAGTGCACCAAGCTTATAAAATGTAGCCAGGCCTTAAAAGACTTAACAGGCCTTAAAAGACTT  1242
                      1190
1243 AACATTCCTTAAAAGGCCCATGTTATCATAAAACGTCATCGTTTGAGTGCACCAAGCTAAATGTAGCC  1311
1312 AGGCCCTAAAAGACTTAACAGGCCTTAAAAGGCCCATGTTATCATAAAACGCCGTCGTTTTGAGTGCAC  1380

FIGURE 9
Page 2 of 6

```
          HindIII
            |
1381  CAAGCTTATAAATGTAGCCAGCTACCTCGGGACATCACGCTCTTTGTACACTCCGCCATCTCTCTCT  1449

XhoI BglII                           SalI
          |   |                                |
1450  CTCGAGCAGATCTCTCTCGGGAATATGTCGACAATGTCGACCACTTTCTGCTCTTCCGTCTCCATGCAAGC  1518
        1451 1458                            1484

1519  CACTTCTCTGGTAATCTCATCTCCTTCTTGTGTTCCCAGATCGCTCTGATCATACTTTCTTTTAGATCA  1587

1588  TTTGCCTCTGATCTGTTGCTTGATGTTTGTTAACTCTCCACGCATGTTGATTATGTTGAGAATTAGAA  1656

1657  AAAAAATGTTAGCTTTACGAATCTTTAGTGATGATCATTTCAATTGGATTTGCAATCTTGTGTGACATTGA  1725

1726  GGCTTGTGTAGATTCGATCTGTATTCATTTGAATCACAGCTATAATAGTCATTTGAGTAGTAGTGTT  1794

1795  TTTAAATGAACATGTTTGTTGTATTGATGGAACAAACAGGCAGCAACAACGAGGATTAGTTTCCAGAA  1863

1864  GCCAGCTTTGGTTTCAACGACTAATCTCTCCCTTCAACCTCCGCCGTTCAATCCCCACTCGTTTCTCAAT  1932

1933  CTCCTGCGCGGTATGTTCTCATTCTCCAGCATTATTCGAGCTTGCTTGTCATGGTACTCTCTCTAATT  2001

2002  GTCTATTTGGTTTATTAGGCCAAACCAGAGACGGTTGAGAAAGTGTCTAAGATAGTTAAGAAGCAGCTA  2070
```

FIGURE 9
Page 3 of 6

```
2071  TCACTCAAAGACGACCAAAAGGTCGTTGCGGAGACCAAGTTTGCTGATCTTGGAGCAGATTCTCTCGAC  2139
2140  ACTGTAAGTCATCAATCATTCTCTTATGTGAATAAAGAGAACTTGAAGAGTTTGTTTTTAACATATTAA  2208
                                                        EcoRV
                                                          |
2209  CTGAGTGTTTTGCATGCAGGTTGAGATAGTGATGGGTTTAGAGGAAGAGTTTGATATCGAAATGGCTGA  2277
                                                                  2264
                                                                         SstI
                                                                          |
2278  AGAGAAAGCTCAGAAGATTGCTACTGTGGAGGAAGCTGCTGAACTCATTGAAGAGCTCGTTCAACTTAA  2346
                                                                  2335
2347  GAAGTAATTTTAGTATTAAGAGCAGCCAAGCTTTGTTGGGTTTGTGTTTCATAATCTTCCTGTCAT    2415
2416  TTTCTTTTTCTTAATGTGTCAAGCGACTCTCGTTGGTTTAAAGTAGTATCTGTTTGCCATGGATCTCTC 2484
                                                  HindIII
                                                    |
2485  TCTATTTGTCGACTGAAAACTTTGGTTTACACATGAAAGCTTGTTCTGTTCTTTCTTAAATCGAAAT   2553
        SalI                                        2523
         |
       2493
2554  GCCAAATGCGAGATTAGGGAATCTTGTATTAACACATAAGTCAAAGAGTAGGCCCTAAGATGACA     2622
2623  ATTTATAAACAATCCTATTCACATTGTATATACAGGTTATGATTATTCCCAATCAGCGTCAAAGAATCC 2691
```

FIGURE 9
Page 4 of 6

```
2692 AGCATCTTTCATCTCTGAATAGTAGACATTCTCCAAGTTCACATCTTCCTCCTGCACCAAAAACCAGTA 2760
2761 CTAAATCATGAACATTGCAATAATCACATGCCTAGGCGAGAGTTTGGTGATGTGGTGTTAGTGATAGT 2829
2830 GATACTGATGGTGCTAGAGCGGTTAAGAAGGATTAACCTGGAAGAAGTCTGCAAGGAAAGTAACATAGA 2898
2899 GAAGAGGAAGATAGGAGTGGTAACAAAACACTTGTGATCCCATACAGCCTCCCAGCATTTTCAAATGTT 2967
2968 ATTTCCTTACATAAAGAAACAAGAGAAGTCTGACTAGATGATATTTATATAGGATAAGTGTTTTACCAT 3036
3037 AAGCCAAAGTGAGCGCCGTTTGCAAGAGCTAACCAGACAGTACACGTTGGCATATATCTCATCAACAT 3105
3106 GATCTGAAAAGTAACATATCACAGTTAATGAACACAATGGTTACCTTGAGAAGCAAATCAAGACCTATA 3174
3175 ACAAGCCCAGAGATGAGGAAAGTCCGTGTCAACGCTTCACCGCCATTCGCGTAGTTCCTTGGAAGACA 3243
3244 AAGGCCACCAACCAAACTTACTTCCAGAAACAACACTCCAAATGTTGTCAACAAGTCAATAGATTCCA 3312
3313 AACTACTTCGTTACAGGGTTGTATAGATAATAGTTTATATAATATCGGGGCGTATATAAAGTATAAAGAAACTCTTCTC 3381
```



```
2692 AGCATCTTTCATCTCTGAATAGTAGACATTCTCCAAGTTCACATCTTCCTCCTGCACCAAAAACCAGTA 2760
2761 CTAAATCATGAACATTGCAATAATCACATGCCTAGGCGAGAGTTTGGTGATGTGGTGTTAGTGATAGT 2829
2830 GATACTGATGGTGCTAGAGCGGTTAAGAAGGATTAACCTGGAAGAAGTCTGCAAGGAAAGTAACATAGA 2898
2899 GAAGAGGAAGATAGGAGTGGTAACAAAACACTTGTGATCCCATACAGCCTCCCAGCATTTTCAAATGTT 2967
2968 ATTTCCTTACATAAAGAAACAAGAGAAGTCTGACTAGATGATATTTATATAGGATAAGTGTTTTACCAT 3036
3037 AAGCCAAAGTGAGCGCCGTTTGCAAGAGCTAACCAGACAGTACACGTTGGCATATATCTCATCAACAT 3105
3106 GATCTGAAAAGTAACATATCACAGTTAATGAACACAATGGTTACCTTGAGAAGCAAATCAAGACCTATA 3174
3175 ACAAGCCCAGAGATGAGGAAAGTCCGTGTCAACGCTTCACCGCCATTCGCGTAGTTCCTTGGAAGACA 3243
3244 AAGGCCACCAACCAAACTTACTTCCAGAAACAACACTCCAAATGTTGTCAACAAGTCAATAGATTCCA 3312
3313 AACTACTTCGTTACAGGGTTGTATAGATAATAGTTTATATAATATCGGGGCGTATATAAAGTATAAATAAA 3381
3382 TAAAAGATCCTATCGGTAAATAGTTTATAATAATATCGGGGCGTATATAAAGTATAAAAGAAACTCTTCTC 3450
3451 CAATCCGACCGTTGAAAATCACTCTCAATCTCTGGCCTAACGACCGGATCGTTCGCGCGTAATTTTCGC 3519
3520 TGCTATAAATAGAAACTTTCCTCTTCCTCTTCTCGTTTCTCGATCAAAATTTTTTTTGGAAAAATTAAGTTTGAA 3588
```

FIGURE 9
Page 5 of 6

```
3589  TCTATCGTAGATGCTGTGACAAAAAAAAATTGTTTTATCGAAGATGAGAAACATGAGGCCTGTTCATGC  3657
                                BamHI

3658  AAGGAACCAGACCACGGATCCATCTTCGCCGATGATGACGTCTCCTCTGATGAATCGTCACGCACGGAC  3726
                      BamHI
                      3674

3727  AGGATCCAACGCTGGACCAGCATCTAACGCCAAGAAAGCACAGACGCAAAGCAGCTCAGAGACTCGC    3795
      BamHI
      3729

3796  GGCTGTGATGTCGAACCAAACAGGCGACGATGAAGACAGTGATGATGACCTTTCCTTTGACTACAACGC  3864

3865  TGTCGGAAGCATTGGTCTCTCGCTGCCGGAAGATCT  3898
                                    BglII
                                    3894
```

FIGURE 9
Page 6 of 6

Lambda CGN1-2

NCG-186 Linear          LENGTH = 4325

```
                              SduI
                              NlaIV
           XhoI               HgiJII     HindIII
           AvaI                 |           |
             |                  |           |
    1 CTCGAGGCAGTCACTAACATGAAGTTTGACGAGGAGCCCAACTATGGGAAGCTTATTTCTCTTTTCGAT  69
      2                                    39         50

XbaI                                              SacI
              |                                                 |
   70 ACTCTAATTGAGCCGTGCGCTCTATCTAGACCAATTAGAATTGATGGAGCTCTAAAGGTTGCTGGCTGT  138
                         95                                    121

NdeI                         SspI                    NdeI
                |                            |                       |
  139 TTTCTTGTTCATATGATTAACTTCTAAACTTGTGTATAAATATTCTCTGAAAGTGCTTCTTTTGGCATA  207
                150                         180                     206

Ksp632I
                                       |
  208 TGTAGGTTGGGCAAAAACGAGGAAGATTGCTTCTCAATTGGAAGAGGATGAACAGCCGAAGAAGAAAA   276
                                      245
```

FIGURE 10
Page 1 of 13

```
                                                     XhoII
                                                      |
277 TAAGAATAGGCAGTCCTGCTACTCAATGGATCTCCAGTCTATAACGGTCGTGTCCCATGAAACAGAGGT  345
                                                     305

MmeI   EcoRV
                                                         |      |
346 AAAACATTTTTTGCATATACACTTTGAAAGTTCCCTCACTAACTGTGTAATCTTTTGGTAGATATCACTA  414
                                                        401    408

SduI
                        MstI                              HaeI
                       BclI HgiAI                          |
                        | |  |
415 CAATGTCGGAGAGACAA3GGCTGMNCANCATATACAAAAGGGAAATGAAGATGGCCTTTTGATTAGCTG  483
                       437 442                            469
                        439

SduI
                                   HgiJII
                                    |
484 TGTAGCATCAGCAGCTAAATCTCTGGGCTCTCATCATGGATGCTGGAACTGGATTCACTTCTCAAGTTTA  552
                                   512
```

FIGURE 10
Page 2 of 13

```
                 Cfr10I
                 BbvII
                 | |
553  TGAGTTGTCACCGGTCTTCCTACACAAGGTAATAATCAGTTGAAGCAATTAAGAATCAATTTGATTTGT   621
                 560
                 563

622  AGTAAACTAAGAAGAATTACCTTATGTTTTCCCCGCAGGACTGGATTATGGAACAATGGGAAAAGAAC    690

SacI
                                          |
691  TACTATATAAGCTCCATAGCTGGTTCAGATAACGGGAGCTCTTTAGTTGTTATGTCAAAAGGTTAGTGT  759
                                          731

BbvII
                                |
760  TTAGTGAATAATAAACTTATACCACAAAGTCTTCATTGACTTATTTATATACTGTGTTGTGAATTGCTAG 828
                                782

829  GAACTACTTATTCTCAGCAGTCATACAAAGTGAGTGACTCATTCCGTTCAAGTGGATAAATAAGAAAT   897

898  GGAAAGAAGATTTCATGTAACCTCCATGACAACTGCTGGTAATCGTTGGGGTGTGGTAATGTCGAGGA   966
                        BclI
                        |
967  ACTCTGGCTTCTCTGATCAGGTAGGTTTTTGTCTCTTATTGTCTGGTGTTTTATTTTCCCCTGATAGT  1035
                        981
```

FIGURE 10
Page 3 of 13

```
1036 CTAATATGATAAACTCTGCGTTGTGAAAGGTGGTGGAGCTTGACTTTTTGTACCCAAGCGATGGGATAC 1104
1105 ATAGGAGGTGGGAGAATGGGTATAGAATAACATCAATGGCAGCAACTGCGCGATCAAGCAGCTTTCATAT 1173
                    Tth111II                                  ScaI
                       |                                        |
1174 TAAGCATACCAAAGCCGTAAGATGGTGGATGAAACTCAAGAGACTCTCCGCACCACCGCCTTTCCAAGTA 1242
            1175                                                         1242
                                                   XhoII
                                                     |
1243 CTCATGTCAAGGTTGGTTTCTTTAGCTTTGAACACAGATTTGGATCTTTTTGTTTTGTTTCCATATACT 1311
                                                   1285
1312 TAGGACCTGAGAGCTTTTGGTTGATTTTTTTTCAGGACAAATGGGCGAAGAATCTGTACATTGCATCA 1380
                                              AflII
                                                |
1381 ATATGCTATGGCAGGACAGTGTGCTGATACACACTTAAGCATCATGTGGAAAGCCAAAGACAATTGGAG 1449
                                                 1415
1450 CGAGACTCAGGGTCGTCATAATACCAATCAAAGACGTAAAACCAGACGCAACCTCTTTGGTTGAATGTA 1518
                                                                SspI
                                                                  |
1519 ATGAAAGGGATGTGTCTTGGTATGTATGTACGAATAACAAAAGAGAAGATGGAATTAGTAGTAGAAATA 1587
                                                                       1587
```

FIGURE 10
Page 4 of 13

```
                                                           EcoRV
                                                             |
1588  TTTGGGAGCTTTTTAAGCCCTTCAAGTGTGCTTTTTATCTTATTGATATCATCCATTTGCGTTGTTTAA  1656
                                                            1635

XbaI
            |
1657  TGCGTCTCTAGATATGTTCCTATATCTTTCTCAGTGTCTGATAAGTGAAATGTGAGAAAACCATACCAA  1725
           1664

SspI
            |
1726  ACCAAAAATATTCAAATCTTATTTTTAATAATGTTGAATCACTCGGAGTTGCCACCTTCTGTGCCAATTG  1794
                1734                                                    1789

EcoRI
                                                                           |
1795  TGCTGAATCTATCACACTAGAAAAAAACATTCTTCAAGGTAATGACTTGTGGACTATGTTCTGAATTC  1863
                                                                         1859

Eco57I
                      |
1864  TCATTAAGTTTTTATTTCTGAAGTTTAAGTTTTTACCTTCTGTGTTTTGAAATATATCGTTCATAAGATG  1932
                    1904
```

FIGURE 10
Page 5 of 13

```
                                                   SphI
                                                   NspI
                                                   |
1933 TCACGCCAGGACATGAGCTACACATCGCACATAGCATGCAGATCAGGACGATTTGTCACTCACTTCAAA 2001
                                                           1971

SphI
                            NdeI      NspI      PmaCI
                            [AvaIII]  SspI AflIII
                            |         |  |  |
2002 CACCTAAGAGAGCTTCTCTCTCACAGCGCACACACATATGCATGCAATATTTACACGTGATCGCCATGCAA 2070
     |                                     |    |  |                 |
     Tth111I                              2036 2044               2056
     2015                                    2037 2048 2053

SecI
                  |
2071 ATCTCCATTCTCCACCTATAAATTAGAGCCTCGGCTTCACTCTTTACTCAAACCAAAACTCATCACTACA 2139
                                 2099

Ksp632I
                                |
2140 GAACATACACAAATGGCGAACAAGCTCTTCCTCGTCCTCGGCAACTCTCGCCTTGTTCTTCCTTCTCACC 2208
                       METAlaAsnLysLeuPheLeuValSerAlaThrLeuAlaLeuPheLeuLeuThr
                          2171
```

FIGURE 10
Page 6 of 13

Page 7 of 13

```
2485 CAGGAAGAGCCACTTTGCGTTTGCCCAACCTTGAAAGGAGCATCCAAAGCCGTTAAACAACAGATTCGA 2553
     GlnGluProLeuCysValCysProThrLeuLysGlyAlaSerLysAlaValLysGlnIleArg

2554 CAACAACAGGGACAACAAATGCAGGAGACAGCAGATGCAGCAAGTGATTAGCCGTATCTACCAGACCGCT 2622
     GlnGlnGlnGlyGlnGlnMETGlnGlyGlnMETGlnGlyGlnValIleSerArgIleTyrGlnThrAla
                                                                SecI
                                                                BbvII
                                                                 |

2623 ACGCCACTTACCTAGAGCTTGCAACATCAGGCAAGTTAGCATTGCCCCTTCCAGAAGACCATGCCTGGG 2691
     ThrHisLeuProArgAlaCysAsnIleArgGlnValSerIleCysProPheGlnLysThrMETProGly
                                                                    2684
                                                                    2687

XhoI       SecI
                            AvaI       DsaI
                            |          AccI
                            |          |
2692 CCCGGCTTCTACTAGATTCCAAACGAATATCCTCGAGAGTGTGTATACCACGGTGATATGAGTGTGGTT 2760
     ProGlyPheTyr
     2694                        2724        2736
     2692                                    2740

HpaI
            HindII
            |
2761 GTTGATGTATGTTAACACTACATAGTCATGGTGTGTGTTCCATAAATAATGTACTAATGTAATAAGAAC 2829
                    2774
```

FIGURE 10
Page 8 of 13

Page 9 of 13

```
                                                       BbvII                                     Tth111
                                                         |                                         |
3106 TTATGCAAGTGTTCTTTTATTTGGTGAAGACTCTTTAGAAGCAAAGAACGACAAGCAGTAATAAAAAAA  3174
                                                       3139                                     3174

VspI
                                                                        |
3175 ACAAAGTTCAGTTTTTAAGATTTGTTATTGACTTATTGTCATTTGAAAAATATAGTATGATATTAATATA  3243
                                                                      3237

Tth111II                     VspI
                 |                           |
3244 GTTTTATTTATATAATGCTTGTCTATTCAAGATTTGAGAACATTAATATGATACTGTCCACATATCCAA  3312
               3250                        3287

NdeI    Tth111II
                                           |        |
3313 TATATTAAGTTTCATTTCTGTTCAAACATGATAAGATGGTCAAAATGATTATGAGTTTTGTTATTTAC  3381
                                         3341    3352

Eco57I                                    Eco57I
                |                                         |
3382 CTGAAGAAAAGATAAGTGAGCTTCGAGTTTCTGAAGGGTACGTGATCTTCATTTCTTGGCTAAAAGCGA  3450
                3404                                    3434

3451 ATATGACATCACCTAGAGAAAGCCGATAATAGTAAACTCTGTTCTTGGTTTTTGGTTTAATCAAACCGA  3519
```

FIGURE 10
Page 10 of 13

```
                                        Tth111II
                                        NdeI
                                        ||
          Cfr10I
          |
     ACCGGTAGCTGAGTGTCAAGTCAGCAAACATCGCAAACCATATGTCAATTCGTTAGATTCCCGGTTTAA 3588
3520                                              3560
                                                  3561

Cfr10I
            |
3589 GTTGTAAACCGGTATTTCATTTGGTGAAAACCCTAGAAGCCAGCCANCCTTTTTAATCTAATTTTGCA 3657
                 3597

NlaIV
                                                   HindCI
                                                   HgiCI
                                                   BspHI
                                                   |||
3658 AACGAGAAGTCACCACACCCTCTCCACTAAAAACCCTGAACCTTACTGAGAGAAGCAGAGNCANNAAAGAA 3726
                                                            3717
                                                          3716
                                                            3718

Eco31I         PmaCI                      Ksp632I
            |              |                          |
3727 CAAATAAAAACCCGAAGATGAGACCACCACGTGCGGGACGTTCAGGGGACGGGGAGGAAGAGAATGR 3795
                  3740         3756                      3781

3796 CGGCGG5MNTTTGGTGGGCGGCGGACGTTTTGGTGGCGGCGGTGGACGTTTGGTGGCGGCGGTGGA 3864
```

FIGURE 10

```
                  EcoRV
                   |
3865 CCTTTGGTGGTGGATATCGTGACGAAGGACCTCCCAGTGAAGTCATTGGTTCGTTTACTCTTTCTTAG 3933
                                                  HindIII
                                                  AflII
                                                    |
3934 TCGAATCTTATTCTGCTCTGCTCGTTGTTTACCGATAAAGCTTAAGACTTTATTGATAAAGTTCTCA 4002
                                                  3977
                                               3974

4003 GCTTTGAATGTGAATGAACTGTTTCCTGCTTATTAGTGTTCCTTTGTTTTGAGTTGAATCACTGTCTTA 4071

4072 GCACTTTTGTTAGATTCATCTTTGTGTTTAAGTTAAAAGGTAGAAACTTTGTGACTTGTCTCCGTTATG 4140
           HpaI                                Tth111I
           HindII                                |
4141 ACAAGGTTAACTTTGTTGGTTATAACAGAAGTTGCGACCTTTCTCCATGCTTGTGAGGGTGATGCTGTG 4209
           4149                               4179
                  XhoII
                    |
4210 GACCAAGCTCTCTCAGGCGAAGATCCCTTACTTCAATGCCCCAATCTACTTGGAAAACAAGACACAGAT 4278
                  4231
```

FIGURE 10
Page 12 of 13

```
                                              SalI
                                              PstI         HindII
                                  HindIII     AccI EcoRI
                    XhoII  BspMI                | | |
                     |       |                  | | |
4279 TGGGAAAGTTGATGAGATCCAAGCTTGGGCTGCAGGTCGACGAATTC 4325
         4294   4300                    4316 4321
                  4302                  4317
                                     4313
                                        4315
```

FIGURE 10
Page 13 of 13

PLANT DESATURASES—COMPOSITIONS AND USES

This application is a divisional application of application Ser. No. 07/762,762, filed Sep. 16, 1991, issued as U.S. Pat. No. 7,037,692, which is a continuation-in-part of PCT/US91/01746 filed Mar. 14, 1991, now expired, and a continuation-in-part of U.S. Ser. No. 07/494,106 filed on Mar. 16, 1990, now abandoned, and a continuation-in-part of U.S. Ser. No. 07/615,784 filed on Nov. 14, 1990, now abandoned, which is a continuation-in-part of U.S. Ser. No. 07/567,373 filed on Aug. 13, 1990, now abandoned, and a continuation-in-part of the above-referenced U.S. Ser. No. 07/494,106.

TECHNICAL FIELD

The present invention is directed to desaturase enzymes relevant to fatty acid synthesis in plants, enzymes, amino acid and nucleic acid sequences and methods related thereto, and novel plant entities and/or oils and methods related thereto.

INTRODUCTION

Background

Novel vegetable oils compositions and/or improved means to obtain or manipulate fatty acid compositions, from biosynthetic or natural plant sources, are needed. Depending upon the intended oil use, various different oil compositions are desired. For example, edible oil sources containing the minimum possible amounts of saturates, palmitate (C16:0) and stearate (C18:0) saturated fatty acids, are desired for dietary reasons and alternatives to current sources of highly saturated oil products, such as tropical oils, are also needed.

One means postulated to obtain such oils and/or modified fatty acid compositions is through the genetic engineering of plants. The fatty acid composition of major oilseeds ordered here by palmitate content, is shown in Table I. With the exception of laurate (C12:0) sources of coconut endosperm and palm kernel, the common edible oils all basically consist of 16:0, 18:0, 18:1 (oleate), 18:2 (linoleate), and 18:3 (linolenate).

TABLE I

| | 12:0 | 14:0 | 16:0 | 18:0 | 18:1 | 18:2 | 18:3 | 20:1 | 22:1 |
|---|---|---|---|---|---|---|---|---|---|
| rape (HEAR) | | | 3 | 0.8 | 9.9 | 13.5 | 9.8 | 6.8 | 53.6 |
| rape (LEAR) | | | 4.9 | 1.4 | 56.4 | 24.2 | 10.5 | | |
| sunflower | | 0.1 | 5.8 | 5.2 | 16 | 71.5 | 0.2 | | |
| peanut | | | 6.7 | 4.3 | 71.4 | 11.1 | | 6.5 | |
| safflower | | | 7.6 | 2 | 10.8 | 79.6 | | | |
| coconut | 40.2 | 15.5 | 7.6 | 2.4 | 5.2 | 1.2 | | | |
| oil palm kernel | 50.9 | 18.4 | 8.7 | 1.9 | 14.6 | 1.2 | | | |
| soybean | | | 15.3 | 3.8 | 20.7 | 55.8 | 9.4 | | |
| cotton | | 1 | 23.4 | 2.5 | 17.9 | 54.2 | | | |
| oil palm mesocarp | 0.1 | 1.2 | 46.8 | 3.8 | 37.6 | | | | |

However, in order to genetically engineer plants one must have in place the means to transfer genetic material to the plant in a stable and heritable manner. Additionally, one must have nucleic acid sequences capable of producing the desired phenotypic result, regulatory regions capable of directing the correct application of such sequences, and the like. Moreover, it should be appreciated that to produce a desired modified oils phenotype requires that the Fatty Acid Synthase (FAS) pathway of the plant is modified to the extent that the ratios of reactants are modulated or changed.

Higher plants appear to synthesize fatty acids via a common metabolic pathway in plant plastid organelles (i.e., chloroplasts, proplastids, or other related organelles) as part of the FAS complex. (By fatty acid is meant free fatty acids and acyl-fatty acid groups.) Outside of plastid organelles, fatty acids are incorporated into triacylglycerols (triglycerides) and used in plant membranes and in neutral lipids. In developing seeds, where oils are produced and stored as sources of energy for future use, FAS occurs in proplastids.

The production of fatty acids begins in the plastid with the reaction between Acyl Carrier Protein (ACP) and acetyl-CoA to produce acetyl-ACP. Through a sequence of cyclical reactions, the acetyl-ACP is elongated to 16- and 18-carbon fatty acids. The longest chain fatty acids produced by the FAS are 18 carbons long. Monounsaturated fatty acids are also produced in the plastid through the action of a desaturase enzyme.

Common plant fatty acids, such as oleic, linoleic and α-linolenic acids, are the result of sequential desaturation of stearate. The first desaturation step is the desaturation of stearoyl-ACP (C18:0) to form oleoyl-ACP (C18:1) in a reaction often catalyzed by a Δ-9 desaturase, also often referred to as a "stearoyl-ACP desaturase" because of its high activity toward stearate the 18 carbon acyl-ACP. The desaturase enzyme functions to add a double bond at the ninth carbon in accordance with the following reaction (I):

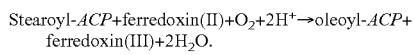
Stearoyl-*ACP*+ferredoxin(II)+$O_2$+2H$^+$→oleoyl-*ACP*+ ferredoxin(III)+2H$_2$O.

Δ-9 desaturases have been studied in partially purified preparations from numerous plant species. Reports indicate that the protein is a dimer, perhaps a homodimer, displaying a molecular weight of 68 kD (±8 kD) by gel-filtration and a molecular weight of 36 kD by SDS-polyacrylamide gel electrophoresis.

In subsequent sequential steps for triglyceride production, polyunsaturated fatty acids may be produced. These desaturations occur outside of the plastid as a result of the action of membrane-bound enzymes. Additional double bonds are added at the twelve position carbon and thereafter, if added, at the 15 position carbon through the action of Δ-12 desaturase and Δ-15 desaturase, respectively.

The fatty acid composition of a plant cell is a reflection of the free fatty acid pool and the fatty acids (fatty acyl groups) incorporated into triglycerides. Thus, in a triglyceride molecule, represented as

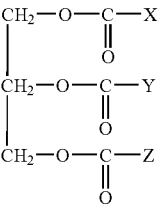

Formula (I)

X, Y, and Z each represent fatty acids which may be the same or different from one another. Various combinations of fatty acids in the different positions in the triglyceride will alter the properties of triglyceride. For example, if the fatty acyl groups are mostly saturated fatty acids, then the triglyceride will be solid at room temperature. In general, however, vegetable oils tend to be mixtures of different triglycerides. The triglyceride oil properties are therefore a result of the combination of triglycerides which make up the oil, which are in turn influenced by their respective fatty acid compositions.

For example, cocoa-butter has certain desirable qualities (mouth feel, sharp melting point, etc.) which are a function of its triglyceride composition. Cocoa-butter contains approximately 24.4% palmitate (16:0), 34.5% stearate (18:0), 39.1% oleate (18:1) and 2% linoleate (18:2). Thus, in cocoa butter,. palmitate-oleate-stearate (POS) (i.e., X, Y and Z, respectively, in Formula I) comprises almost 50% of triglyceride composition, with stearate-oleate-stearate (SOS) and palmitate-oleate-palmitate (POP) comprising the major portion of the balance at 39% and 16%, respectively, of the triglyceride composition.

Obtaining nucleic acid sequences capable of producing a phenotypic result in FAS, desaturation and/or incorporation of fatty acids into a glycerol backbone to produce an oil is subject to various obstacles including but not limited to the identification of metabolic factors of interest, choice and characterization of a protein source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, the identification of enzyme targets and useful plant sources for nucleic acid sequences of such enzyme targets capable of modifying fatty acid compositions are needed. Ideally, an enzyme target will be amenable to one or more applications alone or in combination with other nucleic acid sequences relating to increased/decreased oil production, the ratio of saturated to unsaturated fatty acids in the fatty acid pool, and/or to novel oils compositions as a result of the modifications to the fatty acid pool. Once enzyme target(s) are identified and qualified, quantities of protein and purification protocols are needed for sequencing. Ultimately, useful nucleic acid constructs having the necessary elements to provide a phenotypic modification and plants containing such constructs are needed.

Relevant Literature

A 200-fold purification of *Carthamus tinctorius* ("safflower") stearoyl-ACP desaturase was reported by McKeon & Stumpf in 1982, following the first publication of their protocol in 1981. McKeon, T. & Stumpf, P. *J. Biol. Chem.* (1982) 257:12141-12147; McKeon, T. & Stumpf, P. *Methods in Enzymol.* (1981) 71:275-281.

BRIEF DESCRIPTION OF THE DRAWINGS

FIG. 1 provides amino acid sequence of fragments relating to *C. tinctorius* desaturase. Fragments F1 through F11 are also provided in the sequence listing as SEQ ID NO: 1 through SEQ ID NO: 11, respectively. Each fragment represents a synthesis of sequence information from peptides originating from different digests which have been matched and aligned. In positions where there are two amino acids indicated, the top one corresponds to that found in the translation of the cDNA; the lower one was detected either as a second signal at the same position of one of the sequenced peptides, or as a single unambiguous signal found in one or more of the overlapping peptides comprising the fragment. Residues in F9 shown in lower case letters represent positions where the called sequence does not agree with that predicted from the cDNA, but where the amino acid assignment is tentative because of the presence of a contaminating peptide. The standard one letter code for amino acid residues has been used. X represents a position where no signal was detectable, and which could be a modified residue. F1 corresponds to the N-terminal sequence of the mature protein. The underlined region in F2 is the sequence used in designing PCR primers for probe synthesis.

FIG. 2 provides a cDNA sequence (SEQ ID NO: 12) and the corresponding translational peptide sequence (SEQ ID NO: 13) derived from *C. tinctorius* desaturase. The cDNA sequence includes both the plastid transit peptide encoding sequence and the sequence encoding the mature protein.

FIG. 3 provides cDNA sequence of *Ricinus communis* ("castor bean") desaturase. FIG. 3A provides preliminary partial cDNA sequence of a 1.7 kb clone of *R. communis* desaturase (SEQ ID NO: 14). The sequence is from the 5' end of the clone. FIG. 3B provides the complete cDNA sequence of the approximately 1.7 kb clone (SEQ ID NO: 15) and the corresponding translational peptide sequence (SEQ ID NO: 16).

FIG. 4 provides sequence of *Brassica campestris* ("rapeseed") desaturase. FIG. 4A represents partial DNA sequence of a 1.6 kb clone pCGN3235 (SEQ ID NO: 17), from the 5' end of the clone. FIG. 4B represents partial DNA sequence of a 1.2 kb clone, pCGN3236, from the 5' end of the clone (SEQ ID NO: 18). Initial sequence for the 3' ends of the two *B. campestris* desaturase clones indicates that pCGN3236 is a shorter cDNA for the same clone as pCGN3235. FIG. 4C provides complete cDNA sequence of *B. campestris* desaturase above, pCGN3235 (SEQ ID NO: 19) and the corresponding translational peptide sequence (SEQ ID NO: 20).

FIG. 5 provides preliminary partial cDNA sequence of *Simmondsia chinensis* ("jojoba") desaturase (SEQ ID NO: 43). The translated amino acid sequence is also shown.

FIG. 6 shows the design of forward and reverse primers (SEQ ID NO: 21 through SEQ ID NO: 26) used in polymerase chain reaction (PCR) from the sequence of *C. tinctorius* desaturase peptide "Fragment F2" (SEQ ID NO: 2).

FIG. 7 provides maps of desaturase cDNA clones showing selected restriction enzyme sites.

FIG. 8 provides approximately 3.4 kb of genomic sequence of Bce4 (SEQ ID NO: 27).

FIG. 9 provides approximately 4 kb of genomic sequence of Bcg 4-4 ACP sequence (SEQ ID NO: 28).

SUMMARY OF THE INVENTION

Figure 7A:
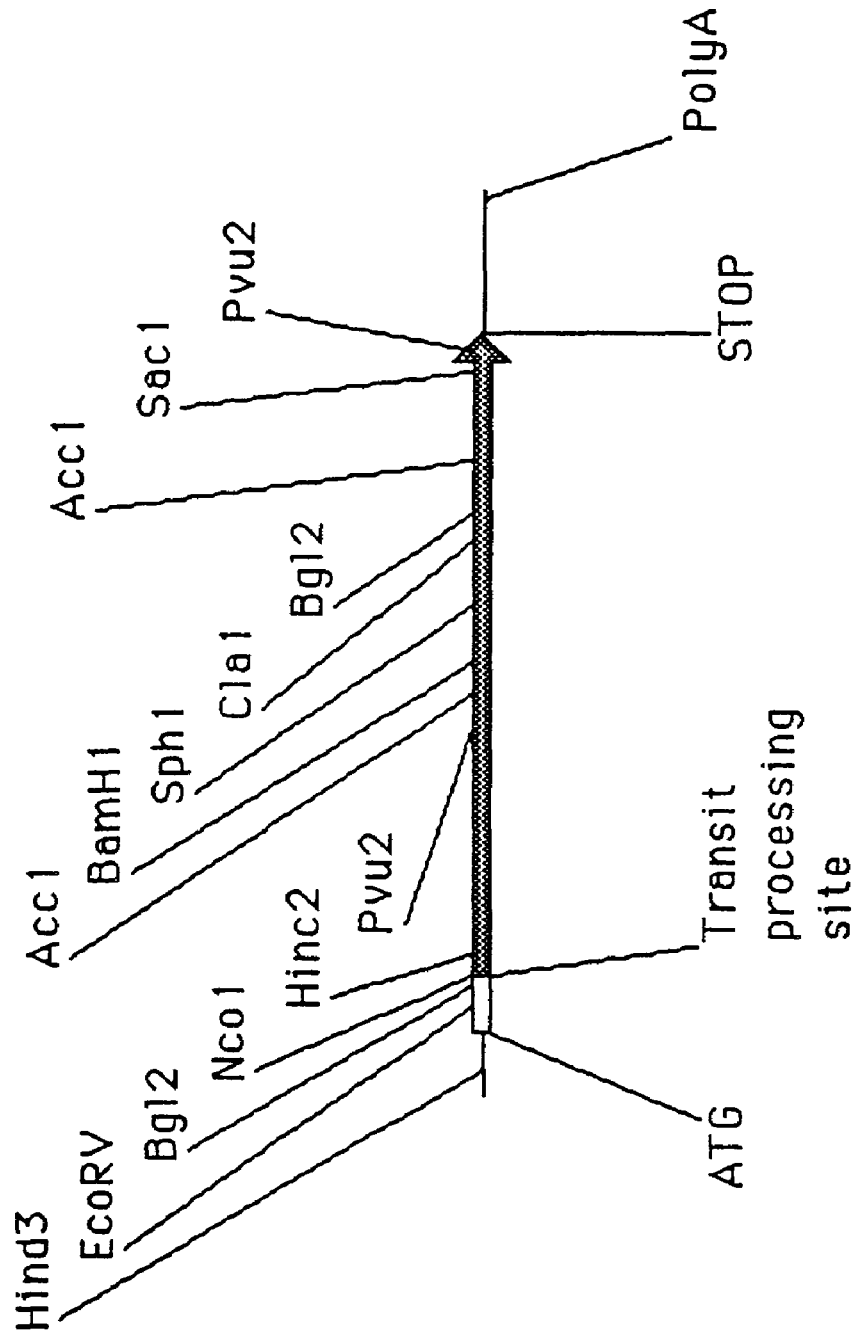
FIG. 7A represents a *C. tinctorius* clone.
Figure 7B:
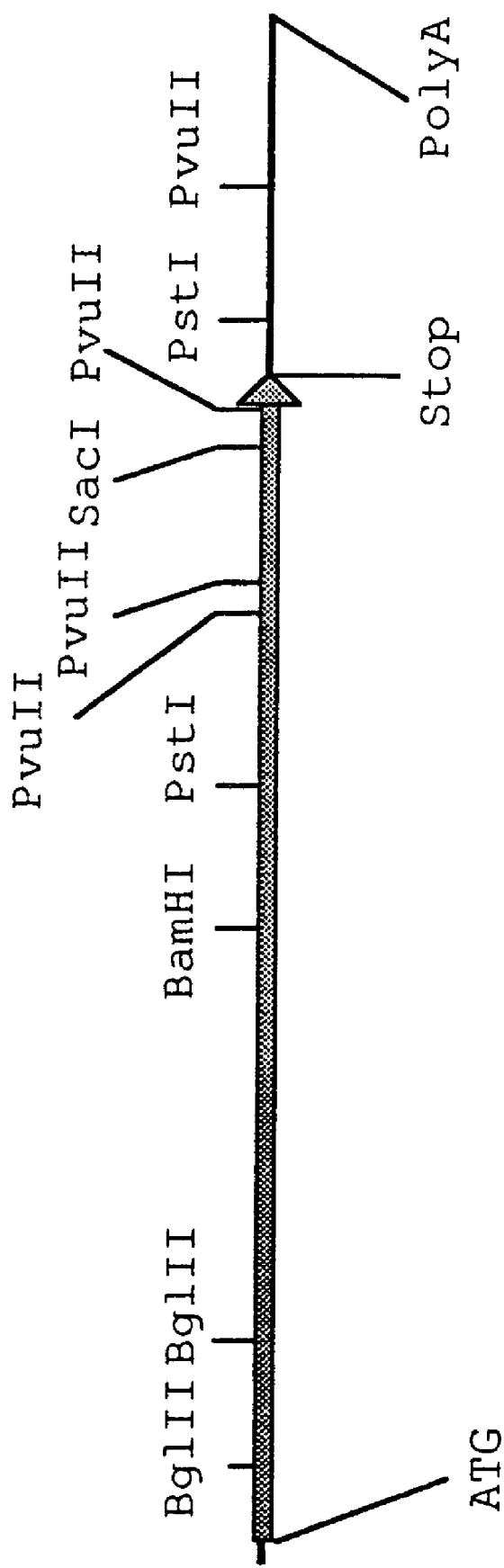
FIG. 7B represents a *R. communis* clone.

By this invention, compositions and methods of use of plant desaturase enzymes, especially Δ-9 desaturases, are provided. Of special interest are methods and compositions of amino acids and nucleic acid sequences related to biologically active plant desaturases as well as sequences, especially nucleic acid sequences, which are to be used as probes, vectors for transformation or cloning intermediates. Biologically active sequences may be found in a sense or anti-sense orientation as to transcriptional regulatory regions found in various constructs.

A first aspect of this invention relates to *C. tinctorius* Δ-9 desaturase substantially free of seed storage protein. Amino acid sequence of this desaturase is provided in FIG. 2 and as SEQ ID NO: 13.

DNA sequence of *C. tinctorius* desaturase gene (SEQ ID NO: 12) is provided, as well as DNA sequences of desaturase genes from a *Ricinus* (SEQ ID NO: 14 and SEQ ID NO: 15) a *Brassica* (SEQ ID NO: 17 through SEQ ID NO: 19) and a *Simmondsia* (SEQ ID NO: 43) plant.

In yet a different embodiment of this invention, plant desaturase cDNA of at least 10 nucleotides or preferably at least 20 nucleotides and more preferably still at least 50 nucleotides, known or homologously related to known Δ-9 desaturase(s) is also provided. The cDNA encoding precursor desaturase or, alternatively, biologically active, mature desaturase is provided herein.

Methods to use nucleic acid sequences to obtain other plant desaturases are also provided. Thus, a plant desaturase may be obtained by the steps of contacting a nucleic acid sequence probe comprising nucleotides of a known desaturase sequence and recovery of DNA sequences encoding plant desaturase having hybridized with the probe.

This invention also relates to methods for obtaining plant Δ-9 desaturase by contacting an antibody specific to a known desaturase, such as *C. tinctorius* stearoyl-ACP desaturase, with a candidate plant stearoyl-ACP desaturase under conditions conducive to the formation of an antigen:antibody immunocomplex and the recovery of the candidate plant stearoyl-ACP desaturase which reacts thereto.

In a further aspect of this invention DNA constructs comprising a first DNA sequence encoding a plant desaturase and a second DNA sequence which is not naturally found joined to said plant desaturase are provided. This invention also relates to the presence of such constructs in host cells, especially plant host cells. In yet a different aspect, this invention relates to transgenic host cells which have an expressed desaturase therein.

Constructs of this invention may contain, in the 5' to 3' direction of transcription, a transcription initiation control regulatory region capable of promoting transcription in a host cell and a DNA sequence encoding plant desaturase. Transcription initiation control regulatory regions capable of expression in prokaryotic or eukaryotic host cells are provided. Most preferred are transcription initiation control regions capable of expression in plant cells, and more preferred are transcription and translation initiation regions preferentially expressed in plant cells during the period of lipid accumulation. The DNA sequence encoding plant desaturase of this invention may be found in either the sense or anti-sense orientation to the transcription initiation control region.

Specific constructs, expression cassettes having in the 5' to 3' direction of transcription, a transcription and translation initiation control regulatory region comprising sequence. immediately 5' to a structural gene preferentially expressed in plant seed during lipid accumulation, a DNA sequence encoding desaturase, and sequence 3' to the structural gene are also provided. The construct may preferably contain DNA sequences encoding plant desaturase obtainable (included obtained) from *Carthamus, Ricinus, Brassica* or *Simmondsia* Δ-9 desaturase genes. Transcription and translation initiation control regulatory regions are preferentially obtained from structural genes preferentially expressed in plant embryo tissue such as napin, seed-ACP or Bce-4 gene promoters.

By this invention, methods and constructs to inhibit the production of endogenous desaturase are also provided. For example, an anti-sense construct comprising, in the 5' to 3' direction of transcription, a transcription initiation control regulatory region functional in a plant cell, and an anti-sense DNA sequence encoding a portion of a plant Δ-9 desaturase may be integrated into a plant host cell to decrease desaturase levels.

In yet a different embodiment, this invention is directed to a method of producing plant desaturase in a host cell comprising the steps of growing a host cell comprising an expression cassette, which would contain in the direction of transcription, a) a transcription and translation initiation region functional in said host cell, b) the DNA sequence encoding a plant desaturase in reading frame with said initiation region, and c) and a transcript termination region functional in said host cell, under conditions which will promote the expression of the plant desaturase. Cells containing a plant desaturase as a result of the production of the plant desaturase encoding sequence and also contemplated herein.

By this invention, a method of modifying fatty acid composition in a host plant cell. from a given level of fatty acid saturation to a different level of fatty acid saturation is provided by growing a host plant cell having integrated into its genome a recombinant DNA sequence encoding a plant desaturase in either a sense or anti-sense orientation under control of regulatory elements functional in said plant cell during lipid accumulation under conditions which will promote the activity of said regulatory elements. Plant cells having such a modified level of fatty acid saturation are also contemplated hereunder. Oilseeds having such a modified level of fatty acid saturation and oils produced from such oilseeds are further provided.

DETAILED DESCRIPTION OF THE INVENTION

A plant desaturase of this invention includes any sequence of amino acids, such as a protein, polypeptide, or peptide fragment, obtainable from a plant source which is capable of catalyzing the insertion of a first double bond into a fatty acyl-ACP moiety in a plant host cell, i.e., in vivo, or in a plant cell-like environment, i.e. in vitro. "A plant cell-like environment" means that any necessary conditions are available in an environment (i.e., such factors as temperatures, pH, lack of inhibiting substances) which will permit the enzyme to function In particular, this invention relates to enzymes which add such a first double bond at the ninth carbon position in a fatty acyl-ACP chain. There may be similar plant desaturase enzymes of this invention with different specificities, such as the Δ-12 desaturase of carrot.

Nucleotide sequences encoding desaturases may be obtained from natural sources or be partially or wholly artificially synthesized. They may directly correspond to a desaturase endogenous to a natural plant source or contain modified amino acid sequences, such as sequences which have been mutated, truncated, increased or the like. Desaturases may be obtained by a variety of methods, including but not limited to, partial or homogenous purification of plant extracts, protein modeling, nucleic acid probes, antibody preparations and sequence comparisons. Typically a plant desaturase will be derived in whole or in part from a natural plant source.

Of special interest are Δ-9 desaturases which are obtainable, including those with are obtained, from *Carthamus, Ricinus, Simmondsia,* or *Brassica,* for example *C. tinctorius, R. communis, S. chinensis* and *B. campestris,* respectively, or from plant desaturases which are obtainable through the use of these sequences. "Obtainable" refers to those desaturases which have sufficiently similar sequences to that of the native sequences provided herein to provide a biologically active desaturase.

Once a DNA sequence which encodes a desaturase is obtained, it may be employed as a gene of interest in a nucleic acid construct or in probes in accordance with this invention. A desaturase may be produced in host cells for harvest or as a means of effecting a contact between the desaturase and its substrate. Constructs may be designed to produce desaturase in either prokaryotic or eukaryotic cells. Plant cells containing recombinant constructs encoding biologically active desaturase sequences, both expression and anti-sense constructs, as well as plants and cells containing modified levels of desaturase proteins are of special interest. For use in a plant cell, constructs may be designed which will effect an increase or a decrease in amount of desaturase enzyme available to a plant cell transformed with such a construct.

Where the target gene encodes an enzyme, such as a plant desaturase, which is already present in the host plant, there are inherent difficulties in analyzing mRNA, engineered protein or enzyme activity, and modified fatty acid composition or oil content in plant cells, especially in developing seeds; each of which can be evidence of biological activity. This is because the levels of the message, enzyme and various fatty acid species are changing rapidly during the stage where measurements are often made, and thus it can be difficult to discriminate between changes brought about by the presence of the foreign gene and those brought about by natural developmental changes in the seed. Where an expressed Δ-9 desaturase DNA sequence is derived from a plant species heterologous to the plant host into which the sequence is introduced and has a distinguishable DNA sequence, it is often possible to specifically probe for expression of the foreign gene with oligonucleotides complimentary to unique sequences of the inserted DNA/RNA. And, if the foreign gene codes for a protein with slightly different protein sequence, it may be possible to obtain antibodies which recognize unique epitopes on the engineered protein. Such antibodies can be obtained by mixing the antiserum to the foreign protein with extract from the host plant, or with extracts containing the host plant enzyme. For example, one can isolate antibodies uniquely specific to a C. tinctorius Δ-9 desaturase by mixing antiserum to the desaturase with an extract containing a Brassica Δ-9 desaturase. Such an approach will allow the detection of C. tinctorius desaturase in Brassica plants transformed with the C. tinctorius desaturase gene. In plants expressing an endogenous gene in an antisense orientation, the situation is slightly different. In this case, there are no specific reagents to measure expression of a foreign protein. However, one is attempting to measure a decrease in an enzyme activity that normally is increasing during development. This makes detection of expression a simpler matter. In the final seed maturation phase, enzyme activities encoded by genes affecting oil composition usually disappear and cannot be detected in final mature seed. Analysis of the fatty acid content may be performed by any manner known to those skilled in the art, including gas chromatography, for example.

By increasing the amount of desaturase available in the plant cell, an increased percentage of unsaturated fatty acids may be provided; by decreasing the amount of desaturase, an increased percentage of saturated fatty acids may be provided. (Modifications in the pool of fatty acids available for incorporation into triglycerides may likewise affect the composition of oils in the plant cell.) Thus, an increased expression of desaturase in a plant cell may result in increased proportion of fatty acids, such as one or more of palmitoleate (C16:1), oleate (C18:1), linoleate (C18:2) and linolenate (C18:3) are expected. In rapeseed, increased desaturase expression lowers stearate and total saturates. Of special interest is the production of triglycerides having increased levels of oleate. Using anti-sense technology, alternatively, a decrease in the amount of desaturase available to the plant cell is expected, resulting in a higher percentage of saturates such as one or more of laurate (C12:0), myristate (C14:0), palmitate (C16:0), stearate (C18:0), arachidate (C20:0), behemate (C22:0) and lignocerate (C24:0). In rapeseed reduced desaturase results in increased stearate levels and total saturates. Of special interest is the production of triglycerides having increased levels of stearate or palmitate and stearate. In addition, the production of a variety of ranges of such saturates is desired. Thus, plant cells having lower and higher levels of stearate fatty acids are contemplated. For example, fatty acid compositions, including oils, having a 10% level of stearate as well as compositions designed to have up to an appropriate 60% level of stearate or other such modified fatty acid(s) composition are contemplated.

Oils with increased percentages of stearate, especially rapeseed triglyceride oils, are provided herein. Increased stearate percentages (by weight) ranging from native up to 25 fold are described. By manipulation of various aspects of the DNA constructs (e.g., choice of promoters, number of copies, etc.) and traditional breeding methods, one skilled in the art may achieve even greater levels of stearate. By combination of the plant desaturase sequence in combination with other DNA sequences, a variety of other fatty acid compositions and triglycerides can be achieved in rapeseed and other plant species.

Oilseed containing stearate rich fatty acids having the majority incorporated into triglyceride oils will contain a certain percentage of triglycerides of the following formula:

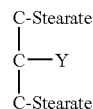

Wherein Y is an unsaturated fatty acid. In a certain triglycerides, Y shall be oleate. Triglyceride oils with stearate-unsaturate-stearate (S-U-S) and/or stearate-oleate-stearate (S-O-S) may be novel oils compositions, particularly in oilseed varieties which naturally contain low stearate levels. Such triglyceride oils may find special application in the production of non-hydrogenated margarines, for example. Edible oils having naturally low stearate levels include canola (rapeseed), sunflower, peanut, safflower, coconut and oil palm, (See, Table I.)

The modification of fatty acid compositions may also affect the fluidity of plant membranes. Different lipid concentrations have been observed in cold-hardened plants, for example. By this invention, one may be capable of introducing traits which will lend to chill tolerance. Constitutive or temperature inducible transcription initiation regulatory control regions may have special applications for such uses.

Other applications for use of cells or plants producing desaturase may also be found. For example, potential herbicidal agents selective for plant desaturase may be obtained through screening to ultimately provide environmentally safe herbicide products. The plant desaturase can also be used in conjunction with chloroplast lysates to enhance the production and/or modify the composition of the fatty acids prepared in vitro. The desaturase can also be used for studying the mechanism of fatty acid formation in plants and bacteria. For these applications, constitutive promoters may find the best use.

Constructs which contain elements to provide the transcription and translation of a nucleic acid sequence of interest in a host cell are "expression cassettes". Depending upon the host, the regulatory regions will vary, including regions from structural genes from viruses, plasmid or chromosomal genes, or the like. For expression in prokaryotic or eukaryotic microorganisms, particularly unicellular hosts, a wide variety of constitutive or regulatable promoters may be employed. Among transcriptional initiation regions which have been described are regions from bacterial and yeast hosts, such as *E. coli, B. subtilis, Saccharomyces cerevisiae*, including genes such as β-galactosidase, T7 polymerase, trp E and the like.

A recombinant construct for expression of desaturase in a plant cell ("expression cassette") will include, in the 5' to 3' direction of transcription, a transcription and a translation initiation control regulatory region (the transcriptional and translational initiation regions together often also known as a "promoter") functional in a plant cell, a nucleic acid sequence encoding a plant desaturase, and a transcription termination region. Numerous transcription initiation regions are available which provide for a wide variety of constitutive or regulatable, e.g., inducible, transcription of the desaturase structural gene. Among transcriptional initiation regions used for plants are such regions associated with cauliflower mosaic viruses (35S, 19S), and structural genes such as for nopaline synthase or mannopine synthase or napin and ACP promoters, etc. The transcription/translation initiation regions corresponding to such structural genes are found immediately 5' upstream to the respective start codons. Thus, depending upon the intended use, different promoters may be desired.

Of special interest in this invention are the use of promoters which are capable of preferentially expressing the desaturase in seed tissue, in particular, at early stages of seed oil formation. Examples of such seed-specific promoters include the region immediately 5' upstream of napin or seed ACP genes, such as described in co-pending U.S. Ser. No. 147,781, and the Bce-4 gene such as described in co-pending U.S. Ser. No. 494,722. Alternatively, the use of the 5' regulatory region associated with an endogenous plant desaturase structural gene and/or the transcription termination regions found immediately 3' downstream to the gene, may often be desired.

In addition, for some applications, use of more than one promoter may be desired. For example, one may design a dual promoter expression cassette each promoter having a desaturase sequence under its regulatory control. For example, the combination of an ACP and napin cassette could be useful for increased production of desaturase in a seed-specific fashion over a longer period of time and/or to exert a greater production of desaturase and hence have a greater effect on the cell than either individually.

To decrease the amount of desaturase found in a plant host cell, anti-sense constructs may be prepared and then inserted into the plant cell. By "anti-sense" is meant a DNA sequence in the 5' to 3' direction of transcription in relation to the transcription initiation region, which encodes a sequence complementary to the sequence of a native desaturase. It is preferred that an anti-sense plant desaturase sequence be complementary to a plant desaturase gene indigenous to the plant host. Sequences found in an anti-sense orientation may be found in constructs providing for transcription or transcription and translation of the DNA sequence encoding the desaturase, including expression cassettes. Constructs having more than one desaturase sequence under the control of more than one promoter or transcription initiation region may also be employed with desaturase constructs. Various transcription initiation regions may be employed. One of ordinary skill in the art can readily determine suitable regulatory regions. Care may be necessary in selecting transcription initiation regions to avoid decreasing desaturase activity in plant cells other than oilseed tissues. Any transcription initiation region capable of directing expression in a plant host which causes initiation of adequate levels of transcription selectively in storage tissues during seed development for example, should be sufficient. As such, seed specific promoters may be desired. Other manners of decreasing the amount of endogenous plant desaturase, such as ribozymes or the screening of plant cells transformed with constructs for rare events containing sense sequences which in fact act to decrease desaturase expression, are also contemplated herein. Other analogous methods may be applied by those of ordinary skill in the art.

By careful selection of plants, transformants having particular oils profiles may be obtained. This may in part depend upon the qualities of the transcription initiation region(s) employed or may be a result of culling transformation events to exploit the variabilities of expression observed.

For some applications, modified fatty acid compositions may be detected in developing seeds, whereas in other instances, such as for analysis of oil profile, detection of fatty acid modifications occurring later in the FAS pathway, or for detection of minor modifications to the fatty acid composition, analysis of fatty acid or oil from mature seeds may be preferred. Furthermore, analysis of oil and/or fatty acid content of individual seeds may be desirable, especially in detection of oil modification in the segregating T1 seed populations. As used herein, T1 indicates the plant and seed arising from transformation/regeneration protocols described herein. T2 indicates plants and seeds generated from the transgenic T1 seed.

In order to obtain the nucleic acid sequences encoding *C. tinctorius* desaturase via protein analysis, a protein preparation free of a major albumin-type contaminant is required. As demonstrated more fully in the Examples, the protocols of McKeon and Stumpf, supra, result in a preparation contaminated with a seed storage protein. Removal of the protein contaminant may be effected by application of a reverse-phase HPLC, or alternatively, by application of a reduction and alkylation step followed by electrophoresis and blotting, for example. Other purification methods may be employed as well, now that the presence of the contaminant is confirmed and various properties thereof described. Once the purified desaturase is obtained it may be used to obtain the corresponding amino acid and/or nucleic acid sequences thereto in accordance with methods familiar to those skilled in the art. Approximately 90% of the total amino acid sequence of the *C. tinctorius* desaturase is provided in FIG. 1 and in SEQ ID NOS: 1-11. The desaturase produced in accordance with the subject invention can be used in preparing antibodies for assays for detecting plant desaturase from other sources.

A nucleic acid sequence of this invention may include genomic or cDNA sequence and mRNA. A cDNA sequence may or may not contain pre-processing sequences, such as transit peptide sequences. Transit peptide sequences facilitate the delivery of the protein to a given organelle and are cleaved from the amino acid moiety upon entry into the organelle, releasing the "mature" sequence.

In FIG. 2 and SEQ ID NO: 13, the sequence of the *C. tinctorius* desaturase precursor protein is provided; both the transit peptide and mature protein sequence are shown. Also provided in this invention are cDNA sequences relating to *R. communis* desaturase (FIG. 3 and SEQ ID NOS: 14-15), *B. campestris* desaturase (FIG. 4 and SEQ ID NOS: 17-19) and *S. chinesis* (FIG. 5 and SEQ ID NOS: 43).

The use of the precursor cDNA sequence is preferred in desaturase expression cassettes. In addition, desaturase transit peptide sequences may be employed to translocate other proteins of interest to plastid organelles for a variety of uses, including the modulation of other enzymes related to the FAS pathway. See, European Patent Application Publication No. 189,707.

As described in more detail below, the complete genomic sequence of a desaturase may be obtained by the screening of a genomic library with a desaturase cDNA probe and isolating those sequences which regulate expression in seed tissue. In this manner, the transcription, translation initiation regions and/or transcript termination regions of the desaturase may be obtained for use in a variety of DNA constructs, with or without the respective desaturase structural gene.

Other nucleic acid sequences "homologous" or "related" to DNA sequences encoding other desaturases are also provided. "Homologous" or "related" includes those nucleic acid sequences which are identical or conservatively substituted as compared to the exemplified *C. tinctorius, R. communis, S. chinesis* or *B. campestris* desaturase sequences of this invention or a plant desaturase which has in turn been obtained from a plant desaturase of this invention. By conservatively substituted is meant that codon substitutions encode the same amino acid, as a result of the degeneracy of the DNA code, or that a different amino acid having similar properties to the original amino acid is substituted. One skilled in the art will readily recognize that antibody preparations, nucleic acid probes (DNA and RNA) sequences encoding and the like may be prepared and used to screen and recover desaturase from other plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available. Examples of some of the available antibody detection systems are described by Oberfilder (*Focus* (1989) BRL Life Technologies, Inc., 11:1-5).

A "homologous" or "related" nucleic acid sequence will show at least about 60% homology, and more preferably at least about 70% homology, between the known desaturase sequence and the desired candidate plant desaturase of interest, excluding any deletions which may be present. Homology is determined upon comparison of sequence information, nucleic acid or amino acid, or through hybridization reactions. Amino acid sequences are considered homologous by as little as 25% sequence identity between the two complete mature proteins. (See generally, Doolittle, R. F., of URFS and ORFS, University Science Books, CA, 1986.)

Oligonucleotide probes can be considerably shorter than the entire sequence, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. (See, Gould, et al., *PNAS USA* (1989) 86:1934-1938.) Longer oligonucleotides are also useful, up to the full length of the gene encoding the polypeptide of interest. When longer nucleic acid fragments are employed (>100 bp) as probes, especially when using complete or large cDNA sequences, one would screen with low stringencies (for example 40-50° C. below the melting temperature of the probe) in order to obtain signal from the target sample with 20-50% deviation, i.e., homologous sequences. (See, Beltz, et al., *Methods in Enzymology* (1983) 100:266-285.) Both DNA and RNA probes can be used.

A genomic library prepared from the plant source of interest may be probed with conserved sequences from a known desaturase to identify homologously related sequences. Use of the entire cDNA may be employed if shorter probe sequences are not identified. Positive clones are then analyzed by restriction enzyme digestion and/or sequencing. When a genomic library is used, one or more sequences may be identified providing both the coding region, as well as the transcriptional regulatory elements of the desaturase gene from such plant source. In this general manner, one or more sequences may be identified providing both the coding region, as well as the transcriptional regulatory elements of the desaturase gene from such plant source.

In use, probes are typically labeled in a detectable manner (for example with $^{32}$P-labeled or biotinylated nucleotides) and are incubated with single-stranded DNA or RNA from the plant source in which the gene is sought, although unlabeled oligonucleotides are also useful. Hybridization is detected by means of the label after single-stranded and double-stranded (hybridized) DNA or DNA/RNA have been separated, typically using nitrocellulose paper or nylon membranes. Hybridization techniques suitable for use with oligonucleotides are well known to those skilled in the art. Thus, plant desaturase genes may be isolated by various techniques from any convenient plant. Plant desaturase of developing seed obtained from other oilseed plants, such as soybean, coconut, oilseed rape, sunflower, oil palm, peanut, cocoa, cotton, corn and the like are desired as well as from non-traditional oil sources, including but not limited to spinach chloroplast, avocado mesocarp, cuphea, California Bay, cucumber, carrot, meadowfoam, *Oenothera* and *Euglena gracillis*.

Once the desired plant desaturase sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized, where one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

Recombinant constructs containing a nucleic acid sequence encoding a desaturase of this invention may be combined with other, i.e. "heterologous," DNA sequences in a variety of ways. By heterologous DNA sequences is meant any DNA sequence which is not naturally found joined to the native desaturase, including combinations of DNA sequences from the same plant of the plant desaturase which are not naturally found joined together. In a preferred embodiment, the DNA sequence encoding a plant desaturase is combined in a DNA construct having, in the 5' to 3' direction of transcription, a transcription initiation control region capable of promoting transcription in a host cell, and a DNA sequence encoding a desaturase in either a sense or anti-sense orientation. As described in more detail elsewhere, a variety of regulatory control regions containing transcriptional or transcriptional and translational regions may be employed, including all or part of the non-coding regions of the plant desaturase.

The open reading frame coding for the plant desaturase or functional fragment thereof will be joined at its 5' end to a transcription initiation regulatory control region. In some instances, such as modulation of plant desaturase via a desaturase in an anti-sense orientation, a transcription initiation region or transcription/translation initiation region may be used. In embodiments wherein the expression of the desaturase protein is desired in a plant host, a transcription/ translation initiation regulatory region, is needed. Additionally, modified promoters, i.e., having transcription initiation regions derived from one gene source and translation initiation regions derived from a different gene source or enhanced promoters, such as double 35S CaMV promoters, may be employed for some applications.

As described above, of particular interest are those 5' upstream non-coding regions which are obtained from genes regulated during seed maturation, particularly those preferentially expressed in plant embryo tissue, such as ACP- and napin-derived transcription initiation control regions. Such regulatory regions are active during lipid accumulation and therefore offer potential for greater control and/or effectiveness to modify the production of plant desaturase and/or modification of the fatty acid composition. Especially of interest are transcription initiation regions which are preferentially expressed in seed tissue, i.e., which are undetectable in other plant parts. For this purpose, the transcript initiation region of acyl carrier protein isolated from *B. campestris* seed and designated as "Bcg 4-4" and an unidentified gene isolated from *B. campestris* seed and designated as "Bce-4" are also of substantial interest.

Briefly, Bce4 is found in immature embryo tissue at least as early as 11 days after anthesis (flowering), peaking about 6 to 8 days later or 17-19 days post-anthesis, and becoming undetectable by 35 days post-anthesis. The timing of expression of the Bce4 gene closely follows that of lipid accumulation in seed tissue. Bce4 is primarily detected in seed embryo tissue and to a lesser extent found in the seed coat. Bce4 has not been detected in other plant tissues tested, root, stem and leaves.

Approximately 3.4 kb genomic sequence of Bce4 is provided in FIG. 8 and as SEQ ID NO: 27, including about 1 kb 5' to the structural gene, about 0.3 kb of the Bce4 coding gene sequence, and about 2.1 kb of the non-coding regulatory 3' sequence. Bce4 transcript initiation regions will contain at least 1 kb and more preferably about 5 to about 7.5 kb of sequence immediately 5' to the Bce4 structural gene.

The Bcg 4-4 ACP message presents a similar expression profile to that of Bce4 and, therefore, also corresponds to lipid accumulation in the seed tissue. Bcg 4-4 is not found in the seed coat and may show some differences in expression level, as compared to Bce4, when the Bcg 4-4 5' non-coding sequence is used to regulate transcription or transcription and translation of a plant stearoyl-ACP desaturase of this invention. Genomic sequence of Bcg 4-4 is provided in FIG. 9 and as SEQ ID NO: 28, including about 1.5 kb 5' to the structural gene, about 1.2 kb of the Bcg 4-4 (ACP) structural gene sequence, and about 1.3 kb of the non-coding regulatory 3' sequence.

The napin 1-2 message is found in early seed development and thus, also offers regulatory regions which can offer preferential transcriptional regulation of a desired DNA sequence of interest such as the plant desaturase DNA sequence of this invention during lipid accumulation. Napins are one of the two classes of storage proteins synthesized in developing *Brassica* embryos (Bhatty, et al., *Can J. Biochem*. (1968) 46:1191-1197) and have been used to direct tissue-specific expression when reintroduced into the *Brassica* genome (Radke, et al., *Theor. Appl. Genet.* (1988) 75:685-694).

Figure 10:
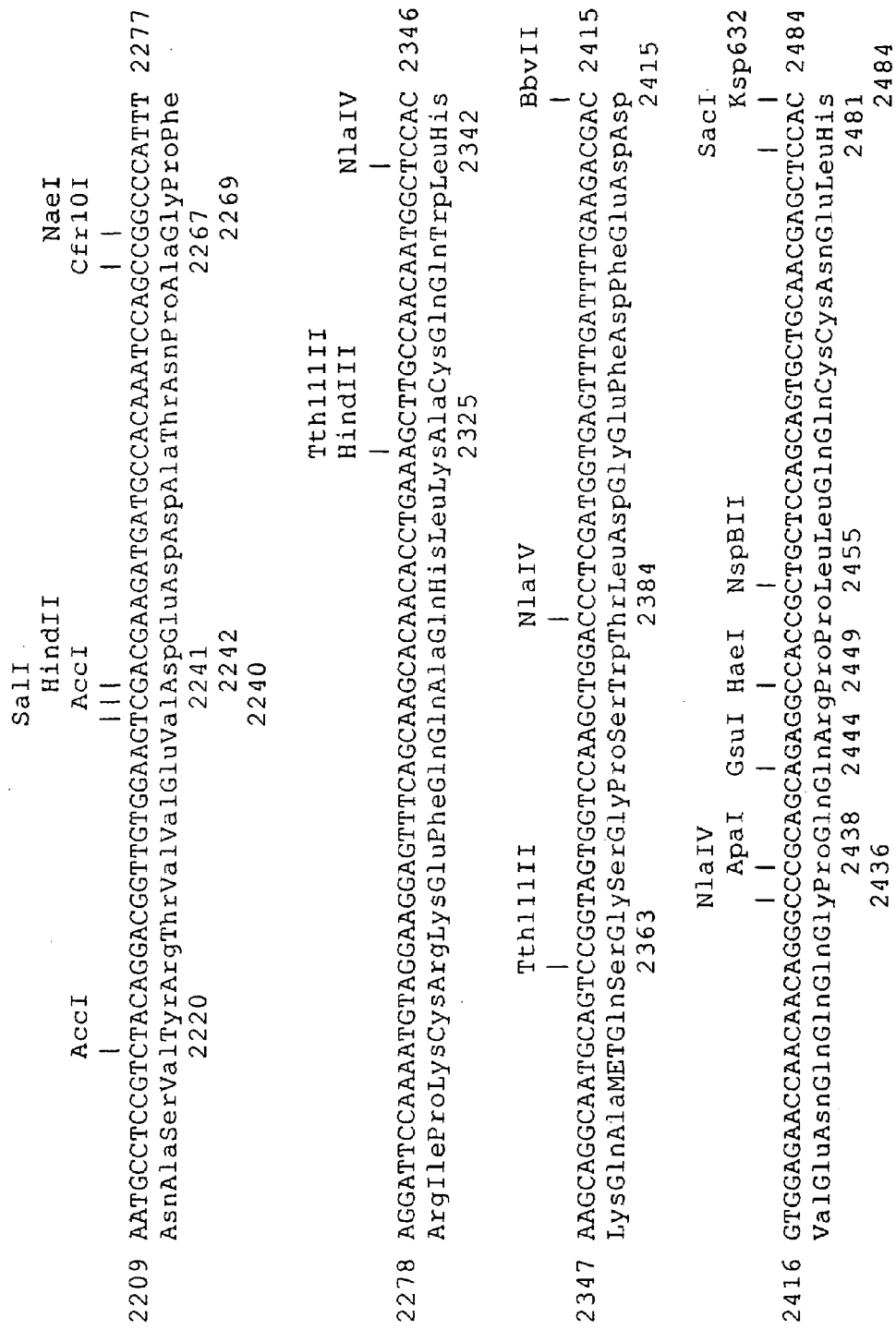
FIG. 10 provides a restriction map of cloned λCGN 1-2 showing the entire napin coding region sequence as well as extensive 5' upstream and 3' downstream sequences (SEQ ID NO: 29).
Figure 10:
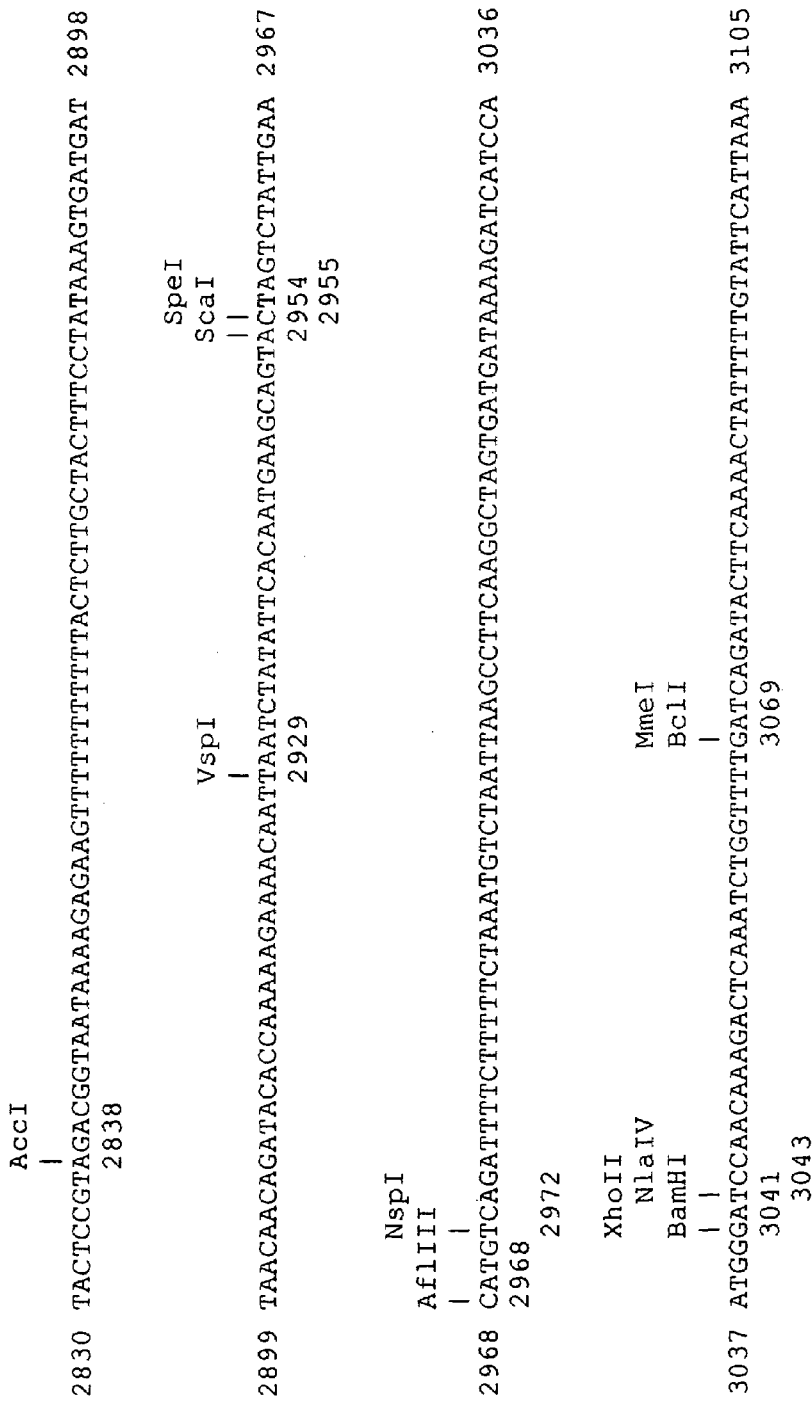

Genomic sequence of napin 1-2 is provided in FIG. 10 and as SEQ ID NO: 29, including about 1.7 kb 5' to the structural gene and about 1.3 kb of the non-coding regulatory 3' sequence Regulatory transcript termination regions may be provided in DNA constructs of this invention as well. Transcript termination regions may be provided by the DNA sequence encoding the plant desaturase or a convenient transcription termination region derived from a different gene source, especially the transcript termination region which is naturally associated with the transcript initiation region. The transcript termination region will contain at least about 1 kb, preferably about 3 kb of sequence 3' to the structural gene from which the termination region is derived.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy. to an auxotrophic host, viral immunity or the like. Depending upon the number of different host species into which the expression construct or components thereof are introduced, one or more markers may be employed, where different conditions for selection are used for the different hosts.

The manner in which the DNA construct is introduced into the plant host is not critical to this invention. Any method which provides for efficient transformation may be employed. Various methods for plant cell transformation include the use of Ti- or Ri-plasmids, microinjection, electroporation, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cell and gall.

A preferred method for the use of *Agrobacterium* as the vehicle for transformation of plant cells employs a vector having a broad host range replication system, at least one T-DNA boundary and the DNA sequence or sequences of interest. Commonly used vectors include pRK2 or derivatives thereof. See, for example, Ditta et al., *PNAS USA*, (1980) 77:7347-7351 and EPA 0 120 515, which are incorporated herein by reference. Normally, the vector will be free of genes coding for opines, oncogenes and vir-genes. Included with the expression construct and the T-DNA will be one or more markers, which allow for selection of transformed *Agrobacterium* and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

The expression constructs may be employed with a wide variety of plant life, particularly plant life involved in the production of vegetable oils. These plants include, but are not limited to rapeseed, sunflower, *C. tinctorius*, cotton, Cuphea, peanut, soybean, oil palm and corn. Anti-sense constructs may be employed in such plants which share complementarity between the endogenous sequence and the anti-sense desaturase. Of special interest is the use of an anti-sense construct having a *B. campestris* desaturase in rapeseed, including *B. campestris* and *B. napus*.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils compositions. A variety of stable genetic lines having fixed levels of saturation may be obtained and integrated into a traditional breeding program. Hemizygous and heterozygous lines or homozygous lines may demonstrate different useful properties for oil production and/or breeding. For example, saturation levels may be increased up to 2-fold by the development of homozygous plants as compared with heterozygous (including hemizygous) plants.

The invention now being generally described, it will be more readily understood by reference to the following examples which are included for purposes of illustration only and are not intended to limit the present invention.

EXAMPLES

Materials

Commercially available biological chemicals and chromatographic materials, including BSA, catalase (twice crystalized from bovine liver), spinach ferredoxin, ferredoxin-$NADP^+$ oxidoreductase (spinach leaf), NADPH, unlabeled fatty acids, DEAE-cellulose (Whatman DE-52) CNBr-activated Sepharose 4B, and octyl-Sepharose, and Reactive Blue Agarose are from Sigma (St. Louis, Mo.). Triethylamine, trichloroacetic acid, guanidine-HCl, and hydrazine-hydrate are also from Sigma. Proteolytic enzymes, including endoproteinases lysC, gluC, and aspN are sequencing grade enzymes obtained from Boehringer Mannheim (Indianapolis, Ind.). Organic solvents, including acetone, acetonitrile, methanol, ether and petroleum ether are purchased from J. T. Baker (Phillipsburg, N.J.); concentrated acids and sodium sulfate are also from J.T. Baker (Phillipsburg, N.J.). HPLC grade acetonitrile and trifluoracetic acid (TFA) are obtained from Burdick and Jackson (Muskegon, Mich.), and from Applied Biosystems (Foster City, Calif.), respectively. Radiochemicals, including [9,10(n)-$^3$H] oleic acid (10 mCi/µmol) and [$^3$H]-iodoacetic acid (64 Ci/mol) are from New England Nuclear (Boston, Mass.). Phenacyl-8 Reagent (bromoacetophenone with a crown ether catalyst) used to prepare phenacyl esters of the fatty acids for analysis are from Pierce (Rockford, Ill.). C18 reversed-phase thin-layer chromatography plates are from Whatman (Clifton, N.J.).

Acyl carrier protein (ACP) and acyl-ACP synthase are isolated from *E. coli* strain K-12 as described by Rock and Cronan (Rock and Cronan, *Methods in Enzymol* (1981) 71:341-351 and Rock et al., *Methods in Enzymol*. (1981) 72:397-403). The *E. coli* is obtainable from Grain Processing (Iowa) as frozen late-logarithmic phase cells.

[9,10(n)-$^3$H]stearic acid is synthesized by reduction of [9,10(n)-$^3$H]oleic acid with hydrazine hydrate essentially as described by Johnson and Gurr (*Lipids* (1971) 6:78-84). [9,10 (n)-$^3$H]oleic acid (2 mCi), supplemented with 5.58 mg unlabeled oleic acid to give a final specific radioactivity of 100 mCi/mmol, is dissolved in 2 ml of acetonitrile, acidified with 40 µl of glacial acetic acid, and heated to 55° C. Reduction is initiated with 100 µl of 60% (w/w) hydrazine hydrate; oxygen is bubbled through the mixture continuously. After each hour acetonitrile is added to bring the volume back to 2 ml and an additional 100 µl of hydrazine hydrate is added. At the end of 5 hr. the reaction is stopped by addition of 3 ml of 2M HCl. The reaction products are extracted with three 3 ml aliquots of petroleum ether and the combined ether extracts are washed with water, dried over sodium sulfate and evaporated to dryness. The dried reaction products are redissolved in 1.0 ml acetonitrile and stored at −20° C. The distribution of fatty acid products in a 15 µl aliquot is determined by preparation of phenacyl esters, which are then analyzed by thin layer chromatography on C-18 reverse phase plates developed with methanol:water:95:5 (v/v). Usually reduction to [9,10(n)-$^3$H] stearic acid is greater than 90%, a small amount of unreacted oleic acid may remain. The analysis is used to establish fraction of the total radioactivity that is present as stearate, and thereby to determine the exact substrate concentration in the enzyme assay.

Acyl-ACP substrates, including [9,10(n)-$^3$H] stearoyl-ACP are prepared and purified by the enzymatic synthesis procedure of Rock, Garwin, and Cronan (*Methods in Enzymol*. (1981) 72:397-403).

Acyl carrier protein was covalently bound to Sepharose 4B by reaction of highly purified ACP with CNBr-activated Sepharose 4B as described by McKeon and Stumpf (*J. Biol. Chem*. (1982) 257:12141-12147).

Example 1

In this example, an initial purification of *C. tinctorius* (safflower) desaturase, following the method of McKeon and Stumpf (*J. Biol. Chem*. (1982) 257:12141-12142), is described.

Assay: In each of the following steps, the presence of the enzyme is detected radiometrically by measuring enzyme-catalyzed release of tritium from [9,10(n)-$^3$H]stearoyl-ACP. Preparation of this substrate is described in "Materials" above.

The assay is performed by mixing 150 µl water, 5 ml dithiothreitol (100 mM, freshly prepared in water), 10 µl bovine serum albumin (10 mg/ml in water), 15 µl NADPH (25 mM, freshly prepared in 0.1M Tricine-HCl, pH 8.2), 25 µl spinach ferredoxin (2 mg/ml Sigma Type III in water), 3 µl NADPH:ferredoxin oxidoreductase (2.5 units/ml from Sigma), and 1 µl bovine liver catalase (800,000 units/ml from Sigma); after 10 min at room temperature, this mixture is added to a 13×100 mm screw-cap test tube containing 250 µl sodium 1,4-piperazinediethanesulfonate (0.1M, pH 6.0).

Finally, 10 µl of the sample to be assayed is added and the reaction is started by adding 30 µl of the substrate, [9,10(n)-$^3$H]stearoyl-ACP (100 µCi/µmol, 10 µM in 0.1M sodium 1,4-piperazinediethanesulfonate, pH 5.8). After sealing with a cap, the reaction is allowed to proceed for 10 min. while shaking at 23° C. The reaction is terminated by addition of 1.2 ml of 5.8% trichloroacetic acid and the resulting precipitated acyl-ACP's are removed by centrifugation. The tritium released into the aqueous supernatant by the desaturase reaction is measured by liquid scintillation spectrometry. One unit of activity is defined as the amount of enzyme required to convert 1 µmol of stearoyl-ACP to oleoyl-ACP, or to release 4 µg-atoms of $^3$H per minute.

Source tissue: Developing C. tinctorius seeds from greenhouse grown plants are harvested between 16 and 18 days after flowering, frozen in liquid nitrogen and stored at −70° C. until extracted.

Acetone Powder: Approximately 50 g of frozen seeds are ground in liquid nitrogen and sieved to remove large seed coat pieces to provide a fine embryo powder. The powder is washed with acetone on a Buchner funnel until all yellow color is absent from the filtrate. The powder is then air dried and further processed as described below, or may be stored frozen for at least a year at −70° C. without loss of enzyme activity.

Acetone Powder Extract: The dried acetone powder is weighed and triturated with ten times its weight of 20 mM potassium phosphate, pH 6.8; the mixture is then centrifuged at 12,000×g for 20 minutes and decanted through a layer of Miracloth (Calbiochem, La Jolla, Calif.).

Ion Exchange Chromatography: The acetone powder extract is then applied to a DEAE-cellulose column (Whatman DE-52) (1.5×12 cm) equilibrated with 20 mM potassium phosphate, pH 6.8. The pass-through and a wash with one column-volume (20 ml) of buffer are pooled.

Affinity Chromatography: An affinity matrix for purification of the desaturase is prepared by reacting highly purified E. coli ACP, with CNBr-activated Sepharose 4B (Sigma). ACP (120 mg) is reduced by treatment with 1 mM dithiothreitol for 30 min on ice, and then desalted on Sephadex G-10 (Pharmacia) equilibrated with 0.1M sodium bicarbonate, pH 6.0. The treated ACP (20 ml, 6 mg/ml) is then mixed with 20 ml of CNBr-activated Sepharose 4B swollen in 0.1M sodium bicarbonate, pH 7.0, and the mixture is allowed to stand at 4° C. for one day. The gel suspension is then centrifuged, washed once with 0.1M sodium bicarbonate, pH 7.0, and then treated with 40 ml 0.1M glycine, pH 8.0, for 4 hours at room temperature to block unreacted sites. The gel is then washed for five cycles with alternating 50 ml volumes of 0.5M NaCl in 0.1M sodium acetate, pH 4.0, and 0.5M NaCl in 0.1M sodium bicarbonate, pH 6.5, to remove non-covalently bound ligand. The gel is loaded into a column (1.5×11.2 cm) and equilibrated in 20 mM potassium phosphate, pH 6.8.

The combined fractions from the DE-52 column are applied to the column, which is subsequently washed with one column volume (20 ml) of the equilibration buffer, and then with 2.5 column volumes (50 ml) of 300 mM potassium phosphate, pH 6.8. Fractions are assayed for protein using the BCA Protein Assay Reagent (Pierce, Rockford, Ill.) to make sure that all extraneous protein has been eluted. Active Δ-9 desaturase is eluted from the column with 600 mM potassium phosphate, pH 6.8. Active fractions are analyzed by polyacrylamide gel electrophoresis in sodium dodecyl sulfate (SDS-PAGE) on 0.75 mm thick 8×12 cm mini-gels according to the method of Laemmli (Nature (1970) 227:680). The running gel contains 10% acrylamide in a 30/0.8 ratio of acrylamide to cross-linker bis-acrylamide. Those fractions containing a predominant band at approximately 43 kD are pooled and stored frozen at −70° C. until final purification. The yield from 50 g of seed tissue is approximately 60 µg of protein as measured by amino acid analysis.

Further purification as described in Example 2 or Example 3 is then applied to the fractions pooled from the ACP-Sepharose column separation.

Example 2

In this example, a protocol for the final purification of C. tinctorius desaturase is described. Seeds are treated in accordance with Example 1.

Reverse-Phase HPLC: Fractions from the ACP-Sepharose column are pooled and applied to a Vydac C4 reverse-phase column (0.45×15 cm) equilibrated in 0.1% TFA, 7% acetonitrile. After a 10 min wash with 0.1% TFA, the column is eluted with a gradient of increasing acetonitrile (7%-70% v/v) in 0.1% TFA over a period of 45 min. The flow rate is 0.5 ml/min throughout. Eluting components are monitored by absorbance at 214 nm. Δ-9 desaturase elutes at about 42 min. (approximately 50% acetonitrile); the major contaminant protein remaining from ACP-affinity chromatography elutes at about 28 min. (approximately 30% acetonitrile). The substantially homogeneous desaturase, which is no longer active, is identified by SDS-PAGE, in which it exhibits a single band corresponding to a molecular weight of approximately 43 kD. The quantity of desaturase protein in the sample may be determined by amino acid analysis.

Example 3

In this example, a protocol for the final purification of C. tinctorius desaturase is described. Seeds are treated in accordance with Example 1.

Reduction and Alkylation: Protein is precipitated out of the pooled fraction solutions recovered from the ACP-Sepharose column with 10% (w/v) trichloroacetic acid, washed with cold (−20° C.) acetone, and resuspended in 1 ml 500 mM Tris-HCl, pH 8.6, containing 6M guanidine-HCl, 10 mM EDTA, and 3.2 mM dithiothreitol. After 2 hours, 3.52 µmol [$^3$H]-iodoacetic acid (64 µCi/µmol, New England Nuclear) is added, and the reaction is allowed to proceed at room temperature in the dark for 2 hours, at which time the reaction is terminated by addition of 1 µl (15 µmol) β-mercaptoethanol. The sample is then re-precipitated with 10% (w/v) trichloroacetic acid, and the pellet again washed with cold (−20° C.) acetone and resuspended in Laemmli's SDS-sample buffer (Nature (1970) 227:680).

SDS-Polyacrylamide Gel Electrophoresis: The resulting sample is boiled for 5 min. and then applied to a 1.5 mm thick, 8×12 cm, SDS-polyacrylamide mini-gel prepared as described by Laemmli, supra. The running gel contains 17.5% acrylamide in a 30:0.13 ratio of acrylamide to cross-linking bis-acrylamide. Separation is achieved by electrophoresis at 15 mA, for 2 hours at 4° C.

Blotting from SDS-gels to PVDF Membrane: Proteins are recovered from the gel by electroblotting at 5 mA/cm$^2$ to a four-layer sandwich of polyvinylidenedifluoride (PVDF) membrane for 2 h at 4° C. in a buffer containing 10 mM CAPS ("3-[(cyclohexylamino]-1-propane-sulfonic acid"), pH 11. The membranes must be wetted in 50% methanol, prior to exposure to the blotting buffer. After blotting, the membrane layers are stained for 1-2 min. in 0.02% Coomassie Blue in 50% methanol, and then destained in 50% methanol. The desaturase is identified as a band corresponding to a molecular weight of about 43 kD; the major contaminant runs at or near the dye front of the gel corresponding to a molecular weight less than 20 kD.

The desaturase band on the PVDF membrane may be applied directly to the Edman sequencer (Applied Biosystems Model 477A) for determination of the N-terminal sequence of the intact protein, or for more extensive sequence determination, may be eluted from the membrane in 40% acetonitrile to recover pure desaturase in solution. Acetonitrile is removed from the eluted desaturase by evaporation on a Speed-Vac (Savant; Farmingdale, N.Y.), and the substantially homogeneous Δ-9 desaturase is resuspended in an appropriate buffer for subsequent proteolytic digestion as described in Example 4. The quantity of desaturase protein present may be determined by amino acid analysis.

Alternatively, if the sample is to be digested with trypsin or gluc protease to generate peptides for amino acid sequence analysis, proteins may be electroblotted to nitrocellulose membranes and stained with Ponceau or amido black.

Example 4

In this example, a method for the determination of the amino acid sequence of a desaturase is described.

Reduction and Alkylation: Substantially homogenous stearoyl-ACP desaturase (See, Example 2) is reduced and alkylated with [$^3$H]-iodoacetic acid (See, Example 3), except that the final acetone-washed pellet is resuspended in the appropriate buffer for subsequent proteolysis. Reduction and alkylation assures complete denaturation of the protein so that complete proteolysis can occur. The sample may be alkylated with radiolabeled iodoacetamide or with 4-vinylpyridine instead of [$^3$H]-iodoacetic acid in substantially the same manner. Use of iodoacetic acid affords an alkylated sample with greater solubility, which is advantageous in subsequent sample manipulation.

Proteolysis: Substantially pure alkylated samples are digested with endoproteinase lysC. The sample is resuspended in 100 µl of 25 mM Tris-HCl, pH 8.8, containing 1 mM EDTA. Endoproteinase lysC is added to the sample in a protease/desaturase ratio of 1/50 (w/w). Digestion is allowed to proceed at room temperature for 8 hours, at which time another equal amount of protease is added. After 18 more hours, 1 µl of concentrated HCl is added to stop proteolysis, and the sample is applied directly to a Vydac C18 reverse-phase column (0.2×15 cm) equilibrated in 7% acetonitrile (v/v) in 0.1 mM sodium phosphate, pH 2.2. After washing for 20 min with the equilibration buffer, peptides are eluted with a gradient in acetonitrile (7-70%, v/v) over 120 min. Flow rate is 50 µl/min, throughout. Eluting components are monitored by absorbance at 214 nm, and individual peptide peaks are collected as separate fractions. The peptide fractions are further purified by application to a second Vydac C18 reverse-phase column (0.2×15 cm) equilibrated in 7% (v/v) acetonitrile in 0.1% (v/v) trifluoroacetic acid. Again, after a 20 min wash with equilibration buffer, the substantially pure peptides are eluted with a gradient (7-70%, v/v) of acetonitrile in 0.1% trifluoroacetic acid over 120 min. The flow rate is 50 µl/min, throughout. Eluting components are monitored by absorbance at 214 nm, and individual peptide peaks are collected as separate fractions. These substantially pure peptides are applied directly to the Edman sequencer (Applied Biosystems, Model 477A) for amino acid sequence analysis. Alternatively, peptide fraction from the first HPLC purification in phosphate buffer, or from a single chromatography step in trifluoroacetic acid buffer, may be applied directly to the sequencer, but these fractions, in many cases, are not substantially pure and yield mixed or ambiguous sequence information.

Other proteases may be used to digest desaturase, including but not limited to trypsin, gluC, and aspN. While the individual digest buffer conditions may be different, the protocols for digestion, peptide separation, purification, and sequencing are substantially the same as those outlined for the digestion with lysC. Alternatively, desaturase may be digested chemically using cyanogen bromide (*Gross Methods Enzymol* (1967) 11:238-255 or Gross and Witkop *J. Am. Chem. Soc.* (1961) 83:1510), hydroxylamine (Bornstein and Balian *Methods Enzymol.* (1977) 47:132-745), iodosobenzoic acid (Inglis *Methods Enzymol.* (1983) 91:324-332), or mild acid (Fontana et al., *Methods Enzymol.* (1983) 91:311-317), as described in the respective references.

Fragments generated from these digestion steps of *C. tinctorius* desaturase are presented in FIG. 1 and as SEQ ID NOS: 1-11.

Example 5

In this example, the preparation of a plant embryo cDNA bank, using the methods as described in Alexander, et al. (*Methods in Enzymology* (1987) 154:41-64) and the screening of the bank to obtain a desaturase cDNA clone is described.

*C. tinctorius*: A plant embryo cDNA library may be constructed from poly(A)+ RNA isolated from *C. tinctorius* embryos collected at 14-17 days post-anthesis. Poly(A)+ RNA is isolated from polyribosomes by a method initially described by Jackson and Larkins (*Plant Physiol.* (1976) 57:5-10) as modified by Goldberg et al. (*Developmental Biol.* (1981) 83:201-217).

The plasmid cloning vector pCGN1703, derived from the commercial cloning vector Bluescribe M13– (Stratagene Cloning Systems; San Diego, Calif.), is made as follows. The polylinker of Bluescribe M13– is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with synthetic complementary oligonucleotides having the sequences 5' CGGATCCACTG-CAGTCTAGAGGGCCCGGGA 3' (SEQ ID NO: 30) and 5' AATTTCCCGGGCCCTCTAGACTGCAGTG-GATCCGAGCT 3' (SEQ ID NO: 31). These sequences are inserted to eliminate the EcoRI site, move the BamHI site onto the opposite side of the SstI (also, sometimes referred to as "SacI" herein) site found in Bluescribe, and to include new restriction sites PstI, XbaI, ApaI, SmaI. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang sticky-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI sticky-end at one end and a G-tail at the other. This complex is cyclized using the annealed synthetic cyclizing linker, 5'-GATC-CGCGGCCGCGAATTCGAGCTCCCCCCCCCC-3' and 3'-GCGCCGGCGCTTAAGCTCGA-5'which has a BamHI sticky-end and a C-tail end. Following ligation and repair the circular complexes are transformed into E. coli strain DH5α (BRL; Gaithersburg, Md.) to generate the cDNA library. The C. tinctorius embryo cDNA bank contains between $3\times10^6$ and $5\times10^6$ clones with an average cDNA insert size of approximately 1000 base pairs.

Probe production Including PCR Reactions: Two regions of amino acid sequence (Example 4) with low codon degeneracy are chosen from opposite ends of peptide sequence "Fragment F2" (SEQ ID NO:2) for production of a probe for the plant desaturase cDNA. Two sets of mixed oligonucleotides are designed and synthesized for use as forward (SEQ ID NOS: 21-24) and reverse (SEQ ID NOS: 25-26) primers, respectively, in the polymerase chain reaction (Saiki et al., Science (1985) 230:1350-1354; Oste, Biotechniques (1988) 6:162-167). See, FIG. 6. All oligonucleotides are synthesized on an Applied Biosystems 380A DNA synthesizer.

Probes to C. tinctorius desaturase may be prepared using the peptide sequence "Fragment 2" (SEQ ID NO: 2) identified in FIG. 1. Four types of forward primers were synthesized and labeled 13-1, 13-2, 13-3, and 13-4 (SEQ ID NOS: 21-24, respectively). Two groups of reverse primers were synthesized and designated 13-5A and 13-6A (SEQ ID NOS: 25-26, respectively). The primer sequences are shown in FIG. 6. These oligonucleotide groups have a redundancy of 64 or less and contain either 20 or 17 bases of coding sequence along with flanking restriction site sequences for HindIII or EcoRI. Based on the intervening amino acid sequence between the primer regions on peptide "Fragment 2" (SEQ ID NO: 2) the PCR product is expected to contain 107 base pairs.

Polymerase chain reaction is performed using the cDNA library DNA as template and the possible eight combinations of the four forward and two reverse oligonucleotides as primers in a Perkin-Elmer/Cetus DNA Thermal Cycler (Norwalk, Conn.) thermocycle file 1 min. 94° C., 2 min. 42° C., 2 min rise from 42°-72° C. for 30 cycles, followed by the step cycle file without step rises, 1 min. 94° C., 2 min. 42° C., 3 min. 72° C. with increasing 15 sec extensions of the 72° C. step for 10 cycles, and a final 10 min. 72° C. extension.

The product of the 13-4 forward primer (SEQ ID NO: 24) and the 13-5A reverse primer (SEQ ID NO: 25) reaction was ethanol precipitated and then digested with HindIII and EcoRI, the resulting fragment was subcloned into pUC8 (Vieira and Messing, Gene (1982) 19:259-268). Minipreparation DNA (Maniatis et al., Molecular_Cloning: A Laboratory Manual (1982) Cold Harbor Laboratory, New York) of one clone was sequenced by Sanger dideoxy sequencing (Sanger et al., Proc. Nat. Acad. Sci. USA (1977) 74:5463-5467) using the M13 universal and reverse primers. Translation of the resulting DNA sequence results in a peptide sequence that exactly matches the amino acid sequence in peptide "Fragment F2" (SEQ ID NO: 2).

An exact 50 base oligonucleotide designated DESAT-50 is synthesized to match the sequence of the PCR reaction product from the first valine residue to the last tyrosine residue.

The probe DSAT-50 5'-GTAAGTAGGTAGGGCTTC-CTCTGTAATCATATCTCCAACCAAAACAACAA-3' (SEQ ID NO: 32) is used to probe the C. tinctorius embryo cDNA library.

Library Screen

The C. tinctorius embryo cDNA bank is moved into the cloning vector lambda gt10 (Stratagene Cloning Systems) by digestion of total cDNA with EcoRI and ligation to lambda gt10 DNA digested with EcoRI. The titer of the resulting library was ~$5\times10^5$/ml. The library is then plated on E. coli strain C600 (Huynh, et al., DNA Cloning Vol. 1 Eds. Glover D.M. IRL Press Limited: Oxford England, pp. 56, 110) at a density of 5000 plaques/150 mm NZY ("NZYM" as defined in Maniatis et al. supra) agar plate to provide over 45,000 plaques for screening. Duplicate lifts are taken of the plaques using NEN Colony Plaque Screen filters by laying precut filters over the plates for ~1 minute and then peeling them off. The phage DNA is immobilized by floating the filters on denaturing solution (1.5M NaCl, 0.05M NaOH) for 1 min., transferring the filters to neutralizing solution (1.5M NaCl, 0.15M Tris-HCl pH 8.0) for 2 min. and then to 2×SSC (1×SSC=0.15M NaCl; 0.015M Na citrate) for 3 min., followed by air drying. The filters are hybridized with $^{32}$p end-labeled DSAT-50 oligonucleotide (SEQ ID NO: 32) (BRL 5' DNA Terminus Labeling System) by the method of Devlin et al., (DNA (1988) 7:499-807) at 42° C. overnight, and washed for 30 min. at 50° C. in 2×SSC, 0.5% SDS and then twice for 20 min. each at 50° C. in 0.1×SSC, 0.5% SDS. Filters are exposed to X-ray film at −70° C. with a Dupont Cronex intensifying screen for 48 hours.

Clones are detected by hybridization with the DSAT-50 oligonucleotide and plaque purified. The complete nucleotide sequence (SEQ ID NO: 12) of the cDNA insert of a clone, pCGN2754, and a partial restriction map thereof are presented in FIGS. 2 and 7A, respectively. The cDNA insert includes 1533 bases plus a poly(A) track at the 3' end of 100-200 bases. The open reading frame for the desaturase begins at the first ATG (nucleotide 106) from the 5' end and stops at nucleotide 1294. The translated amino acid sequence is presented in FIG. 2 and SEQ ID NO: 13. The open reading frame includes a 33 amino acid transit peptide not found in the amino acid sequence of the mature protein. The N-terminus of the protein begins at the alanine immediately following the NcoI site (nucleotide 202) indicating the site of the transit peptide processing.

Example 6

In this example, expression of a plant desaturase in a prokaryote is described.

Desaturase Expression Construct in E. Coli

A plasmid for expression of desaturase activity in E. coli is constructed as follows. The desaturase cDNA clone pCGN2754 is digested with HindIII and SalI and ligated to pCGN2016 (a chloramphenicol resistant version of Bluescript KS−) digested with HindIII and XhoI. The resulting plasmid is pCGN1894.

pCGN2016 is prepared by digesting pCGN565 with HhaI, and the fragment containing the chloramphenicol resistance gene is excised, blunted by use of mung bean nuclease, and inserted into the EcoRV site of Bluescript KS- (Stratagene: La Jolla, Calif.) to create pCGN2008. The chorampheicol resistance gene of pCGN2008 is removed by EcoRI/HindIII digestion. After treatment with Klenow enzyme to blunt the ends, the fragment is ligated to DraI digested Bluescript KS−. A clone that has the DraI fragment containing ampicillin resistance replaced with the chloramphenicol resistance is chosen and named pCGN2016.

pCGN565 is a cloning vector based on pUC12-cm (K. Buckley Ph.D. Thesis, Regulation and expression of the phi X174 lysis gene, University of California, San Diego, 1985), but contains pUC18 linkers (Yanisch-Perron, et al., *Gene* (1985) 53:103-119).

The fragment containing the mature coding region of the Δ-9 desaturase, 3'-noncoding sequences and poly(A) tails is subcloned from pCGN1894 digested with NcoI and Asp718 into pUC120, an *E. coli* expression vector based on pUC118 (Vieira and Messing, *Methods in Enzymology* (1987) 153:3-11) with the lac region inserted in the opposite orientation and an NcoI site at the ATG of the lac peptide (Vieira, J. PhD. Thesis, University of Minnesota, 1988). The *E. coli* desaturase expression plasmid is designated pCGN3201. The desaturase sequences are inserted such that they are aligned with the lac transcription and translation signals.

Expression of Desaturase in *E.coli*

Single colonies of *E. coli* strain 7118 (Maniatis et al., supra) containing pUC120 or pCGN3201 are cultured in 80 mls each of ECLB broth, 300 mg/L penicillin. The cells are induced by the addition of 1 mM IPTG. Cells are grown overnight (18 hrs) at 37° C.

Eighty mls of overnight cultures of *E. coli* (induced and uninduced) containing pUC120 or pCGN3201 are centrifuged at 14,800×g for 15 min. The pelleted cells are resuspended in 3 mls 20 mM phosphate buffer, pH 6.8. Resuspended cells were broken in a french press at 16,000 psi. Broken cell mixtures are centrifuged 5000×g for 5 min. 100 µl of each supernatant is applied to a G-25 Sephadex gel filtration centrifugal column (Boehringer Mannheim Biochemicals), equilibrated in 20 mM phosphate buffer pH 6.8. Columns are spun for 4 min at 5000×g. Effluent was collected and used as enzyme source in the desaturase assay.

Desaturase activity is assayed as described in Example 1. Both pUC120-containing, IPTG-induced cells and uninduced cells do not express detectable stearoyl-ACP desaturase activity. The pCGN3201 IPTG-induced extract contains 8.22 nmol/min of desaturase activity. pCGN3201 uninduced extracts contains 6.45 nmol/min of activity. The pCGN3201 IPTG-induced extract shows 21.5% more activity than the uninduced pCGN3201 extract.

Detection of Induced Protein in *E. coli.*

Extracts of overnight cultures of *E. coli* strain 7118 (Maniatis et al. supra ) containing pCGN3201 or pUC120 grown in ECLB containing 300 mg/L penicillin induced with 1 mM IPTG are prepared as follows. 1.5 ml of overnight culture grown shaking at 37° C. are pelleted in Eppendorf tubes for 10 min at 10-13,000 µg. Pellets are resuspended in 150 ul SDS sample buffer (0.05M Tris-HCl, pH 6.8, 1% SDS, 5% β-mercaptoethanol, 10% glycerol and 0.005% bromophenol blue) and boiled for 10 min. 25 µl of each sample are electrophoresed on a 10% polyacrylamide gel (Laemmli, *Nature* (1970) 227:680) at 25 mA for 5 hours. Gels are stained in 0.05% Coomassie Brilliant Blue, 25% isopropanol and 10% acetic acid and destained in 10% acetic acid and 10% isopropanol. A band is detected at a position just below the 43,000 MW protein marker (SDS PAGE standard, Low molecular weight, BioRad, Richmond Calif.) in the pCGN3201 extracts that is not present in the pUC120 extracts. This is the approximate molecular weight of mature desaturase protein.

Requirement for Spinach Ferredoxin

Stearoyl-ACP desaturase can also be expressed in *E. coli* by subcloning into the *E. coli* expression vector pET8c (Studier, et al., *Methods Enzymol*. (1990) 185:60-89). The mature coding region (plus an extra Met codon) of the desaturase cDNA with accompanying 3'-sequences is inserted as an NcoI-SmaI fragment into pET8c at the NcoI and BamHI sites (after treatment of the BamHI site with Klenow fragment of DNA polymerase to create a blunt end) to create pCGN3208. The plasmid pCGN3208 is maintained in *E. coli* strain BL21 (DE3) which contains the T7 polymerase gene under the control of the isopropyl-b-D-thiogalactopyranoside (IPTG)-inducible lacUV5 promoter (Studier et al., supra).

*E. coli* cells containing pCGN3208 are grown at 37° C. to an $OD_{595}$ of ~0.7 in NZY broth containing 0.4% (w/v) glucose and 300 mg/liter penicillin, and then induced for 3 hours with 0.4 mM IPTG. Cells are pelleted from 1 ml of culture, dissolved in 125 µl of SDS sample buffer (10) and heated to 100° C. for 10 min. Samples are analyzed by SDS polyacrylamide gel electrophoresis at 25 mA for 5 h. Gels are stained in 0.05% Coomassie Brilliant Blue, 25% (v/v) isopropanol and 10% (v/v) acetic acid. A band is detected at a position just below the 43,000 MW protein marker (SDS PAGE standard, Low Molecular Weight, BioRad, Richmond, Calif.) in the pCGN3208 extract that is not present in the pET8c extracts. This is the approximate molecular weight of mature desaturase protein.

For activity assays, cells are treated as described above and extracts are used as enzyme source in the stearoyl-ACP desaturase assay as described in Example 1. The extract from IPTG-induced pCGN3208 cells contains 8.61 nmol/min/mg protein of desaturase activity. The extract from pCGN3208 uninduced cells contains 1.41 nmol/min/mg protein of desaturase activity. The extract from pCGN3208 induced cells, thus has approximately 6-fold greater activity than the extract from uninduced pCGN3208 cells. Extracts from both induced and uninduced cells of pET8c do not contain detectable stearoyl-ACP desaturase activity.

Samples are also assayed as described in Example 1, but without the addition of spinach ferredoxin, to determine if the *E. coli* ferredoxin is an efficient electron donor for the desaturase reaction. Minimal activity is detected in *E. coli* extracts unless spinach ferredoxin is added exogenously.

Example 7

In this example, the preparation of an ACP expression cassette containing a plant desaturase in a binary vector suitable for plant transformation is described.

ACP Expression Cassette

An expression cassette utilizing 5'-upstream sequences and 3'-downstream sequences obtainable from *B. campestris* ACP gene can be constructed as follows.

A 1.45 kb XhoI fragment of Bcg 4-4 (FIG. 9 and SEQ ID NO: 28) containing 5'-upstream sequences is subcloned into the cloning/sequencing vector Bluescript+ (Stratagene Cloning Systems, San Diego, Calif.). The resulting construct, pCGN1941, is digested with XhoI and ligated to a chloramphenicol resistant Bluescript M13+ vector, pCGN2015 digested with XhoI. pCGN2015 is prepared as described for pCGN2016 (See, Example 6) except that the EcoRI/HindIII "chloramphenicol", fragment isolated from pCGN2008 is ligated with the 2273 bp fragment of Bluescript $KS^+$ (Stratagene; La Jolla, Calif.) isolated after digestion with DraI. This alters the antibiotic resistance of the plasmid from penicillin resistance to chloramphenicol resistance. The chloramphenicol resistant plasmid is pCGN1953.

3'-sequences of Bcg 4-4 are contained on an SstI/BglII fragment cloned in the SstI/BamHI sites of M13 Bluescript+ vector. This plasmid is named pCGN1940. pCGN1940 is modified by in vitro site-directed mutagenesis (Adelman et al., *DNA* (1983) 2:183-193) using the synthetic oligonucleotide 5'-CTTAAGAAGTAACCCGGGCTGCAGTTT- TAGTATTAAGAG-3' (SEQ ID NO: 33) to insert SmaI and PstI restriction sites immediately following the stop codon of the reading frame for the ACP gene 18 nucleotides from the SstI site. The 3'-noncoding sequences from this modified plasmid, pCGN1950, are moved as a PsI-SmaI fragment into pCGN1953 cut with PstI and SmaI. The resulting plasmid pCGN1977 comprises the ACP expression cassette with the unique restriction sites EcoRV, EcoRI and PstI available between the 1.45 kb 5' and 1.5 kb of 3'-noncoding sequences (SEQ ID NO: 28) for the cloning of genes to be expressed under regulation of these ACP gene regions.

Desaturase Expression in Plants

Desaturase cDNA sequences from pCGN2754 are inserted in the ACP expression cassette, pCGN1977, as follows. pCGN2754 is digested with HindIII (located 160 nucleotides upstream of the start codon) and Asp718 located in the polylinker outside the poly(A) tails. The fragment containing the coding region for desaturase was blunt-ended using DNA polymerase I and ligated to pCGN1977 digested with EcoRV. A clone containing the desaturase sequences in the sense orientation with respect to the ACP promoter is selected and called pCGN1895. This expression cassette may be inserted into a binary vector, for example, for *Agrobacterium*-mediated transformation, or employed in other plant transformation techniques.

Binary Vector and *Agrobacterium* Transformation

The fragment containing the pCGN1895 expression sequences ACP 5'/desaturase/ACP 3' is cloned into a binary vector pCGN1557 (described below) for *Agrobacterium* transformation by digestion with Asp718 and XbaI and ligation to pCGN1557 digested with Asp718 and XbaI. The resulting binary vector is called pCGN1898.

pCGN1898 is transformed into *Agrobacterium tumefaciens* strain EHA101 (Hood, et al., *J. Bacteriol.* (1986) 168: 1291-1301) as per the method of Holsters, et al., *Mol. Gen. Genet.* (1978) 163:181-187.

RNA blot analysis of seeds (T2) from T1 plants show the presence of a mRNA species for the inserted *C. tinctorius* desaturase, but the amount of message is low compared to endogenous levels of mRNA for the *Brassica* desaturase, suggesting that the expression levels were insufficient to significantly increase the amount of desaturase enzyme above that normally present. This is consistent with the negative results from oil, desaturase activity and Western blot analyses.

Construction of pCGN1557 pCGN1557 (McBride and Summerfelt, *Plant Molecular Biology* (1990) 14(2):269-276) is a binary plant transformation vector containing the left and right T-DNA borders of *Agrobacterium tumefaciens* octopine Ti-plasmid pTiA6 (Currier and Nester, supra, the gentamycin resistance-gene of pPH1JI (Hirsch and Beringer, supra), an *Agrobacterium rhizogenes* Ri plasmid origin of replication from pLJbB11 (Jouanin et al., supra), a 35S promoter-kanR-tml3' region capable of conferring kanamycin resistance to transformed plants, a ColE1 origin of replication from pBR322 (Bolivar et al., supra), and a lacZ' screenable marker gene from pUC18 (Yanish-Perron et al., supra).

There are three major intermediate constructs used to generate pCGN1557:

pCGN1532 (see below) contains the pCGN1557 backbone, the pRi plasmid origin of replication, and the ColE1 origin of replication.

pCGN1546 (see below) contains the CaMV35S5'-kan$^R$-tml3' plant selectable marker region.

pCGN1541b (see below) contains the right and left T-DNA borders of the *A. tumefaciens* octopine Ti-plasmid and the lacZ' region from pUC19.

To construct pCGN1557 from the above plasmids, pCGN1546 is digested with XhoI, and the fragment containing the CaMV 35S5'-kan$^R$-tml3' region is cloned into the XhoI site of pCGN1541b to give the plasmid pCGN1553, which contains T-DNA/left border/CaMV 35S5'-kanR-tml3'/lacZ'/T-DNA left border. pCGN1553 is digested with BglII, and the fragment containing the T-DNA/left border/CaMV35S5'-kan$^{R-tml3}$'/lacZ'/T-DNA left border region is ligated into BamHI-digested pCGN1532 to give the complete binary vector, pCGN1557.

pCGN1532

The 3.5 kb EcoRI-PstI fragment containing the gentamycin resistance gene is removed from pPh1JI (Hirsch and Beringer, *Plasmid* (1984) 12:139-141) by EcoRI-PstI digestion and cloned into EcoRI-PstI digested pUC9 (Vieira and Messing, *Gene* (1982) 19:259-268) to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al., *Gene* (1977) 2:95-113) to create pBR322Gm. pBR322Gm is digested with DraI and SphI, treated with Klenow enzyme to create blunt ends, and the 2.8 kb fragment cloned into the Ri origin-containing plasmid pLJbB11 (Jouanin et al., *Mol. Gen. Genet.* (1985) 201:370-374) which has been digested with ApaI and made blunt-ended with Klenow enzyme, creating pLHbB11Gm. The extra ColE1 origin and the kanamycin resistance gene are deleted from pLHbB11Gm by digestion with BamHI followed by self closure to create pGmB11. The HindII site of pGmB11 is deleted by HindIII digestion followed by treatment with Klenow enzyme and self closure, creating pGmB11-H. The PstI site of pGmB11-H is deleted by PstI digestion followed by treatment with Klenow enzyme and self closure, creating pCGN1532.

Construction of pCGN1546

The 35S promoter-tml3' expression cassette, pCGN986, contains a cauliflower mosaic virus 35S (CaMV35) promoter and a T-DNA tml 3'-region with multiple restriction sites between them. pCGN986 is derived from another cassette, pCGN206, containing a CaMV35S promoter and a different 3' region, the CaMV region VI 3'-end. The CaMV 35S promoter is cloned as an AluI fragment (bp 7144-7734) (Gardner et. al., *Nucl. Acids Res.* (1981) 9:2871-2888) into the HincII site of M13mp7 (Messing, et. al., *Nucl. Acids Res.* (1981) 9:309-321) to create C614. An EcoRI digest of C614 produced the EcoRI fragment from C614 containing the 35S promoter which is cloned into the EcoRI site of pUC8 (Vieira and Messing, *Gene* (1982) 19:259) to produce pCGN147.

pCGN148a containing a promoter region, selectable marker (KAN with 2 ATG's) and 3' region, is prepared by digesting pCGN528 with BglII and inserting the BamHI-BglII promoter fragment from pCGN147. This fragment is cloned into the BglII site of pCGN528 so that the BglII site is proximal to the kanamycin gene of pCGN528.

The shuttle vector used for this construct pCGN528, is made as follows: pCGN525 is made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141-1156). pCGN526 was made by inserting the BamHI fragment 19 of pTiA6 (Thomashow et. al., *Cell* (1980) 19:729-739), modified with XhoI linkers inserted into the SmaI site, into the BamHI site of pCGN525. pCGN528 is obtained by deleting the small XhoI fragment from pCGN526 by digesting with XhoI and religating.

pCGN149a is made by cloning the BamHI-kanamycin gene fragment from pMB9KanXXI into the BamHI site of pCGN148a. pMB9KanXXI is a pUC4K variant (Vieira and Messing, Gene (1982) 19:259-268) which has the XhoI site missing, but contains a functional kanamycin gene from Tn903 to allow for efficient selection in Agrobacterium.

pCGN149a is digested with HindIII and BamHI and ligated to pUC8 digested with HindIII and BamHI to produce pCGN169. This removes the Tn903 kanamycin marker. pCGN565 (see pCGN2016 description) and pCGN169 are both digested with HindIII and PstI and ligated to form pCGN203, a plasmid containing the CaMV 35S promoter and part of the 5'-end of the Tn5 kanamycin gene (up to the PstI site, Jorgenson et. al., (1979), supra). A 3'-regulatory region is added to pCGN203 from pCGN204 (an EcoRI fragment of CaMV (bp 408-6105) containing the region VI 3' cloned into pUC18 (Yanisch-Perron, et al., Gene (1985) 33:103-119) by digestion with HindIII and PstI and ligation. The resulting cassette, pCGN206, is the basis for the construction of pCGN986.

The pTiA6 T-DNA tml 3'-sequences are subcloned from the Bam19 T-DNA fragment (Thomashow et al., (1980) supra) as a BamHI-EcoRI fragment (nucleotides 9062 to 12,823, numbering as in Barker et al., Plant Mol. Biol. (1982) 2:335-350) and combined with the pACYC184 (Chang and Cohen (1978), supra) origin of replication as an EcoRI-HindIII fragment and a gentamycin resistance marker (from plasmid pLB41), obtained from D. Figurski) as a BamHI-HindIII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give pCGN971. The BamHI site of pCGN971 is changed to an EcoRI site using linkers. The resulting EcoRI-SacI fragment containing the tml 3' regulatory sequences is joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligation with SalI linkers. The final expression cassette pCGN986 contains the CaMV 35S promoter followed by two SalI sites, an XbaI site, BamHI, SmaI, KpnI and the tml 3' region (nucleotides 11207-9023 of the T-DNA) The 35S promoter-tml 3' expression cassette, pCGN986 is digested with HindIII. The ends are filled in with Klenow polymerase and XhoI linkers added. The resulting plasmid is called pCGN986X. The BamHI-SacI fragment of pBRX25 (see below) containing the nitrilase gene is inserted into BamHI-SacI digested pCGN986X yielding pBRX66.

Construction of pBRX25 is described in U.S. Pat. No. 4,810,648, which is hereby incorporated by reference. Briefly, the method is as follows: The nucleotide sequence of a 1212-bp PstI-HincII DNA segment encoding the bromoxynil-specific nitrilase contains 65-bp of 5' untranslated nucleotides. To facilitate removal of a portion of these excess nucleotides, plasmid pBRX9 is digested with PstI, and treated with nuclease Bal31. BamHI linkers are added to the resulting ends. BamHI-HincII fragments containing a functional bromoxynil gene are cloned into the BamHI-SmaI sites of pCGN565. The resulting plasmid, pBRX25, contains only 11 bp of 5' untranslated bacterial sequence. pBRX66 is digested with PstI and EcoRI, blunt ends generated by treatment with Klenow polymerase, and XhoI linkers added. The resulting plasmid pBRX68 now has a tml 3' region that is approximately 1.1 kb. pBRX68 is digested with SalI and SacI, blunt ends generated by treatment with Klenow polymerase and EcoRI linkers added. The resulting plasmid, pCGN986XE is a 35S promoter—tml 3' expression cassette lacking the nitrilase gene.

The Tn5 kanamycin resistance gene is then inserted into pCGN986XE. The 1.0 kb EcoRI fragment of pCGN 1536 (see pCGN 1547 description) is ligated into pCGN986XE digested with EcoRI. A clone with the Tn5 kanamycin resistance gene in the correct orientation for transcription and translation is chosen and called pCGN1537b. The 35S promoter Kan$^R$-tml 3' region is then transferred to a chloramphenicol resistant plasmid backbone. pCGN786, (a pUC-CAM based vector with the synthetic oligonucleotide 5' GGAATTCGTCGACAGATCTCTG CAGCTCGAGG-GATCCAAGCTT 3' (SEQ ID NO: 34) containing the cloning sites EcoRI, SalI, BglII, PstI, XhoI, BamHI, and HindIII inserted into pCGN566, pCGN566 contains the EcoHI-HindIII linker of pUC18 inserted into the EcoRI-HindIII sites of pUC13-cm (K. Buckler (1985) supra) ) is digested with XhoI and the XhoI fragment of pCGN1537b containing the 35S promoter—Kan$^R$-tml 3' region is ligated in. The resulting clone is termed pCGN 1546.

pCGN565RBα2X (see below) is digested with BglII and XhoI, and the 728 bp fragment containing the T-DNA right border piece and the lacZ' gene is ligated with BglII-XhoI digested pCGN65ΔKX–S+K (see below), replacing the BglII-XhoI right border fragment of pCGN65ΔKX–S+K. The resulting plasmid, pCGN65α2X contains both T-DNA borders and the lacZ' gene. The ClaI fragment of pCGN65α2X is replaced with an XhoI site by digesting with ClaI blunting the ends using the Klenow fragment, and ligating with XhoI linker DNA, resulting in plasmid pCGN65α2XX. pCGN65α2XX is digested with BglII and EcoRV, treated with the Klenow fragment of DNA polymerase I to create blunt ends, and ligated in the presence of BglII linker DNA, resulting in pCGN65α2XX'. pCGN65α2XX' is digested with BglII and ligated with BglII digested pCGN1538 (see below), resulting in pCGN1541a, which contains both plasmid backbones. pCGN1541a is digested with XhoI and religated. Ampicillin resistant, chloramphenicol sensitive clones are chosen, which lack the pACYC 184-derived backbone, creating pCGN 1541b.

pCGN1538 is generated by digesting pBR322 with EcoRI and PvuII, treating with Klenow to generate blunt ends, and ligating with BglII linkers. pCGN1538 is ampicillin resistant, tetracycline sensitive.

pCGN65ΔKX–S+K pCGN501 is constructed by cloning a 1.85 kb EcoRI-XhoI fragment of pTiA6 (Currier and Nester, J. Bact. (1976) 126: 157-165) containing bases 13362-15208 (Barker et al., Plant Mo. Biol. (1983) 2:335-350) of the T-DNA (right border), into EcoRI-SalI digested M13mp9 (Vieira and Messing, Gene (1982) 19:259-268). pCGN502 is constructed by cloning a 1.6 kb HindIII-SmaI fragment of pTiA6, containing bases 602-2212 of the T-DNA (left border), into HindIII-SmaI digested M13mp9. pCGN501 and pCGN502 are both digested with EcoRI and HindIII and both T-DNA-containing fragments cloned together into HindIII digested pUC9 (Vieira and Messing, Gene (1982) 19:259-268) to yield pCGN503, containing both T-DNA border fragments. pCGN503 is digested with HindIII and EcoRI and the two resulting HindIII-EcoRI fragments (containing the T-DNA borders) are cloned into EcoRI digested pHC79 (Hohn and Collins, Gene (1980) 11:291-298) to generate pCGN518. The 1.6 kb KpnI-EcoRI fragment from pCGN518, containing the left T-DNA border, is cloned into KpnI-EcoRI digested pCGN565 to generate pCGN580. The BamHI-BglII fragment of pCGN580 is cloned into the BamHI site of pACYC184 (Chang and Cohen, *J. Bacteriol*. (1978) 134: 1141-1156) to create pCGN51. The 1.4 kb BamHI-SphI fragment of pCGN60 containing the T-DNA right border fragment, is cloned into BamHI-SphI digested pCGN51 to create pCGN65, which contains the right and left T-DNA borders.

pCGN65 is digested with KpnI and XbaI, treated with Klenow enzyme to create blunt ends, and ligated in the presence of synthetic BglII linker DNA to create pCGN65ΔKX. pCGN65ΔKX is digested with SalI, treated with Klenow enzyme to create blunt ends, and ligated in the presence of synthetic XhoI linker DNA to create pCGN65ΔKX-S+X.

pCGN565RBα2X pCGN451 (see below) is digested with HpaI and ligated in the presence of synthetic SphI linker DNA to generate pCGN55. The XhoI-SphI fragment of pCGN55 (bp 13800-15208, including the right border, of *Agrobacterium tumefaciens* T-DNA; (Barker et al., *Gene* (1977) 2:95-113) is cloned into SalI-SphI digested pUC19 (Yanisch-Perron et al., *Gene* (1985) 53:103-119) to create pCGN60. The 1.4 kb HindIII-BamHI fragment of pCGN60 is cloned into HindIII-BamHI digested pSP64 (Promega, Inc.) to generate pCGN1039. pCGN1039 is digested with SmaI and NruI (deleting bp 14273-15208; (Barker et al., *Gene* (1977) 2:95-113) and ligated in the presence of synthetic BglII linker DNA creating pCGN1039ΔNS. The 0.47 kb EcoRI-HindIII fragment of pCGN1039ΔNS is cloned into EcoRI-HindIII digested pCGN565 to create pCGN565RB. The HindIII site of pCGN565RB is replaced with an XhoI site by digesting with HindIII, treating with Klenow enzyme, and ligating in the presence of synthetic XhoI linker DNA to create pCGN565RB-H+X.

pUC18 (Norrander et al., *Gene* (1983) 26:101-106) is digested with HaeII to release the lacZ' fragment, treated with Klenow enzyme to create blunt ends, and the lacZ'-containing fragment ligated into pCGN565RB-H+X, which had been digested with AccI and SphI and treated with Klenow enzyme in such a orientation that the lacZ' promoter is proximal to the right border fragment; this construct, pCGN565RBα2x is positive for lacZ' expression when plated on an appropriate host and contains bp 13990-14273 of the right border fragment (Barker et al., *Plant Mo. Biol*. (1983) 2:335-350) having deleted the AccI-SphI fragment (bp 13800-13990).

pCGN451 pCGN451 contains an ocs5'-ocs3' cassette, including the T-DNA right border, cloned into a derivative of pUC8 (Vieira and Messing, supra). The modified vector is derived by digesting pUC8 with HincII and ligating in the presence of synthetic linker DNA, creating pCGN416, and then deleting the EcoRI site of pCGN416 by EcoRI digestion followed by treatment with Klenow enzyme and self-ligation to create pCGN426.

The ocs5'-ocs3' cassette is created by a series of steps from DNA derived from the octopine Ti-plasmid pTiA6 (Currier and Nester, supra). To generate the 5'end, which includes the T-DNA right border, an EcoRI fragment of pTiA6 (bp 13362-16202 (the numbering is by Barker, et al., (*Plant Mol. Bio* (1983) 2:335-350) for the closely related Ti plasmid pTil5955)) is removed from pVK232 (Knauf and Nester, *Plasmid* (1982) 8:45) by EcoRI digestion and cloned into EcoRI digested pACYC184 (Chang and Cohen, supra) to generate pCGN15.

The 2.4 kb BamHI-EcoRI fragment (bp 13774-16202) of pCGN15 is cloned into EcoRI-BamHI digested pBR322 (Bolivar, et al., supra) to yield pCGN429. The 412 bp EcoRI-BamHI fragment (bp 13362-13772) of pCGN15 is cloned into EcoRI-BamHI digested pBR322 to yield pCGN407. The cut-down promoter fragment is obtained by digesting pCGN407 with XmnI (bp 13512), followed by resection with Bal31 exonuclease, ligation of synthetic EcoRI linkers, and digestion with BamHI. Resulting fragments of approximately 130 bp are gel purified and cloned into M13mp9 (Vieira and Messing, supra) and sequenced. A clone, I-4, in which the EcoRI linker has been inserted at bp 1362 between the transcription initiation point and the translation initiation codon is identified by comparison with the sequence of de Greve, et al., (*J. Mol. Appl. Genet*. (1982) 1:499-512). The EcoRI cleavage site is at position 13639, downstream from the mRNA start site. The 141 bp EcoRI-BamHI fragment of I-4, containing the cut-down promoter, is cloned into EcoRI-BamHI digested pBR322 to create pCGN428. The 141 bp EcoRI-BamHI promoter piece from pCGN428, and the 2.5 kb EcoRI-BamHI ocs5' piece from pCGN429 are cloned together into EcoRI digested pUC19 (Vieira and Messing, supra) to generate pCGN442, reconstructing the ocs upstream region with a cut-down promoter section.

To generate the ocs3' end, the HindIII fragment of pLB41 (D. Figurski, UC San Diego) containing the gentamycin resistance gene is cloned into HindIII digested pACYC184 (Chang and Cohen, supra) to create pCGN413b. The 4.7 kb BamHI fragment of pTiA6 (supra), containing the ocs3' region, is cloned into BamHI digested pBR325 (F. Bolivar, *Gene* (1978) 4:121-136) to create 33c-19. The SmaI site at position 11207 (Barker, supra) of 33c-19 is converted to an XhoI site using a synthetic XhoI linker, generating pCCG401.2. The 3.8 kb BamHI-EcoRI fragment of pCGN401.2 is cloned into BamHI-EcoRI digested pCGN413b to create pCGN419.

The ocs5'-ocs3' cassette is generated by cloning the 2.64 kb EcoRI fragment of pCGN442, containing the 5' region, into EcoRI digested pCGN419 to create pCNG446. The 3.1 kb XhoI fragment of pCGN446, having the ocs5' region (bp 13639-15208) and ocs3' region (bp 11207-12823), is cloned into the XhoI site of pCGN426 to create pCGN451.

Example 8

In this example, the preparation of a Bce-4 expression cassette containing a plant desaturase is described.

The desaturase cDNA clone from pCGN2754 prepared as described in Example 5, is modified by in vitro mutagenesis to insert restriction sites immediately upstream of the ATG start codon and downstream of the TGA stop codon. A single-stranded template DNA is prepared for the mutagenesis reaction from pCGN1894 (described in Example 6) as described by Messing, (*Methods in Enzymol*. (1983) 101:20-79). Synthetic oligonucleotides are synthesized on an Applied Biosystems 380A DNA synthesizer. The oligonucleotides used are 5'-CCATTTTTGATCTTCCTCGAGC-CCGGGCTGCAGTTCTTCTTCTTCTTG-3' (SEQ ID NO: 35) for the 5'mutagenesis and 5'-GCTCGTTTTTTTTTCTCTGCAGC-CCGGGCTCGAGTCACAGCTTCACC -3' (SEQ ID NO: 36) for the 3'-mutagenesis; both add PstI, SmaI and XhoI sites flanking the coding region. Both oligonucleotides are 5'-phosphorylated (BRL 5'-Terminus labelling kit) and used for mutagenesis with the pCGN1894 template by the procedure of Adelman et al. (*DNA* (1983) 2:183-193). Alternatively, the desired restriction sites may be inserted by PCR, using the 3' oligo described above (SEQ ID NO: 36) and another oligo, 5' ACTGACTGCAGCCCGGGCTCGAG-GAAGATCAAAAATGGCTCTTC 3' (SEQ ID NO: 37) for the 3' and 5' primers, respectively. The template in this polymerase chain reaction is DNA from pCGN1894. The XhoI fragment from the resulting clone can be subcloned into the Bce4 expression cassette, pCGN1870 (described below) at the unique XhoI site. This Bce4/desaturase expression cassette can then be inserted in a suitable binary vector, transformed into *Agrobacterium tumefaciens* strain EHA101 and used to transform plants as provided in Example 10.

Bce-4 Expression Cassette pCGN1870 is a Bce-4 expression cassette containing 5' and 3' regulatory regions of the Bce-4 gene and may be derived from the Bce-4 sequence found in pCGN1857, which was deposited with the ATCC on Mar. 9, 1990, and assigned accession number 68251, or by methods known to one skilled in the art from the sequence (SEQ ID NO: 27) provided in FIG. 8. The Bce 4 gene may be isolated as follows:

The ClaI fragment of pCGN1857, containing the Bce4 gene is ligated into ClaI digested Bluescript KS+ (Stratagene; La Jolla, Calif.), producing pCGN1864. Single stranded DNA is made from pCGN1864 and altered by in vitro mutagenesis using the oligonucleotides

```
BCE45P:
(5'GAGTAGTGAACTTCATGGATCCTCGAGGTCT  (SEQ ID NO: 38)
TGAAAACCTAGA3')
and

BCE43P:
(5'CAATGTCTTGAGAGATCCCGGGATCCTTAAC  (SEQ ID NO: 39)
AACTAGGAAAAGG3')
``` as described by Adelman et al. (*DNA* (1983) 2:183-193). The oligonucleotide BSCP2 (5'GTAAGACACGACTTATCGC-CACTG3') (SEQ ID NO: 40), complementary to a portion of Bluescript, is included in the reaction to improve the yield of double-stranded DNA molecules. The resulting plasmid, pCGN1866, contains XhoI and BamHI sites (from BCE45P) immediately 5' to the Bce4 start codon and BamHI and SmaI sites (from BCE43P) immediately 3' to the Bce4 stop codon. The ClaI fragment of pCGN1866, containing the mutagenized sequences, is inserted into the ClaI site of pCGN2016 (described in Example 6), producing pCGN1866C. The ClaI fragment of pCGN1866C is used to replace the corresponding wild-type ClaI fragment of PCGN1867 (described below) to produce pCGN1868. Bce4 coding sequences are removed by digestion of pCGN1868 with BamHI and recircularization of the plasmid to produce pCGN1870. The Bce4 expression cassette, pCGN1870, contains 7.4 kb of 5' regulatory sequence and 1.9 kb of 3' regulatory sequence derived from the Bce4 genomic clone separated by the cloning sites, XhoI, BamHI, and SmaI. Desaturase sequences in sense or anti-sense orientation may be inserted into the cassette via the cloning sites and the resulting construct may be employed in a plant transformation technique.

pCGN1867

The BamHI and SmaI sites of pUC18 are removed by BamHI-SmaI digestion and recircularizing of the plasmid, without repair of the ends, to produce pCGN1862 The PstI fragment of pCGN1857, containing the Bce4 gene, is inserted into the PstI site of pCGN1862 to produce pCGN1867.

Example 9

In this example, the preparation of a napin 1-2 expression cassette containing a plant desaturase is described.

Preparation of Desaturase Clone

The desaturase cDNA clone from pCGN2754 is prepared and modified as described in Example 8. The XhoI fragment from the resulting clone can be subcloned into the napin 1-2 expression cassette, pCGN1808 (described below) at the unique XhoI site. This napin 1-2/desaturase expression cassette can then be inserted into a suitable binary vector, transformed into *A. tumefaciens* strain EHA101 in a like manner as described in Example 7.

Alternatively, the desaturase safflower clone may be prepared such that restriction sites flank the translation start and stop sites, as described in Example 8, with the following modification. PCR was carried out according to manufacturer's instructions except for the initial annealing of the oligonucleotides to the template. The reaction mix was heated to 90° C. for 5 min, cooled to 37° C. over a one hour period, kept at 37° C. for 20 min and then subjected to standard PCR cycles. The PCR product was digested with PstI and ligated to pUC8 (Vieira and Messing (1982) *Gene* 19:2359-268) digested with PstI to produce pCGN3220. The NcoI/SacI fragment of pCGN3220 containing the pUC8 vector and the 5' and 3' sequences of the safflower desaturase cDNA was gel purified and ligated to the gel-purified cloned NcoI/SacI fragment from pCGN1894 (see Example 6). The resulting plasmid pCGN3222 contains safflower desaturase cDNA sequences partially from the cDNA clone and partially from the PCR. The regions obtained from the PCR were confirmed by DNA sequencing as being identical to the original cloned sequence.

Expression Cassettes

Napin 1-2 pCGN1808 Expression Cassette

An expression cassette utilizing 5' upstream sequences and 3' downstream sequences obtainable from *B. campestris* napin gene can be constructed as follows.

A 2.7 kb XhoI fragment of napin 1-2 (FIG. 10 and SEQ ID NO: 29) containing 5' upstream sequences is subcloned into pCGN789 (a pUC based vector the same as pUC119 with the normal polylinker replaced by the synthetic linker— 5'GGAATTCGTCGACAGATCTCTGCAGCTC-GAGGGATCCAAGCTT 3', SEQ ID NO: 41, (which represented the polylinker EcoRI, SalI, BglII, PstI, XhoI, BamHI, HindIII) and results in pCGN940. The majority of the napin coding region of pCGN940 was deleted by digestion with SalI and religation to form pCGN1800. Single-stranded DNA from pCGN1800 was used in an in vitro mutagenesis reaction (Adelman et al., *DNA* (1983) 2:183-193) using the synthetic oligonucleotide 5' GCTTGTTCGCCATGGATATCTTCTG-TATGTTC 3', SEQ ID NO: 42. This oligonucleotide inserted an EcoRV and an NcoI restriction site at the junction of the promoter region and the ATG start codon of the napin gene. An appropriate mutant was identified by hybridization to the oligonucleotide used for the mutagenesis and sequence analysis and named pCGN1801.

A 1.7 kb promoter fragment was subcloned from pCGN1801 by partial digestion with EcoRV and ligation to pCGN786 (a pCGN566 chloramphenicol based vector with the synthetic linker described above in place of the normal polylinker) cut with EcoRI and blunted by filling in with DNA Polymerase I Klenow fragment to create pCGN1802.

A 2.1 kb SalI fragment of napin 1-2 (FIG. 10 and SEQ ID NO: 29) containing 3' downstream sequences is subcloned into pCGN789 (described above) and results in pCGN941. pCGN941 is digested with XhoI and HindIII and the resulting approximately 1.6 kb of napin 3' sequences are inserted into XhoI-HindIII digested pCGN1802 to result in pCGN1803. In order to remove a 326 nucleotide HindIII fragment inserted opposite to its natural orientation, as a result of the fact that there are 2 HindIII sites in pCGN1803, the pCGN1803 is digested with HindIII and religated. Following religation, a clone is selected which now contains only 1.25 kb of the original 1.6 napin 3' sequence. This clone, pCGN1808 is the napin 1-2 expression cassette and contains 1.725 kb of napin promoter sequences and 1.265 kb of napin 3' sequence with the unique cloning sites SalI, BglII, PstI and XhoI in between.

Napin 1-2 pCGN3223 Expression Cassette

Alternatively, pCGN1808 may be modified to contain flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) Gene 32:48 1-485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN 1808 construct. The forward primer contains ClaI, HindIII, NotI, and KpnI restriction sites as well as nucleotides 408-423 of the napin 5'-sequence (from the EcoRV site) and the reverse primer contains the complement to napin sequences 718-739 which include the unique SacI site in the 5'-promoter. The PCR was performed using a Perkin Elmer/Cetus thermocycler according to manufacturer's specifications. The PCR fragment is subcloned as a blunt-ended fragment into pUC8 (Vieira and Messing (1982) Gene 19:259-268) and digested with HincII to give pCGN3217. Sequence of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

Desaturase sequences in sense or anti-sense orientation may be inserted into a napin expression cassette via the cloning sites. The resulting construct may be employed for plant transformation. For example, one of ordinary skill in the art could also use known techniques of gene cloning, mutations, insertion and repair to allow cloning of a napin expression cassette into any suitable binary vector, such as pCGN1557 (described in Example 7) or other similar vectors.

Desaturase Expression

The coding region of the safflower desaturase contained in pCGN3222 is cloned into the pCGN3223 napin cassette by digestion with XhoI and ligation to pCGN3223 digested with XhoI and SalI. The resulting plasmid, pCGN3229 is digested with Asp718 and inserted in the binary vector pCGN1578 (McBride and Summerfelt (1990) *Plant Mol. Biol.* 14:269-276) at the unique Asp718 site. The resulting binary vector is pCGN3231 and contains the safflower desaturase coding sequences flanked by the napin 5' and 3' regulatory sequences as well as the plant selectable marker construct, 35s/NPTII/tml.

The resulting binary vector, pCGN3231, is transformed into *Agrobacterium* and utilized for plant transformation as described in Example 10. For Northern analysis, total RNA is isolated from day 21 and day 28 post-anthesis developing seed from plants transformed with pCGN3231. Five samples were analyzed at day 21 and two at day 28 post-anthesis. RNA was isolated by the method of Hughes and Galau (*Plant Mol. Biol. Reporter* (1988) 6: 253-257). Northern blot analysis was performed using a labeled 0.8 kb BglII fragment of pCGN1894 as a probe. Prehybridization and hybridization was at 42° C. in 50% formamide, 10× Denhardt's solution, 5×SSC, 0.1% SDS, 5 mM EDTA and 100 ug/ml denatured salmon sperm DNA. Filters were washed at 55° C. in 0.1× SSC, 0.1% SDS. Under these conditions, the probe does not hybridize to the endogenous *Brassica* desaturase gene sequences. mRNA complementary to the safflower desaturase was detected in all the transgenic samples examined. More mRNA was present at day 28 than at day 21 post-anthesis and the highest level of RNA was seen in transgenic 3231-8. The total safflower desaturase mRNA level was estimated to be ~0.01% of the message at day 28 post-anthesis.

Western analysis (see below) gives a preliminary indication of increased protein in one transformant, 3231-8 in a *Brassica napus* cv. Delta plant. However, the Western analysis is complicated by two factors: 1. The presence of cross-reacting material at the same molecular weight as expected for the safflower desaturase. We believe this material is the endogenous *Brassica* desaturase. 2. The analysis of levels of protein expressed is also complicated by the normal developmental increase in the expression of desaturase protein during this time period. If the seeds examined are not at the precise developmental stage as the control seeds, quantitative differences in the amount of material seen may be simply due to the normal increase in the Brassica desaturase over this time period and not due to the expression of the safflower desaturase.

Western Analysis

Soluble protein is extracted from developing seeds of Brassica by homogenization with one volume (1 ml/gram fresh weight) of buffer containing 20 mM potassium phosphate, pH 6.8. The homogenate is clarified by centrifugation at 12,000×g for 10 minutes. A second centrifugation is performed if necessary to provide a non-particulate supernatant.

Protein concentration of the extract is measured by the micromethod of Bradford (*Anal. Biochem.* (1976) 72:248-254). Proteins (20-60 µg) are separated by denaturing electrophoresis by the method of Laemmli (supra), and are transferred to nitrocellulose membrane by the method of Tobin et al. (*Proc. Nat. Acad Sci.* (1979) 76:4350-4354).

The nitrocellulose membrane is blocked by incubation at room temperature for 15 minutes or at 4° C. overnight in Tris-buffered saline with Tween 20 (Polyoxyethylenesorbitan monolaurate) and "TTBS-milk", (TTBS=20 mM Tris-HCl, 500 mM NaCl, 0.1% Tween 20 (v/v), pH 7.5; "TTBS-milk"=TTBS and 3% skim milk powder). The volume of liquid in all incubations with the nitrocellulose membrane is sufficient to cover the membrane completely. The membrane is then incubated for an additional 5 minutes in TTBS.

The nitrocellulose membrane is incubated for at least one hour with shaking at room temperature with rabbit anti-stearoyl-ACP desaturase antiserum that was diluted 5,000- or 10,000-fold in "TTBS-milk". The rabbit anti-desaturase antiserum was commercially prepared from desaturase protein (purified as described in Example 1) by Berkeley Antibody Co. (Richmond, Calif.). The membrane is washed twice by shaking with TTBS for 5 minutes and then with deionized $H_2O$ for 30 seconds.

The nitrocellulose membrane is incubated for at least 45 minutes at room temperature in a solution of "TTBS-milk" in which anti-rabbit IgG-alkaline phosphatase conjugate (Promega, Madison, Wis.) is diluted 7,500-fold. The membrane is washed twice in TTBS followed by deionized $H_2O$, as described above.

The nitrocellulose membrane is equilibrated in buffer containing 100 mM Tris-HCl, 100 mM NaCl, 50 mM $MgCl_2$, pH 9.5, by shaking for 5 minutes. The color reaction is initiated by placing the nitrocellulose membrane into 50 ml of the same buffer to which has been added 15 mg p-nitroblue tetrazolium chloride and 7.5 mg 5-bromo-4 chloro-3-indolyl phosphate toluidine salt (BioRad Labs; Richmond, Calif.). The color reaction is stopped by rinsing the nitrocellulose membrane with deionized $H_2O$ and drying it between filter papers.

Fatty Acid Analysis

Analysis of developing seeds indicated no significant change in fatty acid (total seed lipid) composition of the transformed pCGN3231 Delta plants with respect to the control plants. This result is consistent with the low levels of safflower mRNA observed in transgenic plants as compared to levels of endogenous Brassica desaturase (Example 12).

However, subsequent fatty acid analysis of individual mature seeds of Delta plants containing the pCGN3231 construct showed an average of 0.97±0.16% stearate compared with an average of 1.47±0.24% obtained from seed testing of 2 different Delta control plants. Individual seeds show as little as 0.8% stearate and a saturate content (16:0+18:0) as low as 4.9%.

Example 10

In this example, an *Agrobacterium*-mediated plant transformation is described. *Brassica napus* is exemplified. The method is also useful for transformation of other *Brassica* species including *Brassica campestris*.

Plant Material and Transformation

Seeds of *Brassica napus* cv. Delta are soaked in 95% ethanol for 2 min, surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco) supplemented with pyrodoxine (50 µg/l), nicotinic acid (50 µg/l), glycine (200 µg/l), and 0.6% Phytagar (Gibco) pH 5.8. Seeds are germinated in a culture room at 22° C. in a 16 h photoperiod with cool fluorescent and red light of intensity approximately 65 µEinsteins per square meter per second ($\mu Em^{-2}S^{-1}$).

Hypocotyls are excised from 7 day old seedlings, cut into pieces approximately 4 mm in length, and plated on feeder plates (Horsch et al. 1985). Feeder plates are prepared one day before use by plating 1.0 ml of a tobacco suspension culture onto a petri plate (100×25 mm) containing about 30 ml MS salt base (Carolina Biological) 100 mg/l inositol, 1.3 mg/l thiamine-HCl, 200 mg $KH_2PO_4$ with 3% sucrose, 2,4-D (1.0 mg/l), 0.6% Phytagar, and pH adjusted to 5.8 prior to autoclaving (MS0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). All hypocotyl explants are preincubated on feeder plates for 24 h. at 22° C. in continuous light of intensity 30 $\mu Em^{-2}S^{-1}$ to 65 $\mu Em^{-2}S^{-1}$.

Single colonies of *A. tumefaciens* strain EHA101 containing a binary plasmid are transferred to 5 ml MG/L broth and grown overnight at 30° C. Per liter, MG/L broth contains 5 g mannitol, 1 g L-glutamic acid or 1.15 g sodium glutamate, 0.25 g $kH_2PO_4$, 0.10 g NaCl, 0.10 g $MgSO_4.7H_2O$, 1 mg biotin, 5 g tryptone, and 2.5 g yeast extract, and the broth is adjusted to pH 7.0. Hypocotyl explants are immersed in 7-12 ml mg/l broth with bacteria diluted to $1 \times 10^8$ bacteria/ml and after 10-20 min. are placed onto feeder plates. After 48 h of co-incubation with *Agrobacterium*, the hypocotyl explants are transferred to B5 0/1/0 callus induction medium which contains filter sterilized carbenicillin (500 mg/l, added after autoclaving) and kanamycin sulfate (Boehringer Mannheim) at concentrations of 25 mg/l.

After 3-7 days in culture at 65 $\mu Em^{-2}S^{-1}$ to 75 $\mu Em^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% Phytagar) and placed in a culture room with conditions as described for seed germination. After 2-4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for NPT II activity.

Example 11

In this example, a DNA-bombardment plant transformation is described. Peanut transformation is exemplified.

DNA sequences of interest may be introduced as expression cassettes, comprising at least a promoter region, a gene of interest, and a termination region, into a plant genome via particle bombardment as described in European Patent Application 332 855 and in co-pending application U.S. Ser. No. 07/225,332, filed Jul. 27, 1988.

Briefly, tungsten or gold particles of a size ranging from 0.5 µM-3 µM are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers.

The bombardment of the tissue with the DNA-coated particles is carried out using a Biolistics™ particle gun (Dupont; Wilmington, Del.). The particles are placed in the barrel at variable distances ranging from 1 cm-14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 µM to 30 µM.

Following bombardment, plants may be regenerated following the method of Atreya, et al., (*Plant Science Letters* (1984) 34:379-383). Briefly, embryo axis tissue or cotyledon segments are placed on MS medium (Murashige and Skoog, *Physio. Plant.* (1962) 15:473) (MS plus 2.0 mg/l 6-benzyladenine (BA) for the cotyledon segments) and incubated in the dark for 1 week at 25±2° C. and are subsequently transferred to continuous cool white fluorescent light (6.8 W/m$^2$). On the 10th day of culture, the plantlets are transferred to pots containing sterile soil, are kept in the shade for 3-5 days are and finally moved to greenhouse.

The putative transgenic shoots are rooted. Integration of exogenous DNA into the plant genome may be confirmed by various methods known to those skilled in the art.

Example 12

This example describes methods to obtain desaturase cDNA clones from other plant species using the DNA from the *C. tinctorius* Δ-9 desaturase clone as the probe.

Isolation of RNA for Northern Analysis

Poly(A)+ RNA is isolated from *C. tinctorius* embryos collected at 14-17 days post-anthesis and *Simmondsia chinensis* embryos as described in Example 5.

Total RNA is isolated from days 17-18 days post-anthesis *Brassica campestris* embryos by an RNA minipreparation technique (Scherer and Knauf, *Plant Mol. Biol.* (1987) 9:127-134). Total RNA is isolated from *R. communis* immature endosperm of about 14-21 days post-anthesis by a method described by Halling, et al. (*Nucl. Acids Res.* (1985) 13:8019-8033). Total RNA is isolated from 10 g each of young leaves from *B. campestris, B. napus*, and *C. tinctorius*, by extraction of each sample in 5 ml/g tissue of 4 M guanidine thiocyanate buffer as described by Colbert et al. (*Proc. Nat. Acad. Sci.* (1983) 80:2248-2252). Total RNA is also isolated from immature embryos of *Cuphea hookeriana* by extraction as above in 10 ml/g tissue.

Total RNA is isolated from immature embryos of California bay (*Umbellularia californica*) by an adaptation of the method of Lagrimini et al. (*Proc. Nat. Acad. Sci.* (1987) 84:7542-7546). Following homogenization in grinding buffer (2.5 ml/g tissue) as described, RNA is precipitated from the aqueous phase by addition of 1/10 volume 3 M sodium acetate and 2 volumes ethanol, followed by freezing at −80° C. for 30 minutes and centrifugation at 13,000×g for 20 minutes. The pellets are washed with 80% ethanol and centrifugation is repeated as above. The pellets are resuspended in water, two volumes of 4 M LiCl are added, and the samples are placed at −20° C. overnight. Samples are centrifuged as above and the pellets washed with 80% ethanol. Ethanol precipitation is repeated as above.

Total RNA is further purified from *B. campestris, B. napus,* and *C. tinctorius* leaves, and from *C. tinctorius, B. campestris*, California bay, and jojoba, and from *R. communis* immature endosperm, by removing polysaccharides on a 0.25 g Sigma Cell 50 cellulose column. The RNA is loaded onto the column in 1 ml of loading buffer (20 mM Tris-HCl pH 7.5, 0.5M NaCl, 1 mM EDTA, 0.1% SDS), eluted with loading buffer, and collected in 500 μl fractions. Ethanol is added to the samples to precipitate the RNA. The samples are centrifuged, and the pellets resuspended in sterile distilled water, pooled, and again precipitated in ethanol. The sample is centrifuged, and the resulting RNA is subjected to oligo(dT)-cellulose chromatography to enrich for poly(A)+ RNA as described by Maniatis et al. (*Molecular Cloning: A Laboratory Manual*, Cold Spring Harbor Laboratory, New York (1982)). Poly(A)+ RNA is also purified from total *Cuphea hookeriana* RNA by oligo(dT)-cellulose chromatography.

Northern Analysis Using *C. tinctorius* Desaturase Clone: 2.5 μg of poly(A)+ RNA from each of the above described poly(A)+ samples from immature embryos of jojoba, *Cuphea hookeriana*, California bay, *Brassica campestris*, and *C. tinctorius*, from immature endosperm of *R. communis*, and from leaves of *C. tinctorius, B. campestris*, and *B. napus* are electrophoresed on formaldehyde/agarose gels (Fourney et al., *Focus* (1988) 10:5-7) and transferred to a Hybond-C extra (Amersham, Arlington Heights, Ill.) filter according to manufacturer's specifications. The filter is prehybridized for four hours and hybridized overnight at 42° C. in a roller bottle containing 10 ml of hybridization buffer (1 M NaCl, 1% SDS, 50% formamide, 0.1 mg/ml denatured salmon sperm DNA) in a Hybridization Incubator, model 1040-00-1 (Robbins Scientific Corporation, Sunnyvale, Calif.). The probe used in the hybridization is a gel-isolated BglII fragment of the Δ-9 desaturase clone that is labeled with $^{32}$P-dCTP using a BRL (Gaithersburg, Md.) nick-translation kit, following manufacturer's instructions. The blot is washed three times for 20 minutes each in 2×SSC, 0.5% SDS at 55° C. The blot is exposed at −80° C., with a Dupont Cronex intensifying screen, to X-ray film for four days.

The autoradiograph shows that the *C. tinctorius* desaturase gene is expressed in both immature embryos and leaves of *C. tinctorius*, although the level of expression is considerably higher in embryos than in leaves. The autoradiograph also shows hybridization of the *C. tinctorius* desaturase clone to mRNA bands of a similar size in immature embryos from jojoba and California bay, and immature endosperm from *R. communis*. Hybridization is also detectable in RNA from *B. campestris* embryos upon longer exposure of the filter to X-ray film.

*R. communis* cDNA Library Construction: A plant seed cDNA library may be constructed from poly(A)+ RNA isolated from *R. communis* immature endosperm as described above. The plasmid cloning vector pCGN1703, and cloning method are as described in Example 5. The *R. communis* endosperm cDNA bank contains approximately 2×10$^6$ clones with an average cDNA insert size of approximately 1000 base pairs.

The *R. communis* immature endosperm cDNA bank is moved into the cloning vector lambda gt22 (Stratagene Cloning Systems) by digestion of total cDNA with NotI and ligation to lambda gt22 DNA digested with NotI. The resulting phage are packaged using a commercially available kit and titered using *E. coli* strain LE392 (Stratagene Cloning Systems, La Jolla, Calif.). The titer of the resulting library was approximately 1.5×10$^7$ pfu/ml.

*R. communis* cDNA Library Screen: The library is plated on *E. coli* strain LE392 at a density of approximately 25,000 pfu/150 mm NZY plate to provide approximately 50,000 plaques for screening. Phage are lifted in duplicate on to NEN (Boston, Mass.) Colony/Plaque Screen filters as described in Example 5. Following prehybridization at 42° C. in 25 ml of hybridization buffer (1 M NaCl, 1% SDS, 50% formamide, 0.1 mg/ml denatured salmon sperm DNA) filters are hybridized overnight with a gel-purified 520 base pair BglII fragment of the *C. tinctorius* desaturase clone (FIG. 7A) that is radiolabeled with $^{32}$p-dCTP using a BRL (Gaithersburg, Md.) Nick Translation System. Filters are washed three times for 20 minutes each in 2×SSC, 0.5% SDS at 55° C. in a shaking water bath. Filters are exposed to X-ray film overnight at −80° C with a Dupont Cronex intensifying screen.

Clones are detected by hybridization on duplicate filters with the *C. tinctorius* desaturase cDNA fragment and plaque purified. During plaque purification, it was observed that larger plaques were obtained when *E. coli* strain Y1090

(Young, R. A. and Davis, R. W., *Proc. Natl. Acad. Sci. USA* (1983) 80:1194) was used as the host strain. This strain was thus used in subsequent plaque purification steps. Phage DNA is prepared from the purified clones as described by Grossberger (*NAR* (1987) 15:6737) with the following modification. The proteinase K treatment is replaced by the addition of 10% SDS and a 10 minute incubation at room temperature. Recovered phage DNA is digested with EcoRI, religated at low concentration, and transformed into *E. coli* DH5α(BRL; Gaithersburg, Md.) cells to recover plasmids containing cDNA inserts in pCGN1703. Minipreparation DNA (Maniatis et al., supra) is prepared from the clones and DNA sequence is determined as described above. Partial nucleotide sequence of the cDNA insert of a *R. communis* desaturase clone pCGN3230 is presented in FIG. 3A and SEQ ID NO: 14. The complete nucleotide sequence of this clone is presented in FIG. 3B and as SEQ ID NO: 15.

Northern Analysis Using *R. communis* Desaturase Clone: Total RNA for Northern analysis is isolated from tobacco leaves by the method of Ursin et al. (*Plant Cell* (1989) 1:727-736), petunia and tomato leaves by the method of Ecker and Davis (*Proc. Nat. Acad. Sci.* (1987) 84:5202-5206), and corn leaves by the method of Turpen and Griffith (*Biotechniques* (1986) 4:11-15). Total RNA samples from tobacco, corn, and tomato leaves are enriched for poly(A)+ RNA by oligo(dT)-cellulose chromatography as described by Maniatis et al. (supra).

Poly(A)+ RNA samples from tomato leaves (4 µg) and corn and tobacco leaves (1 µg each), and total RNA from petunia leaves (25 µg) are electrophoresed on a formaldehyde/agarose gel as described by Shewmaker et al. (*Virology* (1985) 140:281-288). Also electrophoresed on this gel are poly(A)+ RNA samples isolated from *B. campestris* day 17-19 embryos and *B. campestris* leaves (2 µg each), immature embryos from *C. tinctorius*, bay, and jojoba (1 µg each), and *R. communis* endosperm (1 µg). The isolation of these poly(A)+ RNA samples is described above for the Northern analysis using *C. tinctorius* desaturase cDNA as probe. The RNA is transferred to a nitrocellulose filter as described by Shewmaker et al. (supra) and prehybridized and hybridized at 42° C. in 50% formamide, 10× Denhardt's solution (described in Maniatis et al. (supra)), 5×SSC, 0.1% SDS, 5 mM EDTA, 100 ug/ml denatured salmon sperm DNA,. and 10% dextran sulfate (in hybridization buffer only). The probe for hybridization is the $^{32}$P-labeled (BRL Nick Translation Kit) 1.7 kb SalI insert of pCGN3230 that has been gel-purified from minipreparation DNA. The filter is washed following hybridization for 30 minutes in 2×SSC, 0.1% SDS at 42° C. and at 50° C. twice for 15 minutes each. The filter is exposed to X-ray film overnight at −80° C. with a Dupont Cronex intensifying screen.

The autoradiograph shows hybridization of the *R. communis* desaturase clone to mRNA bands of a similar size in immature embryos from *B. campestris*, California bay, and *C. tinctorius*, and also in corn leaves and *R. communis* endosperm.

*B. campestris* Embryo cDNA Library Construction: Total RNA is isolated from 5 g of *B. campestris* cv. R500 embryos obtained from seeds harvested at days 17-19 post-anthesis. RNA is extracted in 25 mls of 4 M guanidine thiocyanate buffer as described by Colbert et al. (*PNAS* (1983) 80:2248-2252). Polysaccharides are removed from the RNA sample by resuspending the pellet in 6 ml of 1× TE (10 mM Tris/1 mM EDTA pH 8), adding potassium acetate to a concentration of 0.05M, and adding one half volume of ethanol. The sample is placed on ice for 60 minutes and centrifuged for 10 minutes at 3000×g. RNA is precipitated from the supernatant by adding sodium acetate to a concentration of 0.3 M followed by the addition of two volumes of ethanol. RNA is recovered from the sample by centrifugation at 12,000×g for 10 minutes and yield calculated by UV spectrophotometry. Two mg of the total RNA is further purified by removing polysaccharides on a 0.25 g Sigma Cell 50 cellulose column, as described above, and is also enriched for poly(A)+ RNA by oligo(dT)-cellulose chromatography as described above.

A *B. campestris* day 17-19 post anthesis embryo cDNA library is constructed in plasmid vector pCGN1703 as described in Example 5, using 5 ug of the above described poly(A)+ RNA. The library, which consists of approximately $1.5×10^5$ transformants, is amplified by plating and scraping colonies, and is stored as frozen *E. coli* cells in 10% DMSO at −80° C. DNA is isolated from a portion of the amplified library by scaling up the alkaline lysis technique of Birnboim and Doly (*Nucleic Acids Res.* (1979) 7:1513), and purified by CsCl centrifugation. Library DNA is digested with EcoRI and is cloned into EcoRI-digested bacteriophage lambda gt10 (Stratagene; La Jolla, Calif.) DNA. The DNA is packaged using Gigapack II Gold in vitro packaging extracts (Stratagene; La Jolla, Calif.) according to manufacturer's specifications. The titer of the phage stock, determined by dilution plating of phage in *E. coli* C600 hfl− cells (Huynh, et al., DNA Cloning. Volume 1. Eds. Gover, D. M. (1985) IRL Press Limited: Oxford, England, pp. 56, 110), is $6×10^6$ pfu per ml.

*B. campestris* cDNA Library Screen: The library is plated on *E. coli* strain C600 hfl− at a density of approximately 30,000 pfu/150 mm NZY plate to provide approximately 120,000 plaques for screening. Phage are lifted in duplicate on to NEN (Boston, Mass.) Colony/Plaque Screen filters as described in Example 5. Filters are prehybridized and hybridized with the $^{32}$P-labeled fragment of pCGN3230 as described above for the Northern hybridization. Filters are washed for 30 minutes in 2×SSC, 0.1% SDS at 50° C. and at 55° C. twice for 15 minutes each. Filters are exposed to X-ray film overnight at −80° C. with a Dupont Cronex intensifying screen.

Clones are detected by hybridization on duplicate filters to the *R. communis* desaturase cDNA fragment and plaque purified. During plaque purification, the probe used was a gel-purified 1.4 kb SstI fragment of pCGN3230 which lacks the poly(A)+ tail. As described above, phage DNA is isolated from purified lambda clones, digested with EcoRI, ligated, and transformed to *E. coli* DH5α cells. Minipreparation DNA is prepared and partial DNA sequence determined as described above. Partial DNA sequences of two clones, pCGN3235 and pCGN3236, are presented in FIG. 4A (SEQ ID NO: 17) and 4B (SEQ ID NO: 18), respectively. Initial DNA sequence analysis of the 3' regions of these clones indicates that pCGN3236 and pCGN3235 are cDNA clones from the same gene. pCGN3236 is a shorter clone than pCGN3235, which appears to contain the entire coding region of the *B. campestris* desaturase gene. The complete nucleotide sequence of pCGN3235 is presented in FIG. 4C and SEQ ID NO: 19.

Figure 7C:
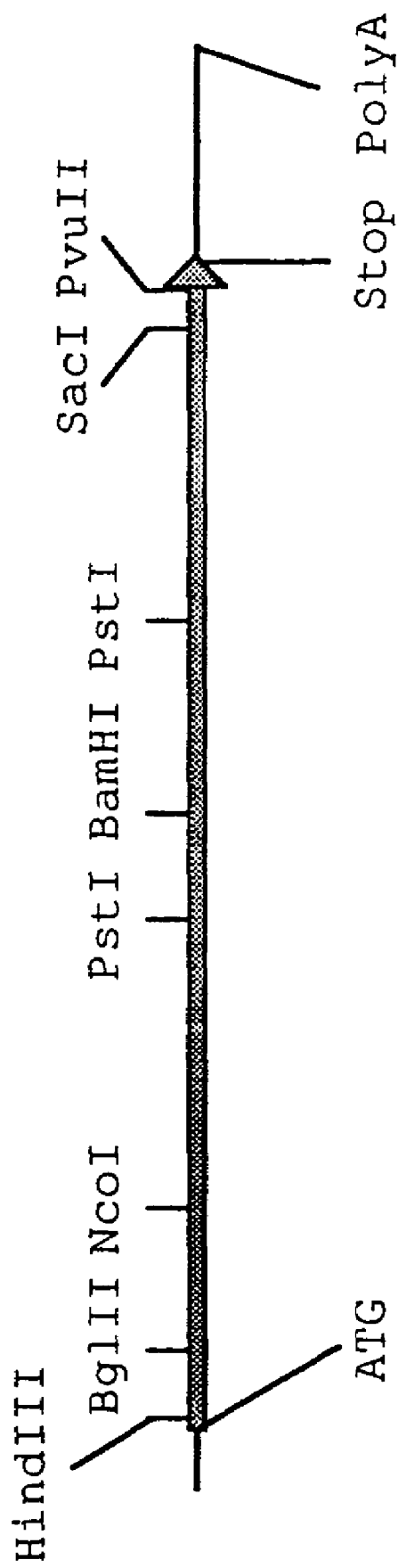
FIG. 7C represents a *B. campestris* clone.

Desaturase Gene Analysis: Southern and Northern analyses of *Brassica* species are conducted to determine the number of genes which encode the *Brassica* desaturase clone, pCGN3235 in *B. campestris*, *B. oleracea*, and *B. napus*, and the timing of expression of the gene in *B. campestris* developing seeds. DNA is isolated from leaves of each of the above-named *Brassica* species by the method of Bernatzky and Tanksley (*Theor. Appl. Genet.* (1986) 72:314-321). DNA from each of the species is digested with restriction endonucleases EcoRI and XbaI (10 ug/digest), electrophoresed in a 0.7% agarose gel, and transferred to a nitrocellulose filter (Maniatis et al., supra). The filter is prehybridized and hybridized at 42° C. (as described above for Northern analysis using *R. communis* desaturase clone) with a $^{32}$p-labeled (nick translation) gel-isolated HindIII/PvuII fragment of pCGN3235 (FIG. 7C). The filter is washed following overnight hybridization, for 30 minutes at 55° C. in 1×SSC, 0.1% SDS, followed by two 15 minute washed at 55° C. in 0.1×SSC, 0.1% SDS.

The autoradiograph indicates that the *Brassica* desaturase is encoded by a small gene family consisting of about two genes in *B. campestris* and *B. oleracea*, and about four genes in *B. napus*.

The timing of expression of the desaturase gene during seed development is determined by Northern analysis. RNA is isolated from immature seeds of *B. campestris* cv. R500 collected at 11, 13, 15, 17, 19, 21, 25, 30, 35, and 40 days post-anthesis. Total RNA is isolated as described by Scherer and Knauf (*Plant Mol. Biol.* (1987) 9:127-134). Twenty five micrograms of RNA from each time point are electrophoresed through a formaldehyde-containing 1.5% agarose gel as described by Shewmaker, et al. (supra) and blotted to nitrocellulose (Thomas, *Proc. Nat. Acad. Sci.* (1980) 77:5201-5205). The blot is pre-hybridized and hybridized at 42° C. with the $^{32}$P-labeled HindIII/PvuII fragment of pCGN3235 as described above. The filter is washed following overnight hybridization, for 30 minutes at 55° C. in 1×SSC, 0.1% SDS, followed by two 15 minute washed at 55° C. in 0.1×SSC, 0.1% SDS.

The autoradiograph indicates that the desaturase gene is expressed in *B. campestris* developing seeds beginning at about day 19 and through about day 30, with maximal expression at day 25. By a similar Northern analysis, the level of desaturase mRNA in developing *Brassica napus* seeds (day 21) was estimated to be approximately 1% of the total mRNA.

Isolation of Other Desaturase Gene Sequences: cDNA libraries may be constructed as described above and genomic libraries can be constructed from DNA from various sources using commercially available vectors and published DNA isolation, fractionation, and cloning procedures. For example, a *B. campestris* genomic library can be constructed using DNA isolated according to Scofield and Crouch (J. Biol. Chem. (1987) 262:12202-12208) that is digested with BamHI and fractionated on sucrose gradients (Maniatis et al., supra), and cloned into the lambda phage vector Lambda-Gem-11 (Promega; Madison, Wis.) using cloning procedures of Maniatis et al. (supra).

cDNA and genomic libraries can be screened for desaturase cDNA and genomic clones, respectively, using published hybridization techniques. Screening techniques are described above for screening libraries with DNA fragments. Libraries may also be screened with synthetic oligonucleotides, for example using methods described by Berent et al. (*BioTechniques* (1985) 3:208-220). Probes for the library screening can be prepared by PCR, or from the sequences of the desaturase clones provided herein. Oligonucleotides prepared from the desaturase sequences may be used, as well as longer DNA fragments, up to the entire desaturase clone.

For example, jojoba polyadenylated RNA is used to construct a cDNA library in the cloning vector λZAPII/EcoRI (Stratagene, San Diego, Calif.). RNA is isolated from jojoba embryos collected at 80-90 days post-anthesis by isolating polyribosomes using a method initially described by Jackson and Larkins (*Plant Physiol.* (1976) 57:5-10) and modified by Goldberg et al. (*Developmental Biol.* (1981) 83:201-217). Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

The library is constructed using protocols, DNA and bacterial strains as supplied by the manufacturer. Clones are packaged using Gigapack Gold packaging extracts (Stratagene), also according to manufacturer's recommendations. The cDNA library constructed in this manner contains approximately 1×10$^6$ clones with an average cDNA insert size of approximately 400 base pairs.

The jojoba library is plated on *E. coli* XL1-Blue (Stratagene) at a density of approximately 5000 pfu/150 mm plate to provide approximately 60,000 plaques for screening. Phage are lifted onto duplicate nylon membrane filters as described previously. Filters are prehybridized at 42° C. in a hybridization buffer containing 40% formamide, 10× Denhardt's solution, 5×SSC, 0.1% SDS, 50 mM EDTA, and 100 µg/ml denatured salmon sperm DNA. Hybridization is at 42° C. in the same buffer with added nick translated (BRL Nick Translation System) 520 bp BglII fragment of the *C. tinctorius* desaturase clone described previously. Filters are washed at 50° C. in 2×SSC and exposed to X-ray film overnight.

Desaturase clones are detected by hybridization on duplicate filters with the *C. tinctorius* cDNA fragment and plaque-purified. Positive clones are recovered as plasmids in *E. coli* following manufacturer's directions and materials for in vivo excision. Partial, preliminary DNA sequence of a clone, 3-1, is determined and the corresponding amino acid sequence is translated in three frames. In this manner, homology to the *C. tinctorius* desaturase cDNA clone is detected in one reading frame. The preliminary DNA sequence of this jojoba desaturase cDNA fragment is shown in FIG. 5 (SEQ ID NO: 43). Also shown is the corresponding translated amino acid sequence in the reading frame having *C. tinctorius* desaturase homology. The jojoba cDNA fragment is approximately 75% homologous at the DNA level and approximately 79% homologous at the amino acid level compared to sequence of the *C. tinctorius* desaturase in this region.

Example 13

Antisense constructs are described which allow for transcription of a reverse copy of the *B. campestris* desaturase cDNA clone in the 5' to 3' orientation of transcription. In a similar fashion, anti-sense constructs can be prepared to reduce desaturase levels in other plant hosts.

Preferential Expression of Antisense Constructs in Embryos

In order to reduce the transcription of a desaturase gene in embryos of *B. napus* or *B. campestris*, constructs may be prepared which allow for production of antisense copies of the desaturase cDNA preferentially in the embryos. Promoter sequences which are desirable to obtain this pattern of expression include, but are not limited to, the ACP, Bce4, and napin 1-2 expression cassettes described in Examples 7, 8, and 9, respectively. It also may be desirable to control the expression of reverse copies of the desaturase cDNA under two different promoters in the same transformed plant to provide for a broader timing of expression of the antisense desaturase DNA. For example, expression from the ACP promoter may begin and end earlier than expression from the napin promoter. Thus, expressing the reverse desaturase from both promoters may result in the production of the antisense strand of DNA over a longer period of embryo development.

An example of expression of an antisense desaturase gene preferentially in the embryos is provided below. Similar constructs containing the same or a different fragment of the desaturase gene and any of the promoters described above, as well as other promoter regions which may be useful, may also be prepared using gene cloning, insertion, mutation and repair techniques well known to those of ordinary skill in the art.

A. Antisense Desaturase Expression from the ACP Promoter

Construction of pCGN3239 is as follows:

pCGN3235 (Example 12) is digested with PvuII and HindIII and the HindIII sticky ends are filled in with Klenow in the presence of 200 μM dNTPs. The 1.2 kb PvuII/HindIII fragment containing the desaturase coding sequence is gel purified and ligated in the antisense orientation into EcoRV-digested pCGN1977 (ACP expression cassette; described in Example 7) to create pCGN3238. The 4.2 kb XbaI/Asp718 fragment of pCGN3238 containing the antisense desaturase in the ACP cassette is transferred into XbaI/Asp718-digested pCGN1557 (binary transformation vector; described in Example 7) to create pCGN3239.

B. Antisense Desaturase Expression from the Napin Promoter

Construction of pCGN3240 is as follows: pCGN3235 is digested with PvuII and HindIII, the sticky ends are blunted, and the resulting fragment is inserted in an anti-sense orientation into pCGN3223 which has been digested with SalI and blunted with Klenow enzyme. The resulting plasmid, pCGN3240 will express an anti-sense desaturase RNA from the napin promoter cassette.

C. Antisense Desaturase Expression from a Dual Promoter Cassette

Construction of pCGN3242 is as follows: An Asp718 fragment of pCGN3240 containing the napin 5' and 3' regions surrounding the desaturase sequences is inserted into the Asp718 site of pCGN3239 (a binary vector containing an ACP promoter, antisense desaturase construct) to create pCGN3242.

The pCGN3242 construct was deposited under the terms of the Budapest Treaty on Dec. 3, 1993, with the American Type Culture Collection (ATCC) in a DH5 alpha *E. coli* strain. The accession number for the deposit is 4125 (ATCC No. 69506). The pCGN3242 strain having this accession number will be irrevocably and without restriction or condition released to the public upon the issuance of a patent. The address for the ATCC is 10801 University Boulevard, Manassas, Va. 20110-2209 USA.

Constitutive Transcription

A. Binary Vector Construction

1. Construction of pCGP291.

The KpnI, BamHI, and XbaI sites of binary vector pCGN1559 (McBride and Summerfelt, *Pl. Mol. Biol.* (1990) 14: 269-276) are removed by Asp718/XbaI digestion followed by blunting the ends and recircularization to produce pCGP67. The 1.84 kb PstI/HindIII fragment of pCGN986 containing the 35S promoter-tml3' cassette is inserted into PstI/HindIII digested pCGP67 to produce pCGP291.

2. Construction of pCGN986.

The 35S promoter-tml3' expression cassette, pCGN986, contains a cauliflower mosaic virus 35S (CaMV35) promoter and a T-DNA tml 3'-region with multiple restriction sites between them. pCGN986 is derived from another cassette, pCGN206, containing a CaMV35S promoter and a different 3' region, the CaMV region VI 3'-end. The CaMV 35S promoter is cloned as an AluI fragment (bp 7144-7734) (Gardner et. al., *Nucl. Acids Res.* (1981) 9:2871-2888) into the HincII site of M13mp7 (Messing, et. al., *Nucl. Acids Res.* (1981) 9:309-321) to create C614. An EcoRI digest of C614 produced the EcoRI fragment from C614 containing the 35S promoter which is cloned into the EcoRI site of pUC8 (Vieira and Messing, *Gene* (1982) 19:259) to produce pCGN147.

pCGN148a containing a promoter region, selectable marker (KAN with 2 ATG's) and 3' region, is prepared by digesting pCGN528 with BglII and inserting the BamHI-BglII promoter fragment from pCGN147. This fragment is cloned into the BglII site of pCGN528 so that the BglII site is proximal to the kanamycin gene of pCGN528.

The shuttle vector used for this construct, pCGN528, is made as follows: pCGN525 is made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141-1156). pCGN526 was made by inserting the BamHI fragment 19 of pTiA6 (Thomashow et. al., *Cell* (1980) 19:729-739), modified with XhoI linkers inserted into the SmaI site, into the BamHI site of pCGN525. pCGN528 is obtained by deleting the small XhoI fragment from pCGN526 by digesting with XhoI and religating.

pCGN149a is made by cloning the BamHI-kanamycin gene fragment from pMB9KanXXI into the BamHI site of pCGN148a. pMB9KanXXI is a. pUC4K variant (Vieira and Messing, *Gene* (1982) 19:259-268) which has the XhoI site missing, but contains a functional kanamycin gene from Tn903 to allow for efficient selection in *Agrobacterium*.

pCGN149a is digested with HindIII and BamHI and ligated to pUC8 digested with HindIII and BamHI to produce pCGN169. This removes the Tn903 kanamycin marker. pCGN565 and pCGN169 are both digested with HindIII and PstI and ligated to form pCGN203, a plasmid containing the CaMV 35S promoter and part of the 5'-end of the Tn5 kanamycin gene (up to the PstI site, Jorgenson et. al., (1979), supra). A 3'-regulatory region is added to pCGN203 from pCGN204, an EcoRI fragment of CaMV (bp 408-6105) containing the region VI 3' cloned into pUC18 (Yanisch-Perron, et al., *Gene* (1985) 33:103-119) by digestion with HindIII and PstI and ligation. The resulting cassette, pCGN206, is the basis for the construction of pCGN986.

The pTiA6 T-DNA tml 3'-sequences are subcloned from the Bam19 T-DNA fragment (Thomashow et al., (1980) supra) as a BamHI-EcoRI fragment (nucleotides 9062 to 12,823, numbering as in Barker et al., *Plant Mol. Biol.* (1982) 2:335-350) and combined with the pACYC184 (Chang and Cohen (197S), supra) origin of replication as an EcoRI-HindIII fragment and a gentamycin resistance marker (from plasmid pLB41), obtained from D. Figurski) as a BamHI-HindIII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give pCGN971. The BamHI site of pCGN971 is changed to an EcoRI site using linkers. The resulting EcoRI-SacI fragment containing the tml 3' regulatory sequences is joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligation with SalI linkers. The final expression cassette pCGN986 contains the CaMV 35S promoter followed by two SalI sites, an XbaI site, BamHI, SmaI, KpnI and the tml 3' region (nucleotides 11207-9023 of the T-DNA).

B. Insertion of Desaturase Sequence

The 1.6 kb XbaI fragment from pCGN3235 containing the desaturase cDNA is inserted in the antisense orientation into the XbaI site of pCGP291 to produce pCGN3234.

Plant Transformation

The binary vectors containing the expression cassette and the desaturase gene are transformed into *Agrobacterium tumefaciens* strain EHA101 (Hood, et al., *J. Bacteriol.* (1986) 168:1291-1301) as per the method of Holsters, et al., *Mol. Gen. Genet.* (1978) 163:181-187. Transformed *B. napus* and/or *Brassica campestris* plants are obtained as described in Example 10.

Analysis of Transgenic Plants

A. Analysis of pCGN3242 Transformed *Brassica campestris* cv. Tobin Plants

Due to the self-incompatibility of *Brassica campestris* cv. Tobin, individual transgenic plants are pollinated using non-transformed Tobin pollen. Because of this, the T2 seeds of a transgenic plant containing the antisense desaturase at one locus would be expected to segregate in a 1:1 ratio of transformed to non-transformed seed. The fatty acid composition (total seed lipids) of ten individual seeds collected at 26 days post-anthesis from several pCGN3242-transformed plants and one non-transformed control was analyzed by gas chromatography according to the method of Browse, et al., *Anal. Biochem.* (1986) 152:141-145. One transformant, 3242-T-1, exhibits a fatty acid composition that differed distinctly from controls on preliminary analysis. The control Tobin seeds contained an average of 1.8% 18:0 (range 1.5% -2.0%) and 52.9% 18:1 (range 48.2% -57.1%). T2 seeds of 3242-T-1 segregated into two distinct classes. Five seeds contained levels of 18:0 ranging from 1.3% to 1.9% and levels of 18:1 ranging from 42.2% to 58.3%. The other five seeds contained from 22.9% to 26.3% 18:0 and from 19.9% to 26.1% 18:1.

Analysis of individual mature seeds containing pCGN3242 in T2 seed yielded seed having up to 45% stearate by weight. No changes in the level of palmitate, the precursor to stearate, are observed. Increased percentages of 18:3 and low, but increased levels of long chain (>18 carbon) saturated fatty acids are seen. Reductions in the average total oil content observed in these seed may account for noted decreases in germination rates.

B. Analysis of pCGN3242 Transformed *Brassica napus* cv. A112

A dramatic increase in stearate composition is observed in mature self-pollinated seeds of a transformed plant (3242-A-3), from 1.8% to 39.8%. Increased stearate is accompanied by a decreased percentage of 18:1 and an increased percentage of 18:3 and long chain saturated fatty acids. T2 seed from the 3242-A-3 plant yields a somewhat continuous range of percent stearate in individual seeds up to 45% stearate. Oil content of high stearate 3242-A112 seed is variable, some seeds having over 30% stearate also have an oil content comparable to control A112 seeds. Segregation and Southern analysis indicate that in 3242-A-3 three functional T-DNA inserts are seen. Independent segregation of multiple antisense genes displaying various levels of expression may account for the range of stearate levels observed.

C. Triacylglyceride Analysis of Mature *Brassica* Seeds (3242-Tobin1)

Mature T2 seeds of *Brassica campestris* cv. Tobin containing pCGN3242 are crushed and 250 .mu.g of C18:0 triglyceride in 250 µg of toluene is added as an internal standard. The seeds are extracted with 1 ml of a 3:2 hexane/isopropanol mixture, dried down, and resuspended in 100 µl to make uniform solvent concentrations in each sample. 20 µl of each sample is placed on a silica gel TLC plate (Baker-flex Silica Gel 1B2, 20×20 cm, 200 µm thick) and run to the top with 100 ml of a 60:40 hexane/diethyl ether/acetic acid solvent system 50 .mu.g of standards containing tri-, di-, and monoglycerides, as well as free fatty acid are run in adjacent lanes, and can be visualized by spraying these lanes with 10% phosphomolybdic acid in methanol. After heating the spray lanes in an oven, these spots are used as a reference to cut out the non-visualized spots in the sample lane. The plant pieces containing TAG are extracted with 3 ml of 3:2 hexane/isopropanol, dried down and analyzed for fatty acid content by the acidic methanolysis method of Browse et al. (supra). The analyses demonstrates a triglycerol fatty acid composition substantially unchanged, including stearate content, from that observed in analysis of total seed lipids.

D. Analysis of pCGN3234 Transformed Plants

Some abnormalities have been observed in some transgenic *Brassica napus* cv. Delta and Bingo and *Brassica campestris* cv. Tobin plants containing pCGN3234. Thus, preliminary results suggest that constitutively expressive antisense desaturase may interfere with plant growth. These effects could be due to the constitutive expression of antisense desaturase RNA from the 35S promoter (i.e., perhaps providing undesirable leaf lipid compositions) or could be due to the transformation/tissue culture regime the plants have been subjected to, as examples.

The above results demonstrate the ability to obtain plant Δ-9 desaturases, isolate DNA sequences which encode desaturase activity and manipulate them. In this way, the production of transcription cassettes, including expression cassettes can be produced which allow for production, including specially differentiated cell production of the desired product. A purified *C. tinctorius* desaturase is provided and used to obtain nucleic acid sequences of *C. tinctorius* desaturase. Other plant desaturase sequences are provided such as *R. communis, B. campestris*, and *S. chinensis*. These sequences as well as desaturase sequences obtained from them may be used to obtain additional desaturase, and so on. And, as described in the application modification of oil composition may be achieved.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A plant seed oil of a rapeseed plant having endogenous saturated fatty acids comprising from 22.9% to 26.3% stearate.

2. The plant seed oil of claim 1, wherein the plant seed oil has endogenous unsaturated fatty acids comprising from 19.9% to 26.1% oleate.

3. The plant seed oil of claim 1, wherein the rapeseed plant comprises a recombinant DNA construct integrated into the genome of said plant comprising a napin promoter linked to the nucleic acid sequence of SEQ ID NO: 19 in antisense orientation.

4. The plant seed oil of claim 3, wherein the recombinant DNA construct comprises pCGN3242 deposited under ATCC Accession No. 69506.

* * * * *

UNITED STATES PATENT AND TRADEMARK OFFICE
CERTIFICATE OF CORRECTION

PATENT NO. : 7,572,926 B2  Page 1 of 1
APPLICATION NO. : 11/415867
DATED : August 11, 2009
INVENTOR(S) : Thompson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 391 days.

Signed and Sealed this

Seventh Day of September, 2010

David J. Kappos
*Director of the United States Patent and Trademark Office*

SEQUENCE LISTING

<160> NUMBER OF SEQ ID NOS: 45

<210> SEQ ID NO 1
<211> LENGTH: 63
<212> TYPE: PRT
<213> ORGANISM: Carthamus tinctorius
<220> FEATURE:
<221> NAME/KEY: MOD_RES
<222> LOCATION: (31)..(54)
<223> OTHER INFORMATION: Xaa = can be any naturally occurring amino acid

<400> SEQUENCE: 1

Ala Ser Thr Leu Gly Ser Ser Thr Pro Lys Val Asp Asn Ala Lys Lys
1               5                   10                  15

Pro Phe Gln Pro Pro Arg Glu Val His Val Gln Val Thr His Xaa Met
            20                  25                  30

Pro Pro Gln Lys Ile Glu Ile Phe Lys Ser Ile Glu Gly Xaa Ala Glu
        35                  40                  45

Gln Asn Ile Leu Val Xaa Leu Lys Pro Val Glu Lys Cys Trp Gln
    50                  55                  60

<210> SEQ ID NO 2
<211> LENGTH: 56
<212> TYPE: PRT
<213> ORGANISM: Carthamus tinctorius
<220> FEATURE:
<221> NAME/KEY: MOD_RES
<222> LOCATION: (8)
<223> OTHER INFORMATION: Xaa = can be any naturally occurring amino acid

<400> SEQUENCE: 2

Asp Phe Leu Pro Asp Pro Ala Xaa Glu Gly Phe Asp Glu Gln Val Lys
1               5                   10                  15

Glu Leu Arg Ala Arg Ala Lys Glu Ile Pro Asp Asp Tyr Phe Val Val
            20                  25                  30

Leu Val Gly Asp Met Ile Thr Glu Glu Ala Leu Pro Thr Tyr Gln Thr
        35                  40                  45

Met Leu Asn Thr Leu Asp Gly Val
    50                  55

<210> SEQ ID NO 3
<211> LENGTH: 14
<212> TYPE: PRT
<213> ORGANISM: Carthamus tinctorius

<400> SEQUENCE: 3

Asp Glu Thr Gly Ala Ser Leu Thr Pro Trp Ala Val Trp Thr
1               5                   10

<210> SEQ ID NO 4
<211> LENGTH: 13
<212> TYPE: PRT
<213> ORGANISM: Carthamus tinctorius

<400> SEQUENCE: 4

Asp Leu Leu His Thr Tyr Leu Tyr Leu Ser Gly Arg Val
1               5                   10

<210> SEQ ID NO 5
<211> LENGTH: 13
<212> TYPE: PRT
<213> ORGANISM: Carthamus tinctorius

<400> SEQUENCE: 5

Asp Met Arg Gln Ile Gln Lys Thr Ile Gln Tyr Leu Ile
1               5                   10

<210> SEQ ID NO 6
<211> LENGTH: 17
<212> TYPE: PRT
<213> ORGANISM: Carthamus tinctorius

```
<400> SEQUENCE: 6

Thr Glu Asn Ser Pro Tyr Leu Gly Phe Ile Tyr Thr Ser Phe Gln Glu
  1               5                  10                  15

Arg

<210> SEQ ID NO 7
<211> LENGTH: 57
<212> TYPE: PRT
<213> ORGANISM: Carthamus tinctorius
<220> FEATURE:
<221> NAME/KEY: MOD_RES
<222> LOCATION: (3)..(50)
<223> OTHER INFORMATION: Xaa = can be any naturally occurring amino acid

<400> SEQUENCE: 7

Asp Val Xaa Leu Ala Gln Ile Xaa Gly Thr Ile Ala Ser Asp Glu Lys
  1               5                  10                  15

Arg His Glu Thr Ala Tyr Thr Lys Ile Val Glu Lys Leu Phe Glu Ile
             20                  25                  30

Asp Pro Asp Gly Thr Val Leu Ala Phe Ala Asp Met Met Arg Lys Lys
         35                  40                  45

Ile Xaa Met Pro Ala His Leu Met Tyr
     50                  55

<210> SEQ ID NO 8
<211> LENGTH: 4
<212> TYPE: PRT
<213> ORGANISM: Carthamus tinctorius

<400> SEQUENCE: 8

Asp Asn Leu Phe
  1

<210> SEQ ID NO 9
<211> LENGTH: 16
<212> TYPE: PRT
<213> ORGANISM: Carthamus tinctorius
<220> FEATURE:
<221> NAME/KEY: MOD_RES
<222> LOCATION: (1)..(11)
<223> OTHER INFORMATION: Xaa = can be any naturally occurring amino acid

<400> SEQUENCE: 9

Xaa Xaa Phe Xaa Ala Val Xaa Gln Arg Leu Xaa Val Tyr Thr Ala Lys
  1               5                  10                  15

<210> SEQ ID NO 10
<211> LENGTH: 14
<212> TYPE: PRT
<213> ORGANISM: Carthamus tinctorius

<400> SEQUENCE: 10

Asp Tyr Ala Asp Ile Leu Glu Phe Leu Val Gly Arg Trp Lys
  1               5                  10

<210> SEQ ID NO 11
<211> LENGTH: 54
<212> TYPE: PRT
<213> ORGANISM: Carthamus tinctorius
<220> FEATURE:
<221> NAME/KEY: MOD_RES
<222> LOCATION: (15)
<223> OTHER INFORMATION: Xaa = can be any naturally occurring amino acid
```

-continued

```
<400> SEQUENCE: 11

Val Ala Asp Leu Thr Gly Leu Ser Gly Glu Gly Arg Lys Ala Xaa Asp
 1               5                  10                  15

Tyr Val Cys Gly Leu Pro Pro Arg Ile Arg Arg Leu Glu Glu Arg Ala
                20                  25                  30

Gln Gly Arg Ala Lys Glu Gly Pro Val Val Pro Phe Ser Trp Ile Phe
            35                  40                  45

Asp Arg Gln Val Lys Leu
        50

<210> SEQ ID NO 12
<211> LENGTH: 1533
<212> TYPE: DNA
<213> ORGANISM: Carthamus tinctorius

<400> SEQUENCE: 12
gctcacttgt gtggtggagg agaaaaacag aactcacaaa aagctttgcg actgccaaga      60
acaacaacaa caacaagatc aagaagaaga agaagaagat caaaaatggc tcttcgaatc    120
actccagtga ccttgcaatc ggagagatat cgttcgtttt cgtttcctaa gaaggctaat    180
ctcagatctc ccaaattcgc catggcctcc accctcggat catccacacc gaaggttgac    240
aatgccaaga agccttttca acctccacga gaggttcatg ttcaggtgac gcactccatg    300
ccaccacaga agatagagat tttcaaatcc atcgagggtt gggctgagca gaacatattg    360
gttcacctaa agccagtgga gaatgttgg caagcacagg atttcttgcc ggaccctgca    420
tctgaaggat tgatgaaca gtcaaggaa ctaagggcaa gagcaaagga gattcctgat    480
gattactttg ttgttttggt tggagatatg attacagagg aagccctacc tacttaccaa    540
acaatgctta ataccctaga tggtgtacgt gatgagactg gggctagcct tacgccttgg    600
gctgtctgga ctagggcttg gacagctgaa gagaacaggc atggcgatct tctccacacc    660
tatctctacc tttctgggcg ggtagacatg aggcagatac agaagacaat tcagtatctc    720
attgggtcag gaatggatcc tcgtaccgaa acagcccct accttgggtt catctacaca    780
tcgtttcaag agcgtgccac atttgtttct cacggaaaca ccgccaggca tgcaaaggat    840
catggggacg tgaaactggc gcaaatttgt ggtacaatcg cgtctgacga aaagcgtcac    900
gagaccgctt atacaaagat agtcgaaaag ctattcgaga tcgatcctga tggcaccgtt    960
cttgcttttg ccgacatgat gaggaaaaag atctcgatgc ccgcacactt gatgtacgat   1020
gggcgtgatg acaacctctt cgaacatttc tcggcggttg cccaaagact cggcgtctac   1080
accgccaaag actacgccga catactggaa tttctggtcg gcggtggaa agtggcggat   1140
ttgaccggcc tatctggtga agggcgtaaa gcgcaagatt atgttttgcgg ttgccacca   1200
agaatcagaa ggctggagga gagagctcaa gggcgagcaa aggaaggacc tgttgttcca   1260
ttcagctgga ttttcgatag acaggtgaag ctgtgaagaa aaaaaaacg agcagtgagt   1320
tcggtttctg ttggcttatt gggtagaggt taaaacctat tttagatgtc tgtttcgtgt   1380
aatgtggttt tttttcttct aatcttgaat ctggtattgt gtcgttgagt tcgcgtgtgt   1440
gtaaacttgt gtggctgtgg acatattata gaactcgtta tgccaatttt gatgacggtg   1500
gttatcgtct cccctggtgt tttttattg ttt                                 1533

<210> SEQ ID NO 13
<211> LENGTH: 396
<212> TYPE: PRT
<213> ORGANISM: Carthamus tinctorius
```

<400> SEQUENCE: 13

```
Met Ala Leu Arg Ile Thr Pro Val Thr Leu Gln Ser Glu Arg Tyr Arg
  1               5                  10                  15

Ser Phe Ser Phe Pro Lys Lys Ala Asn Leu Arg Ser Pro Lys Phe Ala
             20                  25                  30

Met Ala Ser Thr Leu Gly Ser Ser Thr Pro Lys Val Asp Asn Ala Lys
         35                  40                  45

Lys Pro Phe Gln Pro Pro Arg Glu Val His Val Gln Val Thr His Ser
     50                  55                  60

Met Pro Pro Gln Lys Ile Glu Ile Phe Lys Ser Ile Glu Gly Trp Ala
 65                  70                  75                  80

Glu Gln Asn Ile Leu Val His Leu Lys Pro Val Glu Lys Cys Trp Gln
                 85                  90                  95

Ala Gln Asp Phe Leu Pro Asp Pro Ala Ser Glu Gly Phe Asp Glu Gln
            100                 105                 110

Val Lys Glu Leu Arg Ala Arg Ala Lys Glu Ile Pro Asp Asp Tyr Phe
        115                 120                 125

Val Val Leu Val Gly Asp Met Ile Thr Glu Glu Ala Leu Pro Thr Tyr
    130                 135                 140

Gln Thr Met Leu Asn Thr Leu Asp Gly Val Arg Asp Glu Thr Gly Ala
145                 150                 155                 160

Ser Leu Thr Pro Trp Ala Val Trp Thr Arg Ala Trp Thr Ala Glu Glu
                165                 170                 175

Asn Arg His Gly Asp Leu Leu His Thr Tyr Leu Tyr Leu Ser Gly Arg
            180                 185                 190

Val Asp Met Arg Gln Ile Gln Lys Thr Ile Gln Tyr Leu Ile Gly Ser
        195                 200                 205

Gly Met Asp Pro Arg Thr Glu Asn Ser Pro Tyr Leu Gly Phe Ile Tyr
    210                 215                 220

Thr Ser Phe Gln Glu Arg Ala Thr Phe Val Ser His Gly Asn Thr Ala
225                 230                 235                 240

Arg His Ala Lys Asp His Gly Asp Val Lys Leu Ala Gln Ile Cys Gly
                245                 250                 255

Thr Ile Ala Ser Asp Glu Lys Arg His Glu Thr Ala Tyr Thr Lys Ile
            260                 265                 270

Val Glu Lys Leu Phe Glu Ile Asp Pro Asp Gly Thr Val Leu Ala Phe
        275                 280                 285

Ala Asp Met Met Arg Lys Lys Ile Ser Met Pro Ala His Leu Met Tyr
    290                 295                 300

Asp Gly Arg Asp Asp Asn Leu Phe Glu His Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Ala Asp Leu Thr Gly Leu Ser Gly Glu
            340                 345                 350

Gly Arg Lys Ala Gln Asp Tyr Val Cys Gly Leu Pro Pro Arg Ile Arg
        355                 360                 365

Arg Leu Glu Glu Arg Ala Gln Gly Arg Ala Lys Glu Gly Pro Val Val
    370                 375                 380

Pro Phe Ser Trp Ile Phe Asp Arg Gln Val Lys Leu
385                 390                 395
```

-continued

<210> SEQ ID NO 14
<211> LENGTH: 225
<212> TYPE: DNA
<213> ORGANISM: Ricinus communis

<400> SEQUENCE: 14
aaaagaaaaa ggtaagaaaa aaaacaatgg ctctcaagct caatcctttc ctttctcaaa 60
cccaaaagtt accttctttc gctcttccac caatggccag taccagatct cctaagttct 120
acatggcctc taccctcaag tctggttcta aggaagttga gaatctcaag aagcctttca 180
tgcctcctcg ggaggtacat gttcaggtta cccattctat tgcca 225

<210> SEQ ID NO 15
<211> LENGTH: 1668
<212> TYPE: DNA
<213> ORGANISM: Ricinus communis

<400> SEQUENCE: 15
aaaagaaaaa ggtaagaaaa aaaacaatgg ctctcaagct caatcctttc ctttctcaaa 60
cccaaaagtt accttctttc gctcttccac caatggccag taccagatct cctaagttct 120
acatggcctc taccctcaag tctggttcta aggaagttga gaatctcaag aagcctttca 180
tgcctcctcg ggaggtacat gttcaggtta cccattctat gccaccccaa aagattgaga 240
tctttaaatc cctagacaat tggctgagg agaacattct ggttcatctg aagccagttg 300
agaaatgttg gcaaccgcag gattttttgc cagatcccgc ctctgatgga tttgatgagc 360
aagtcaggga actcagggag agagcaaagg agattcctga tgattatttt gttgttttgg 420
ttggagacat gataacggaa gaagcccttc ccacttatca aacaatgctg aataccttgg 480
atggagttcg ggatgaaaca ggtgcaagtc ctacttcttg ggcaatttgg acaagggcat 540
ggactgcgga agagaataga catggtgacc tcctcaataa gtatctctac ctatctggac 600
gagtggacat gaggcaaatt gagaagacaa ttcaatattt gattggttca ggaatggatc 660
cacggacaga aaacagtcca taccttgggt tcatctatac atcattccag gaaagggcaa 720
ccttcatttc tcatgggaac actgcccgac aagccaaaga gcatggagac ataaagttgg 780
ctcaaatatg tggtacaatt gctgcagatg agaagcgcca tgagacagcc tacacaaaga 840
tagtggaaaa actctttgag attgatcctg atggaactgt tttggctttt gctgatatga 900
tgagaaagaa aatttctatg cctgcacact tgatgtatga tggccgagat gataatcttt 960
ttgaccactt ttcagctgtt gcgcagcgtc ttggagtcta cacagcaaag gattatgcag 1020
atatattgga gttcttggtg ggcagatgga aggtggataa actaacgggc ctttcagctg 1080
agggacaaaa ggctcaggac tatgtttgtc ggttacctcc aagaattaga aggctggaag 1140
agagagctca aggaagggca aaggaagcac ccaccatgcc tttcagctgg attttcgata 1200
ggcaagtgaa gctgtaggtg gctaaagtgc aggacgaaac cgaaatggtt agtttcactc 1260
tttttcatgc ccatccctgc agaatcagaa gtagaggtag aattttgtag ttgctttttt 1320
attacaagtc cagtttagtt taaggtctgt ggaagggagt tagttgagga gtgaatttag 1380
taagttgtag atacagttgt ttcttgtgtt gtcatgagta tgctgataga gagcagctgt 1440
agttttgttg ttgtgttctt ttatatggtc tcttgtatga gtttcttttc tttccttttc 1500
ttctttcctt tcctctctct ctctctctct ctctctcttt ttctcttatc ccaagtgtct 1560
caagtataat aagcaaacga tccatgtggc aattttgatg atggtgatca gtctcacaac 1620
ttgatctttt gtcttctatt ggaaacacag cctgcttgtt tgaaaaaa 1668

<210> SEQ ID NO 16
<211> LENGTH: 396
<212> TYPE: PRT
<213> ORGANISM: Ricinus communis

<400> SEQUENCE: 16

```
Met Ala Leu Lys Leu Asn Pro Phe Leu Ser Gln Thr Gln Lys Leu Pro
  1               5                  10                  15

Ser Phe Ala Leu Pro Pro Met Ala Ser Thr Arg Ser Pro Lys Phe Tyr
             20                  25                  30

Met Ala Ser Thr Leu Lys Ser Gly Ser Lys Glu Val Glu Asn Leu Lys
         35                  40                  45

Lys Pro Phe Met Pro Pro Arg Glu Val His Val Gln Val Thr His Ser
     50                  55                  60

Met Pro Pro Gln Lys Ile Glu Ile Phe Lys Ser Leu Asp Asn Trp Ala
 65                  70                  75                  80

Glu Glu Asn Ile Leu Val His Leu Lys Pro Val Glu Lys Cys Trp Gln
                 85                  90                  95

Pro Gln Asp Phe Leu Pro Asp Pro Ala Ser Asp Gly Phe Asp Glu Gln
            100                 105                 110

Val Arg Glu Leu Arg Glu Arg Ala Lys Glu Ile Pro Asp Asp Tyr Phe
        115                 120                 125

Val Val Leu Val Gly Asp Met Ile Thr Glu Glu Ala Leu Pro Thr Tyr
    130                 135                 140

Gln Thr Met Leu Asn Thr Leu Asp Gly Val Arg Asp Glu Thr Gly Ala
145                 150                 155                 160

Ser Pro Thr Ser Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
            180                 185                 190

Val Asp Met Arg Gln Ile Glu Lys Thr Ile Gln Tyr Leu Ile Gly Ser
        195                 200                 205

Gly Met Asp Pro Arg Thr Glu Asn Ser Pro Tyr Leu Gly Phe Ile Tyr
    210                 215                 220

Thr Ser Phe Gln Glu Arg Ala Thr Phe Ile Ser His Gly Asn Thr Ala
225                 230                 235                 240

Arg Gln Ala Lys Glu His Gly Asp Ile Lys Leu Ala Gln Ile Cys Gly
                245                 250                 255

Thr Ile Ala Ala Asp Glu Lys Arg His Glu Thr Ala Tyr Thr Lys Ile
            260                 265                 270

Val Glu Lys Leu Phe Glu Ile Asp Pro Asp Gly Thr Val Leu Ala Phe
        275                 280                 285

Ala Asp Met Met Arg Lys Lys Ile Ser Met Pro Ala His Leu Met Tyr
    290                 295                 300

Asp Gly Arg Asp Asp Asn Leu Phe Asp His Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Asp Lys Leu Thr Gly Leu Ser Ala Glu
            340                 345                 350

Gly Gln Lys Ala Gln Asp Tyr Val Cys Arg Leu Pro Pro Arg Ile Arg
        355                 360                 365
```

Arg Leu Glu Glu Arg Ala Gln Gly Arg Ala Lys Glu Ala Pro Thr Met
    370                 375                 380

Pro Phe Ser Trp Ile Phe Asp Arg Gln Val Lys Leu
385                 390                 395

<210> SEQ ID NO 17
<211> LENGTH: 117
<212> TYPE: DNA
<213> ORGANISM: Brassica campestris

<400> SEQUENCE: 17
tgagagatag tgtgagagca ttagccttag agagagagag agagagcttg tgtctgaaag        60
aatccacaaa tggcattgaa gcttaaccct ttggcatctc agccttacaa cttccct         117

<210> SEQ ID NO 18
<211> LENGTH: 176
<212> TYPE: DNA
<213> ORGANISM: Brassica campestris

<400> SEQUENCE: 18
acttcatggg ctatttggac aagagcttgg actgcagaag agaaccgaca cggtgatctt        60
ctcaataagt atctttactt gtctggacgt gttgacatga ggcagattga aaagaccatt       120
cagtacttga ttggttctgg aatggatcct agaacagaga acaatcctta cctcgg          176

<210> SEQ ID NO 19
<211> LENGTH: 1495
<212> TYPE: DNA
<213> ORGANISM: Brassica campestris

<400> SEQUENCE: 19
tgagagatag tgtgagagca ttagccttag agagagagag agagagcttg tgtctgaaag        60
aatccacaaa tggcattgaa gcttaaccct ttggcatctc agccttacaa cttcccttcc       120
tcggctcgtc cgccaatctc tactttcaga tctcccaagt tcctctgcct cgcttcttct       180
tctcccgctc tcagctccaa ggaggttgag agtttgaaga agccattcac accacctaag       240
gaagtgcacg ttcaagtcct gcattccatg ccaccccaga agatcgagat cttcaaatcc       300
atggaagact gggccgagca gaaccttcta actcagctca agacgtggaa gaagtcgtgg       360
cagccccagg acttcttacc cgaccctgca tccgatgggt tcgaagatca ggttagagag       420
ctaagagaga gggcaagaga gctccctgat gattacttcg ttgttctggt gggagacatg       480
atcacggaag aggcgcttcc gacctatcaa accatgttga acactttgga tggagtgagg       540
gatgaaactg cgctagccc acttcatggg ctatttggac aagagcttg gactgcagaa       600 gagaaccgac acggtgatct tctcaataag tatctttact tgtctggacg tgttgacatg       660
aggcagattg aaaagaccat tcagtacttg attggttctg gaatggatcc tagaacagag       720
aacaatcctt acctcggctt catctacact tcattccaag aaagagccac cttcatctct       780
cacggaaaca cagctcgcca agccaaagag cacggagacc tcaagctagc ccaaatctgc       840
ggcacaatag ctgcagacga gaagcgtcat gagacagctt acaccaagat agttgagaag       900
ctctttgaga ttgatcctga tggtactgtg atggcgtttg cagacatgat gaggaagaaa       960
atctcgatgc ctgctcactt gatgtacgat gggcgggatg aaagcctctt gacaacttc      1020 tcttctgttg ctcagaggct cggtgtttac actgccaaag actatgcgga cattcttgag      1080
tttttggttg ggaggtggaa gattgagagc ttgaccgggc tttcaggtga aggaaacaaa      1140

```
gcgcaagagt acttgtgtgg gttgactcca agaatcagga ggttggatga gagagctcaa    1200
gcaagagcca agaaaggacc caaggttcct ttcagctgga tacatgacag agaagtgcag    1260
ctctaaaaag gaacaaagct atgaaacctt ttcactctcc gtcgtccctc atttgatcta    1320
tctgctcttg aaattggtgt agattactat ggtttgtgat attgttcgtg ggtctagtta    1380
caaagttgag aagcagtgat ttagtagctt tgttgtttcc agtctttaaa tgttttgtg     1440 tttggtcctt ttagtaaact tgttgtagtt aaatcagttg aactgtttgg tctgt         1495
```

<210> SEQ ID NO 20
<211> LENGTH: 398
<212> TYPE: PRT
<213> ORGANISM: Brassica campestris

<400> SEQUENCE: 20

```
Met Ala Leu Lys Leu Asn Pro Leu Ala Ser Gln Pro Tyr Asn Phe Pro
  1               5                  10                  15

Ser Ser Ala Arg Pro Pro Ile Ser Thr Phe Arg Ser Pro Lys Phe Leu
             20                  25                  30

Cys Leu Ala Ser Ser Ser Pro Ala Leu Ser Ser Lys Glu Val Glu Ser
         35                  40                  45

Leu Lys Lys Pro Phe Thr Pro Pro Lys Glu Val His Val Gln Val Leu
     50                  55                  60

His Ser Met Pro Pro Gln Lys Ile Glu Ile Phe Lys Ser Met Glu Asp
 65                  70                  75                  80

Trp Ala Glu Gln Asn Leu Leu Thr Gln Leu Lys Asp Val Glu Lys Ser
                 85                  90                  95

Trp Gln Pro Gln Asp Phe Leu Pro Asp Pro Ala Ser Asp Gly Phe Glu
            100                 105                 110

Asp Gln Val Arg Glu Leu Arg Glu Arg Ala Arg Glu Leu Pro Asp Asp
        115                 120                 125

Tyr Phe Val Val Leu Val Gly Asp Met Ile Thr Glu Glu Ala Leu Pro
    130                 135                 140

Thr Tyr Gln Thr Met Leu Asn Thr Leu Asp Gly Val Arg Asp Glu Thr
145                 150                 155                 160

Gly Ala Ser Pro Thr Ser Trp Ala Ile Trp Thr Arg Ala Trp Thr Ala
                165                 170                 175

Glu Glu Asn Arg His Gly Asp Leu Leu Asn Lys Tyr Leu Tyr Leu Ser
            180                 185                 190

Gly Arg Val Asp Met Arg Gln Ile Glu Lys Thr Ile Gln Tyr Leu Ile
        195                 200                 205

Gly Ser Gly Met Asp Pro Arg Thr Glu Asn Asn Pro Tyr Leu Gly Phe
    210                 215                 220

Ile Tyr Thr Ser Phe Gln Glu Arg Ala Thr Phe Ile Ser His Gly Asn
225                 230                 235                 240

Thr Ala Arg Gln Ala Lys Glu His Gly Asp Leu Lys Leu Ala Gln Ile
                245                 250                 255

Cys Gly Thr Ile Ala Ala Asp Glu Lys Arg His Glu Thr Ala Tyr Thr
            260                 265                 270

Lys Ile Val Glu Lys Leu Phe Glu Ile Asp Pro Asp Gly Thr Val Met
        275                 280                 285

Ala Phe Ala Asp Met Met Arg Lys Lys Ile Ser Met Pro Ala His Leu
    290                 295                 300

Met Tyr Asp Gly Arg Asp Glu Ser Leu Phe Asp Asn Phe Ser Ser Val
305                 310                 315                 320
```

```
Ala Gln Arg Leu Gly Val Tyr Thr Ala Lys Asp Tyr Ala Asp Ile Leu
            325                 330                 335

Glu Phe Leu Val Gly Arg Trp Lys Ile Glu Ser Leu Thr Gly Leu Ser
            340                 345                 350

Gly Glu Gly Asn Lys Ala Gln Glu Tyr Leu Cys Gly Leu Thr Pro Arg
            355                 360                 365

Ile Arg Arg Leu Asp Glu Arg Ala Gln Ala Arg Ala Lys Lys Gly Pro
370                 375                 380

Lys Val Pro Phe Ser Trp Ile His Asp Arg Glu Val Gln Leu
385                 390                 395

<210> SEQ ID NO 21
<211> LENGTH: 29
<212> TYPE: DNA
<213> ORGANISM: Carthamus tinctorius

<400> SEQUENCE: 21
gctaagctta argarathcc agaygayta                                       29

<210> SEQ ID NO 22
<211> LENGTH: 29
<212> TYPE: DNA
<213> ORGANISM: Carthamus tinctorius

<400> SEQUENCE: 22
gctaagctta argarathcc ggaygayta                                       29

<210> SEQ ID NO 23
<211> LENGTH: 29
<212> TYPE: DNA
<213> ORGANISM: Carthamus tinctorius

<400> SEQUENCE: 23
gctaagctta argarathcc cgaygayta                                       29

<210> SEQ ID NO 24
<211> LENGTH: 29
<212> TYPE: DNA
<213> ORGANISM: Carthamus tinctorius

<400> SEQUENCE: 24
gctaagctta argarathcc tgaygayta                                       29

<210> SEQ ID NO 25
<211> LENGTH: 26
<212> TYPE: DNA
<213> ORGANISM: Carthamus tinctorius
<220> FEATURE:
<221> NAME/KEY: modified_base
<222> LOCATION: (15)..(21)
<223> OTHER INFORMATION: n = a, c, g or t/u

<400> SEQUENCE: 25
agcgaattcg trttnagcat ngtytg                                          26

<210> SEQ ID NO 26
<211> LENGTH: 26
<212> TYPE: DNA
<213> ORGANISM: Carthamus tinctorius
<220> FEATURE:
<221> NAME/KEY: modified_base
<222> LOCATION: (21)
<223> OTHER INFORMATION: n = a, c, g or t/u
```

```
<400> SEQUENCE: 26
agcgaattcg trttyaacat ngtytg                                          26

<210> SEQ ID NO 27
<211> LENGTH: 3440
<212> TYPE: DNA
<213> ORGANISM: Brassica campestris

<400> SEQUENCE: 27
tctagaattc tctaattacg tctgtttgtt ctattttta tatgatatca aatattcgtc      60
ataaatatat ggtttaagat gccaaaaaat tatttacttg gtgaatataa tacgttaaat    120
attagaaata catcatttag ttaaataaat aaccaaaaac caaaaattca tatccgcgct    180
ggcgcgcggt cagggtctcg ttagttttaa aatcaatgca gtttacaatt aatttccagc   240
tgaaaataag tataatttgt attgaaatta taaagtgaca tttttgtgt aacaaatatt    300 ttgtgtaaca agaattaaaa aaaaaaacag aaaatactca gcttttttaa taataaaaaa    360
aattaattga gttagaaaat tgttgtacca ataacaaaag atttatatgg aattataaaa    420
tcaacacacc aataacacaa gactttttaa aaatttaaga ataatataag caataacaat    480
agaatcttca aattcttcaa atccttaaaa atcaatctcc cactattaat ccccttagt     540 tttagttggt aatggcaacg tttgttgact accgtattgt aacttttgtc aaattgtcat    600
aaatacgtgt caaactctgg taaaaaatta gtctgctaca tctgtctttt atttataaaa    660
cacagctgtt aatcagaatt tggtttatta aatcaacaac ctgcacgaaa cttgtgtgag    720
catattttgt ctgtttctgg ttcatgacct tcttccgcat gatggccaag tgtaatggcc    780
acttgcaaga gcgtttcttc aacgagataa gtcgaacaaa tatttgtccg ttacgaccac    840
atataaaatc tccccatctc tatatataat accagcattc accatcatga atacctcaaa    900
tcccaatctc acaaatactt caataaaaag accaaaaaaa attaaagcaa agaaaagcct    960
tcttgtgcac aaaaaaaaaa gaagccttct aggttttcac gacatgaagt tcactactct   1020
aatggtcatc acattggtga taatcgccat ctcgtctcct gttccaatta gagcaaccac   1080
ggttgaaagt ttcggagaag tggcacaatc gtgtgttgtg acagaactcg ccccatgctt   1140
accagcaatg accacggcag gagacccgac tacagaatgc tgcgacaaac tggtagagca   1200
gaaaccatgt ctttgtggtt atattcgaaa cccagcctat agtatgtatg ttacttctcc   1260
aaacggtcgc aaagtcttag attttttgtaa ggttcctttt cctagttgtt aaatctctca   1320
agacattgct aagaaaaata ttattaaaaa taaagaatc aaactagatc tgatgtaaca    1380
atgaatcatc atgttatggt tgaagcttat atgctgaagt gtttgatttt atatatgtgt   1440
gtgtgtgtgt cctgctcaat ttttgaaaca cacacgtttc tcctgatttg gatttaaatt   1500
atattttgag ttaaaaaaaa gaaaagatg gaatgctatt tatacaagtt gatgaaaaag    1560
tggaagtaca atttagatat ctcctacact taagaatga aacaataata gacttacgaa    1620
acaaatgaaa aatacataaa ttgtcgacaa tcaacgtccg atgacgagtt tattattaaa    1680
aatttgtgtg aaggactagc agttcaacca aatgatattg aacatataca tcaacaaata    1740
tgataatcat aaaagagaga atgggggggg ggtgtcgttt accagaaacc tcttttctc    1800 agctcgctaa aaccctacca ctagagacct agctctgacc gtcggctcat cggtgccgga    1860
ggtgtaacct ttcttcccca tgacccgaaa cctctctttc ccaactcacg aaaaccctac    1920
aatcaaaaac ctagctccga ccgtcggctc atcggtgccg aaggtgtaac ctttctctcc    1980
catcatagtt tctcgtaaat gaaagctaat tgggcaatcg atttttttaat gtttaaacca    2040
```

```
tgccaagcca tttcttatag gacaattgtc aataatagca tcttttgagt tttgtctcaa    2100
aagtgacact agaagaaaaa agtcacaaaa atgacattca ttaaaaagta aaatatccct    2160 aataccttg gtttaaatta aataagtaaa caaaaataaa taaaaacaaa taaaataaaa     2220
ataaaaaatg aaaaaaagaa attttttat agtttcagat tatatgtttt cagattcgaa     2280 atttttaaa ttccctttt taaattttct ttttgaaat ttttttttt gaaatttttt        2340 gaaactgttt ttaaaatttt tatttaat ttttagtat ttatttta ttttataaaa         2400 ttttaaacgc taattccaaa actcccccc cccccccc cccaattctc tcctagtctt       2460 tttctcttc tatatttgg gcttctatct tctctttt ttcaggccc aaagtatcat          2520 gtgtaacaac cggtgttcaa aaacgcgccc gcctggccgt ttactcgccc gattaaatga    2580
tgatcggaag gctgccatgg cgaggcggag gtaatcagtg ttctaggcg ctgaaactag     2640 aaaaccttca aaaatcgaaa ttttaagagc taaatcggtg tttatctcat gaatctatta    2700
tatttagttg aaactcacaa gatcggttg taaaaactat gaaatcgtgc aaaaaaaatg     2760
aagaacaaaa tattctcaga tctggaaaac acagagaaga ggttgaagat gagggtaaaa    2820 tcgtatttg tcattcatta aactaaaatc aaaaaaaaat gatgcaaaat tcaatgataa     2880
taactcgaac tcgcaaccat atgcatcttt agactgcgac acggaccact agactaagca    2940 atttaatgt ttattcatca cagacctaat atatgtctaa aactaggcgc cgagtacgcc     3000
ccgcttaatc ccgagtttt gttagctcgc tagacccagg gtcaccgccc gactaacgag    3060
tagcgtaatt ctgaactggg gtaacaacat agagaacatc gccgacccct ccctgccgat   3120
gatgccgcct ccgatgaact tcctgtaacg ccttcagttt ccattgattt tcccctttaa   3180
tctgatcagt tccatgtttt atccaactca tcccactccg tagcatttaa tcgatctcat   3240
catttacata cataaccagt aggaggtctc atataaattt gaacgtttcc agcgatgaac   3300
agtgccaatc tctgcgaaat ccatttctct aagctcaggg ctggcggctg cagcccgggg   3360
atccactagt tctaggcggc cgcaccgcgg tggagctcca attcgcccta tagtgagtcg   3420
tattacgcgc gctcactggc                                               3440

<210> SEQ ID NO 28
<211> LENGTH: 3898
<212> TYPE: DNA
<213> ORGANISM: Brassica campestris

<400> SEQUENCE: 28
ctcgagagct gaaggatttt ttgttagaga ttcaacgaca gatggaccct tcctccacta     60
ggcaactgca agaacctaac aatgcaaata tcactcctcc tcagccttca aggagcgtta   120
ataggactgg aacaagcggt caagtgagta aattttcctt ccaagataga tctctatggt   180
tcggttcatg aagtttgtgg tttaattgtg tagcaacagg atagtgcaag tgagaataga   240
gttcgacctc atctacctac cccggaacct ctgaatgtat ccccattgaa gaagaagagg   300
gcaaatcctg cacccagaag gataaagaaa ttttggacgc ctgaagaagt ggcagttctg   360
agggaaggag taaagagta tgtctactac tactactcta taatcaagtt tcaagaagct   420
gagcttggct ctcactttat atgtttgatg ttgttgtgca ggtatggtaa atcatggaaa   480
gagataaaga atgcaaaccc tgaagtattg gcagagagga ctgaggtgag agagcatgtc   540 actttgtgt tactcatctg aattatctta tatgcgaatt gtaagtggta ctaaaaggtt    600 tgtaacttt ggtaggtgga tttgaaggat aaatggagga acttgcttcg gtagcggtaa   660
caagttttat attgctatga agtttttttg cctgcgtgac gtatcagcag ctgtggagaa    720
```

| | |
|---|---|
| gatggtatta gaaagggtct tttcacattt tgtgttgtga caaatattaa ttcggccggt | 780 |
| atggtttggt taagacttgt tgagagacgt gtggggtttt ttgatgtata attagtctgt | 840 |
| gtttagaacg aaacaagact tgttgcgtat gctttttta acttgagggg gtttgttgtt | 900 |
| gttagttagg aacttgactt tgtctctttc tctcaagatc tgattggtaa ggtctgggtg | 960 |
| gtagtactgt ttggtttaat ttgttttgac tattgagtca ctgtggccca ttgactttaa | 1020 |
| attaggctgg tatatttttt ggtttaaaac cggtctgaga tagtgcaatt tcgattcagt | 1080 |
| caattttaaa ttcttcaagg taatgggctg atacttgta tagttttaag acttaacagg | 1140 |
| ccttaaaagg cccatgttat cataaaacgt cattgtttag agtgcaccaa gcttataaaa | 1200 |
| tgtagccagg ccttaaaaga cttaacaggc cttaaaagac ttaacattcc ttaaaaggcc | 1260 |
| catgttatca taaaacgtca tcgttttgag tgcaccaagc taaatgtagc caggccttaa | 1320 |
| aagacttaac aggccttaaa aggcccatgt tatcataaaa cgccgtcgtt ttgagtgcac | 1380 |
| caagcttata aatgtagcca gctacctcgg gacatcacgc tctttgtaca ctccgccatc | 1440 |
| tctctctctc tcgagcagat ctctctcggg aatatcgaca atgtcgacca ctttctgctc | 1500 |
| ttccgtctcc atgcaagcca cttctctggt aatctcatct ccttcttgtg ttcccagatc | 1560 |
| gctctgatca tactttcttt tagatcattt gcctctgatc tgttgcttga tgtttgttaa | 1620 |
| ctctccacgc atgtttgatt atgttgagaa ttagaaaaaa aatgttagct ttacgaatct | 1680 |
| ttagtgatca tttcaattgg atttgcaatc ttgtgtgaca tttgaggctt gtgtagattt | 1740 |
| cgatctgtat tcattttgaa tcacagctat aatagtcatt tgagtagtag tgttttaaa | 1800 |
| tgaacatgtt ttgttgtatt gatggaacaa acaggcagca acaacgagga ttagtttcca | 1860 |
| gaagccagct ttggtttcaa cgactaatct ctccttcaac ctccgccgtt caatccccac | 1920 |
| tcgtttctca atctcctgcg cggtatgttc tcattctcag catttatttc gagcttgctt | 1980 |
| gtcatggtac tctctctaat tgtctatttg gtttattagg ccaaaccaga gacggttgag | 2040 |
| aaagtgtcta agatagttaa gaagcagcta tcactcaaag acgaccaaaa ggtcgttgcg | 2100 |
| gagaccaagt ttgctgatct tggagcagat tctctcgaca ctgtaagtca tcaatcattc | 2160 |
| tcttatgtga ataaagagaa cttgaagagt ttgttttaa catattaact gagtgttttg | 2220 |
| catgcaggtt gagatagtga tgggtttaga ggaagagttt gatatcgaaa tggctgaaga | 2280 |
| gaaagctcag aagattgcta ctgtggagga agctgctgaa ctcattgaag agctcgttca | 2340 |
| acttaagaag taattttagt attaagagca gccaaggctt tgttgggttt gttgttttca | 2400 |
| taatcttcct gtcatttttct ttttctttaa tgtgtcaagc gactctgttg gtttaaagta | 2460 |
| gtatctgttt gccatggatc tctctctatt tgtcgactga aaacttttgg tttacacatg | 2520 |
| aaagcttgtt cttgttcttt cttaaatcga atgccaaat gcgagattag ggaatcttgt | 2580 |
| attaacacat acataagtca aagagtaggc cctaagatga caatttataa acaatcctat | 2640 |
| tcacattgta tatacaggtt atgattattc ccaatcagcg tcaaagaatc cagcatcttt | 2700 |
| catctctgaa tagtagacat tctccaagtt cacatcttcc tcctgcacca aaaaccagta | 2760 |
| ctaaatcatg aacattgcaa taatcacatg cctaggcgag agttttggtg atgtggtgtt | 2820 |
| agtgatagtg atactgatgg tgctagagcg gttaagaagg attaacctgg aagaagtctg | 2880 |
| caaggaaagt aacatagaga agaggaagat aggagtggta caaacacttt gtgatcccat | 2940 |
| acagcctccc agcattttc aaatgttatt tccttacata aagaaacaag agaagtctga | 3000 |
| ctagatgata tttatatagg ataagtgttt taccataagc caaagtgagc gccgtttgca | 3060 |
| agagctaacc agacagtaca cgtttggcat atatctcatc aacatgatct gaaaagtaac | 3120 |

-continued

```
atatcacagt taatgaacac aatggttacc ttgagaagca aatcaagacc tataacaagc    3180
ccagagatga ggaaagtccg tgtcaacgct tcaccgccat tcgcgtagtt tccttggaag    3240
acaaaggcca ccaaccaaac ttacttccag aaacaacact ccaaatgttg tcaacaaagt    3300
caatagattc caaactactt cgttacaggg ttgtatagat aatataatag aatagtggga    3360
agatagtata aataaaataa ataaaagatc ctatcggtaa atagtttata atatcggggg    3420
cgtatataaa gtataaaaga aactcttctc caatccgacc gttgaaaatc actctcaatc    3480
tctggcgtaa cgaccggatc gttcgcgcgt aattttcgct gctataaata gaaactttcc    3540
tcttctgttt ctcgatcaaa attttttttt ggaaaaatta gtttgaatc tatcgtagat    3600 gctgtgacaa aaaaaaattg ttttatcgaa gatgagaaac atgaggcctg ttcatgcaag    3660
gaaccagacc acggatccat cttcgccgat gatgacgtct cctctgatga atcgtcacgc    3720
acggacagga tccaacgctg gaccagcatc taacgccaag aaagcacaga cgaaagcagc    3780
agctcagaga ctcgcggctg tgatgtcgaa ccaaacaggc gacgatgaag acagtgatga    3840
tgacctttcc tttgactaca cgctgtcgg aagcattggt ctcgctgccg gaagatct      3898
```

<210> SEQ ID NO 29
<211> LENGTH: 4325
<212> TYPE: DNA
<213> ORGANISM: Brassica campestris
<220> FEATURE:
<221> NAME/KEY: modified_base
<222> LOCATION: (431)..(3804)
<223> OTHER INFORMATION: n = a, c, g or t/u

<400> SEQUENCE: 29

```
ctcgaggcag tcactaacat gaagtttgac gaggagccca actatgggaa gcttatttct      60
cttttcgata ctctaattga gccgtgcgct ctatctagac caattagaat tgatgggagct    120 ctaaaggttg ctggctgttt tcttgttcat atgattaact tctaaacttg tgtataaata    180
ttctctgaaa gtgcttcttt tggcatatgt aggttgggca aaaacgagga agattgcttc    240
tcaatttgga agaggatgaa cagccgaaga agaaaataag aataggcagt cctgctactc    300
aatggatctc agtctataac ggtcgtcgtc ccatgaaaca gaggtaaaac attttttgca    360
tatacacttt gaaagttcct cactaactgt gtaatctttt ggtagatatc actacaatgt    420
cggagagaca anggctgsnc ancatataca aaagggaaat gaagatggcc ttttgattag    480
ctgtgtagca tcagcagcta atctctgggc tctcatcatg gatgctggaa ctggattcac    540
ttctcaagtt tatgagttgt caccggtctt cctacacaag gtaataatca gttgaagcaa    600
ttaagaatca atttgatttg tagtaaacta agaagaactt accttatgtt ttccccgcag    660
gactggatta tggaacaatg ggaaaagaac tactatataa gctccatagc tggttcgat     720 aacgggagct ctttagttgt tatgtcaaaa ggttagtgtt tagtgaataa taaacttata    780
ccacaaagtc ttcattgact tatttatata cttgttgtga attgctagga actacttatt    840
ctcagcagtc atacaaagtg agtgactcat ttccgttcaa gtggataaat aagaaatgga    900
aagaagattt tcatgtaacc tccatgacaa ctgctggtaa tcgttggggt gtggtaatgt    960
cgaggaactc tggcttctct gatcaggtag gttttttgtct cttattgtct ggtgtttta    1020 tttttcccctg atagtctaat atgataaact ctgcgttgtg aaaggtggtg gagcttgact   1080
ttttgtaccc aagcgatggg atacatagga ggtgggagaa tgggtataga ataacatcaa    1140
tggcagcaac tgcggatcaa gcagctttca tattaagcat accaaagcgt aagatggtgg    1200
atgaaactca agagactctc cgcaccaccg ccttttccaag tactcatgtc aaggttggtt    1260
```

```
tctttagctt tgaacacaga tttggatctt tttgttttgt ttccatatac ttaggacctg   1320
agagcttttg gttgattttt ttttcaggac aaatgggcga agaatctgta cattgcatca   1380
atatgctatg gcaggacagt gtgctgatac acacttaagc atcatgtgga aagccaaaga   1440
caattggagc gagactcagg gtcgtcataa taccaatcaa agacgtaaaa ccagacgcaa   1500
cctctttggt tgaatgtaat gaaagggatg tgtcttggta tgtatgtacg aataacaaaa   1560
gagaagatgg aattagtagt agaaatattt gggagctttt taagcccttc aagtgtgctt   1620
tttatcttat tgatatcatc catttgcgtt gtttaatgcg tctctagata tgttcctata   1680
tctttctcag tgtctgataa gtgaaatgtg agaaaaccat accaaaccaa aatattcaaa   1740
tcttattttt aataatgttg aatcactcgg agttgccacc ttctgtgcca attgtgctga   1800
atctatcaca ctagaaaaaa acatttcttc aaggtaatga cttgtggact atgttctgaa   1860
ttctcattaa gttttttattt tctgaagttt aagtttttac cttctgtttt gaaatatatc   1920
gttcataaga tgtcacgcca ggacatgagc tacacatcgc acatagcatg cagatcagga   1980
cgatttgtca ctcacttcaa acacctaaga gcttctctct cacagcgcac acacatatgc   2040
atgcaatatt tacacgtgat cgccatgcaa atctccattc tcacctataa attagagcct   2100
cggcttcact ctttactcaa accaaaactc atcactacag aacatacaca aatggcgaac   2160
aagctcttcc tcgtctcggc aactctcgcc ttgttcttcc ttctcaccaa tgcctccgtc   2220
tacaggacgg ttgtggaagt cgacgaagat gatgccacaa atccagccgg cccatttagg   2280
attccaaaat gtaggaagga gtttcagcaa gcacaacacc tgaaagcttg ccaacaatgg   2340
ctccacaagc aggcaatgca gtccggtagt ggtccaagct ggaccctcga tggtgagttt   2400
gattttgaag acgacgtgga gaaccaacaa cagggcccgc agcagaggcc accgctgctc   2460
cagcagtgct gcaacgagct ccaccaggaa gagccacttt gcgtttgccc aaccttgaaa   2520
ggagcatcca aagccgttaa acaacagatt cgacaacaac agggacaaca aatgcaggga   2580
cagcagatgc agcaagtgat tagccgtatc taccagaccg ctacgcactt acctagagct   2640
tgcaacatca ggcaagttag catttgcccc ttccagaaga ccatgcctgg gcccggcttc   2700
tactagattc caaacgaata tcctcgagag tgtgtatacc acggtgatat gagtgtggtt   2760
gttgatgtat gttaacacta catagtcatg gtgtgtgttc cataaataat gtactaatgt   2820
aataagaact actccgtaga cggtaataaa agagaagttt ttttttttac tcttgctact   2880
ttcctataaa gtgatgatta acaacagata caccaaaaag aaaacaatta atctatattc   2940
acaatgaagc agtactagtc tattgaacat gtcagatttt cttttttctaa atgtctaatt   3000 aagccttcaa ggctagtgat gataaaagat catccaatgg gatccaacaa agactcaaat   3060
ctggttttga tcagatactt caaaactatt tttgtattca ttaaattatg caagtgttct   3120
tttatttggt gaagactctt tagaagcaaa gaacgacaag cagtaataaa aaaaacaaag   3180
ttcagtttta agatttgtta ttgacttatt gtcatttgaa aaatatagta tgatattaat   3240
atagttttat ttatataatg cttgtctatt caagatttga gaacattaat atgatactgt   3300
ccacatatcc aatatattaa gtttcatttc tgttcaaaca tatgataaga tggtcaaatg   3360
attatgagtt ttgttatttta cctgaagaaa agataagtga gcttcgagtt tctgaagggt   3420
acgtgatctt catttcttgg ctaaaagcga atatgacatc acctagagaa agccgataat   3480
agtaaactct gttcttggtt tttggtttaa tcaaaccgaa ccggtagctg agtgtcaagt   3540
cagcaaacat cgcaaaccat atgtcaattc gttagattcc cggtttaagt tgtaaaccgg   3600
tatttcattt ggtgaaaacc ctagaagcca gccanccttt ttaatctaat ttttgcaaac   3660
```

```
gagaagtcac cacacctctc cactaaaacc ctgaacctta ctgagagaag cagagncann    3720
aaagaacaaa taaacccga agatgagacc accacgtgcg gcgggacgtt caggggacgg     3780
ggaggaagag aatgrcggcg gnsntttggt ggcggcggcg gacgttttgg tggcggcggt    3840
ggacgttttg gtggcggcgg tggacctttg gtggtggata tcgtgacgaa ggacctccca    3900
gtgaagtcat tggttcgttt actcttttct tagtcgaatc ttattcttgc tctgctcgtt    3960
gttttaccga taaagcttaa gactttattg ataaagttct cagctttgaa tgtgaatgaa    4020
ctgtttcctg cttattagtg ttcctttgtt ttgagttgaa tcactgtctt agcacttttg    4080
ttagattcat ctttgtgttt aagttaaaag gtagaaactt tgtgacttgt ctccgttatg    4140
acaaggttaa ctttgttggt tataacagaa gttgcgacct ttctccatgc ttgtgagggt    4200
gatgctgtgg accaagctct ctcaggcgaa gatcccttac ttcaatgccc caatctactt    4260
ggaaaacaag acacagattg ggaaagttga tgagatccaa gcttgggctg caggtcgacg    4320
aattc                                                               4325
```

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
cggatccact gcagtctaga gggcccggga                                       30

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
aatttcccgg gccctctaga ctgcagtgga tccgagct                              38

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gtaagtaggt agggcttcct ctgtaatcat atctccaacc aaaacaacaa                 50

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
cttaagaagt aacccgggct gcagttttag tattaagag                             39

```
<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
ggaattcgtc gacagatctc tgcagctcga gggatccaag ctt                    43

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35 ccattttttga tcttcctcga gcccgggctg cagttcttct tcttcttg              48

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
gctcgttttt tttttctctg cagcccgggc tcgagtcaca gcttcacc               48

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
actgactgca gcccgggctc gaggaagatc aaaaatggct cttc                   44

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
gagtagtgaa cttcatggat cctcgaggtc ttgaaaacct aga                    43

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
caatgtcttg agagatcccg ggatccttaa caactaggaa aagg                   44
```

```
<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
gtaagacacg acttatcgcc actg                                              24

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
ggaattcgtc gacagatctc tgcagctcga gggatccaag ctt                         43

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
gcttgttcgc catggatatc ttctgtatgt tc                                     32

<210> SEQ ID NO 43
<211> LENGTH: 143
<212> TYPE: DNA
<213> ORGANISM: Simmondsia chinensis
<220> FEATURE:
<221> NAME/KEY: modified_base
<222> LOCATION: (11)
<223> OTHER INFORMATION: n = a, c, g or t/u

<400> SEQUENCE: 43
gatgccaaaa ngcctcacat gcctcctaga gaagctcatg tgcaaaagac ccattcaatk       60
ccgcctcaaa agattgagat tttcaaatcc ttggagggtt gggctgagga gaatgtcttg      120
gtgcatctta aacctgtgga gaa                                              143

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
gatccgcggc cgcgaattcg agctcccccc cccc                                   34

<210> SEQ ID NO 45
<211> LENGTH: 20
<212> TYPE: DNA
<213> ORGANISM: Artificial Sequence
```

```
-continued

<220> FEATURE:
<223> OTHER INFORMATION: Description of Artificial Sequence:  Synthetic
      Primer

<400> SEQUENCE: 45
gcgccggcgc ttaagctcga                                                    20
```